(12) United States Patent
Yamada et al.

(10) Patent No.: US 10,471,096 B2
(45) Date of Patent: Nov. 12, 2019

(54) MEDICINAL COMPOSITION, BLOOD TREATMENT DEVICE, COSMETIC, FOOD AND DRINK USING COMBUSTION SYNTHESIS MATERIAL

(71) Applicants: Osamu Yamada, Osaka (JP); OSU CORPORATION, Osaka (JP)

(72) Inventors: Osamu Yamada, Osaka (JP); Junpei Maruo, Osaka (JP)

(73) Assignees: Osamu Yamada, Osaka (JP); OSU CORPORATION, Osaka (JP)

( * ) Notice: Subject to any disclaimer, the term of this patent is extended or adjusted under 35 U.S.C. 154(b) by 0 days.

(21) Appl. No.: 15/540,830

(22) PCT Filed: Jan. 5, 2016

(86) PCT No.: PCT/JP2016/050106
§ 371 (c)(1),
(2) Date: Jun. 29, 2017

(87) PCT Pub. No.: WO2016/111285
PCT Pub. Date: Jul. 14, 2016

(65) Prior Publication Data
US 2018/0008633 A1    Jan. 11, 2018

(30) Foreign Application Priority Data

Jan. 6, 2015   (JP) ................................ 2015-001176
Aug. 20, 2015  (JP) ................................ 2015-162792

(51) Int. Cl.

| | |
|---|---|
| *A61K 33/24* | (2019.01) |
| *A23L 2/52* | (2006.01) |
| *A61K 8/29* | (2006.01) |
| *A61Q 11/00* | (2006.01) |
| *A61Q 19/00* | (2006.01) |
| *A61K 33/00* | (2006.01) |
| *A61K 33/22* | (2006.01) |
| *A61K 33/26* | (2006.01) |
| *A61K 33/34* | (2006.01) |
| *A61K 33/38* | (2006.01) |
| *A23L 33/16* | (2016.01) |
| *A61K 8/11* | (2006.01) |
| *A61K 8/19* | (2006.01) |
| *A61K 8/25* | (2006.01) |
| *A61K 33/44* | (2006.01) |

(52) U.S. Cl.
CPC .............. *A61K 33/24* (2013.01); *A23L 2/52* (2013.01); *A23L 33/16* (2016.08); *A61K 8/11* (2013.01); *A61K 8/19* (2013.01); *A61K 8/25* (2013.01); *A61K 8/29* (2013.01); *A61K 33/00* (2013.01); *A61K 33/22* (2013.01); *A61K 33/26* (2013.01); *A61K 33/34* (2013.01); *A61K 33/38* (2013.01); *A61K 33/44* (2013.01); *A61Q 11/00* (2013.01); *A61Q 19/00* (2013.01); *A23V 2002/00* (2013.01); *Y02A 50/473* (2018.01); *Y02A 50/475* (2018.01)

(58) Field of Classification Search
CPC .......... A61K 33/38; A61K 8/29; A61Q 11/00; A61Q 19/00
See application file for complete search history.

(56) References Cited

U.S. PATENT DOCUMENTS

| 4,909,842 A | 3/1990 | Dunmead et al. |
| 4,988,645 A | 1/1991 | Holt et al. |
| 5,151,122 A | 9/1992 | Atsumi et al. |
| 5,279,737 A * | 1/1994 | Sekhar ............... B01D 39/2051 210/490 |
| 5,558,071 A * | 9/1996 | Ward ........................ F02P 3/02 123/598 |
| 6,579,851 B2 * | 6/2003 | Goeke .................... A61K 38/26 514/11.7 |
| 8,461,129 B2 * | 6/2013 | Bolduc ................... A61L 15/28 127/49 |
| 2005/0207929 A1 | 9/2005 | Yamada |
| 2010/0040655 A1 * | 2/2010 | Ren ........................ A01N 25/34 424/402 |
| 2010/0151043 A1 | 6/2010 | Mano et al. |

(Continued)

FOREIGN PATENT DOCUMENTS

| EP | 0681841 A1 | 11/1994 |
| JP | 3021113 U | 11/1995 |

(Continued)

OTHER PUBLICATIONS

ACS "Can Cancer Be Prevented?" 2010, p. 1 (Year: 2010).*
Atopic dermatitis (http://www.dermnetnz.org/dermatitis/atopic-causes.html) 2015, pp. 1-4 (Year: 2015).*
Sausville et al. "Contributions of Human Tumor Xenografts to Anticancer Drug Development" Cancer Res. 2006, 66, 7, 3351-3354 (Year: 2006).*
Ahmed, A.U. "An overview of inflammation: mechanism and consequences" Front. Biol. 2011, 6(4): 274-281 (Year: 2011).*
Thaiwat, S. et al. "Omalizumab treatment in severe adult atopic dermatitis" Asian Pac J Allergy Immunol 2011;29:357-60 (Year: 2011).*

(Continued)

*Primary Examiner* — Andrew S Rosenthal
(74) *Attorney, Agent, or Firm* — MH2 Technology Law Group, LLP

(57) ABSTRACT

Disclosed are a pharmaceutical composition, cosmetic product, and food or drink product each comprising a porous ceramic obtained by combustion synthesis of a starting material comprising (1) titanium and (2) at least one member selected from the group consisting of carbon, boron, nitrogen, and silicon; a pharmaceutical composition and cosmetic product each comprising a radical- and nanobubble-containing liquid; and a blood treatment device comprising a blood flow channel for extracorporeal circulation of a patient's blood, the blood flow channel being provided with the porous ceramic above, and the porous ceramic and the blood are brought into contact with each other.

9 Claims, 40 Drawing Sheets

(56) References Cited

U.S. PATENT DOCUMENTS

| | | | | |
|---|---|---|---|---|
| 2011/0028412 | A1* | 2/2011 | Cappello | A61K 31/7004 514/25 |
| 2013/0041004 | A1* | 2/2013 | Drager | A61K 9/08 514/394 |
| 2013/0084243 | A1* | 4/2013 | Goetsch | C07K 16/2863 424/1.49 |
| 2013/0096073 | A1* | 4/2013 | Sidelman | A61K 38/1709 514/21.6 |

FOREIGN PATENT DOCUMENTS

| | | |
|---|---|---|
| JP | H11-5729 A | 1/1999 |
| JP | 2002-316946 A | 10/2002 |
| JP | 2003-55063 A | 2/2003 |
| JP | 2003-192467 A | 7/2003 |
| JP | 2005-270358 A | 10/2005 |
| JP | 2006-69935 A | 3/2006 |
| JP | 2010-519294 A | 6/2010 |
| JP | 5102749 B2 | 10/2012 |
| WO | 92/13977 A1 | 8/1992 |
| WO | 92/22682 A1 | 12/1992 |
| WO | 94/17012 A1 | 8/1994 |
| WO | 95-14484 A1 | 6/1995 |
| WO | 2004/091308 A1 | 10/2004 |
| WO | 2008/072371 A1 | 6/2008 |
| WO | 2008/103082 A1 | 8/2008 |

OTHER PUBLICATIONS

Zumla, A. et al. "Tuberculosis" N Engl J Med 2013, 368 (8), 745-755 (Year: 2013).*

Sepsis (https://www.mayoclinic.org/diseases-conditions/sepsis/symptoms-causes/syc-20351214) 2018, pp. 1-7 (Year: 2018).*

Food Poisoning (https://www.healthline.com/health/food-poisoning) 2017, pp. 1-13 (Year: 2017).*

Yusuf et al. "Paclitaxel Resistance: Molecular Mechanisms and Pharmacologic Manipulation" Curr. Cancer Drug Tar. 2003, 3, 1-19 (Year: 2003).*

Suggitt, M. et al. "50 Years of Preclinical Anticancer Drug Screening: Empirical to Target-Driven Approaches" Clinical Cancer Research 2005, 11, 971-981 (Year: 2005).*

Ayers, R. et al. "The Application of Energetic SHS Reactions in the Synthesis of Multifunctional Bone Tissue Engineering and Drug Delivery Systems" Mater. Res. Soc. Symp. Proc. 2006, 896, 1-13 (Year: 2006).*

Johnson, C.T. et al. "Scaffold-based Anti-infection Strategies in Bone Repair" Ann Biomed Eng. 2015, 43(3), 515-528 (Year: 2015).*

International Search Report dated Mar. 15, 2016 from International Application No. PCT/JP2016/050106, 6 pages.

Extended European Search Report dated Jul. 26, 2018 from European Application No. 16735024.8, 13 pages.

* cited by examiner

Particle Size of Ground Porous Ceramic (μm)

Fig. 5-2 (Continued from Fig. 5-1)
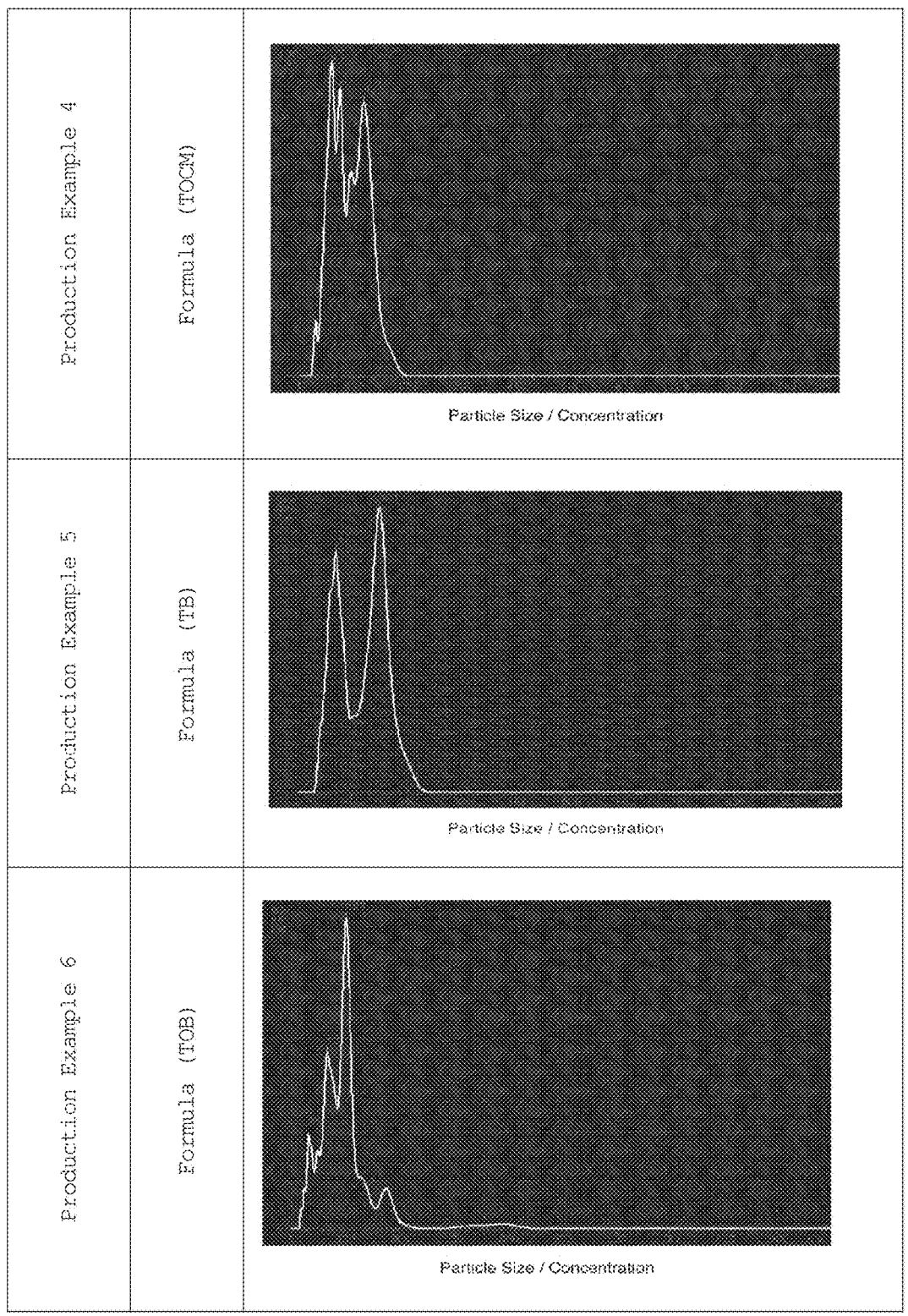

Fig. 5-3 (Continued from Fig. 5-2)
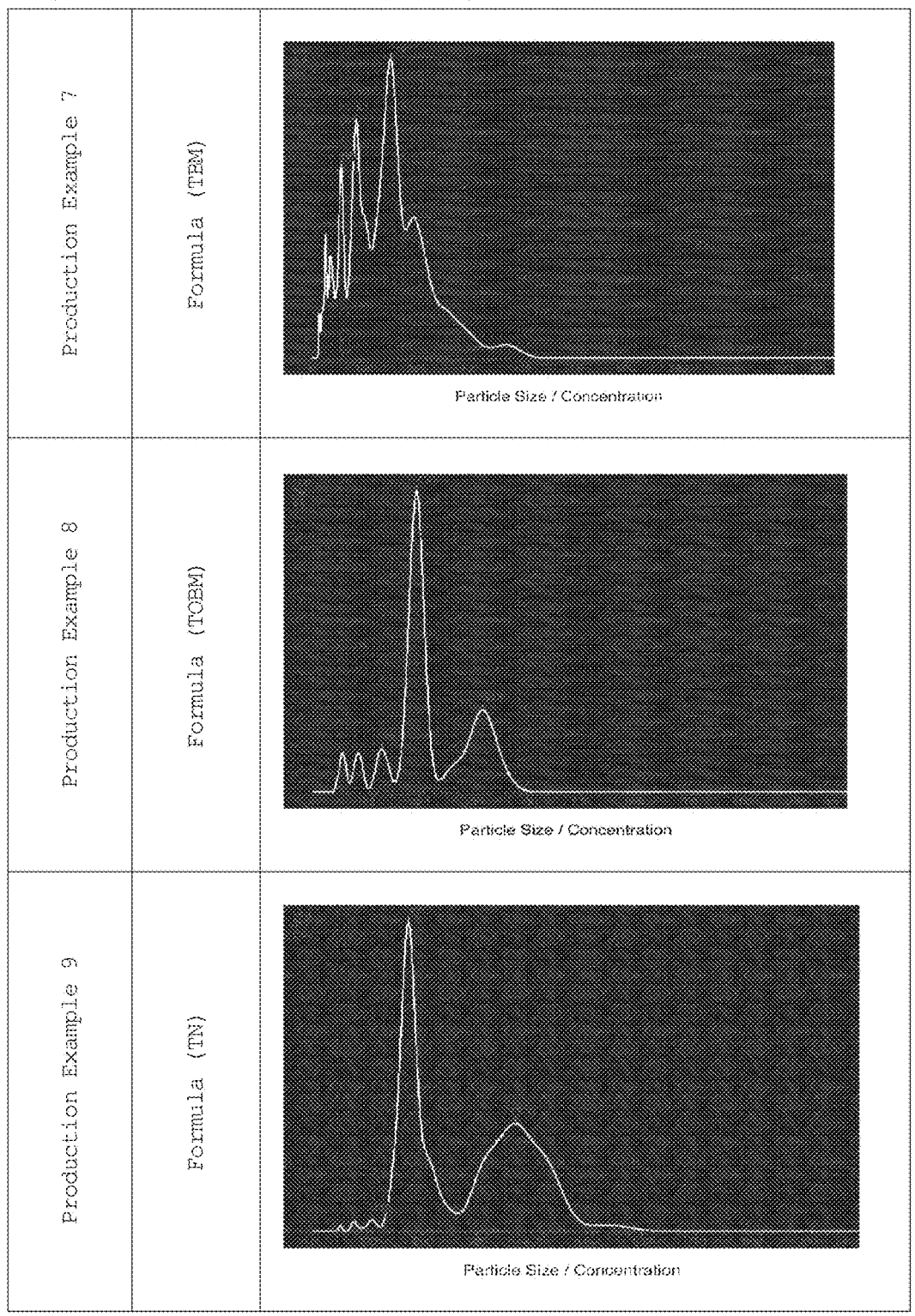

Fig. 5-4 (Continued from Fig. 5-3)
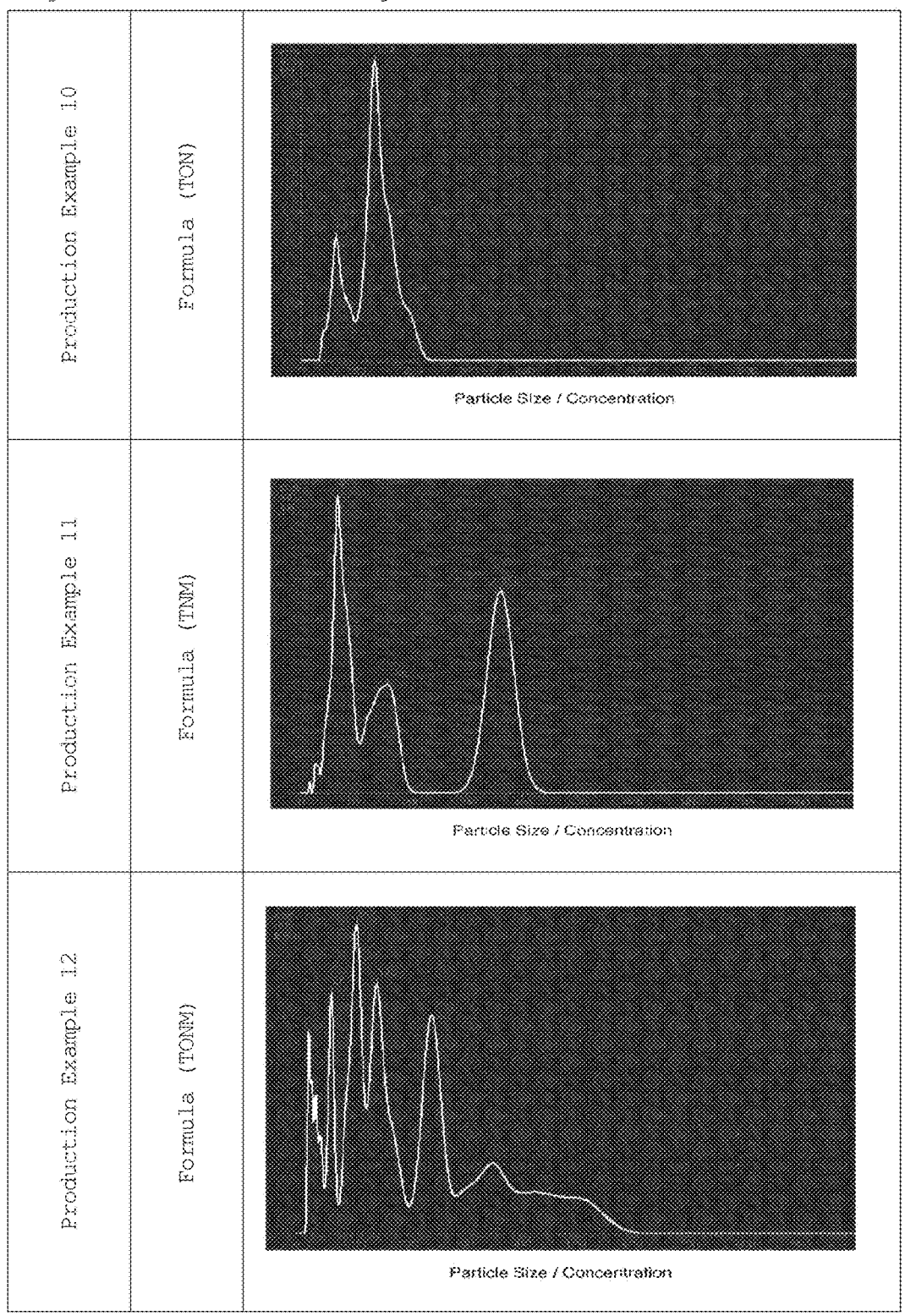

Control Group    Test Group (TOC)    Test Group (TOCM)

Swelling of Hepatic Tissue around Diaphragm Connection

Healing Process of Psychosomatic Skin Disease Treated by the Porous Ceramic

MEDICINAL COMPOSITION, BLOOD TREATMENT DEVICE, COSMETIC, FOOD AND DRINK USING COMBUSTION SYNTHESIS MATERIAL

CROSS-REFERENCE TO RELATED APPLICATIONS

This application is a U.S. National Stage application of PCT/JP2016/050106 filed 5 Jan. 2016, which claims priority to Japanese Application No. 2015-001176 filed 6 Jan. 2015, and Japanese Application No. 2015-162792 filed 20 Aug. 2015, the entire disclosures of which are hereby incorporated by reference in their entireties.

TECHNICAL FIELD

The present invention relates to a pharmaceutical composition, a blood treatment device, a cosmetic product, and a food or drink product.

BACKGROUND ART

The World Health Organization (WHO) is warning that misuse and abuse of antibiotics have increased drug-resistant bacteria in the world, putting us in an extremely serious situation. To replace antibiotics for which drug-resistant bacteria are developed, medicinal drugs and quasi-drugs have been in demand with a mechanism in which drug-resistant bacteria cannot be developed. At the same time, measures for reducing the use of antibiotics are also necessary.

The use of antibiotics and the occurrence of drug-resistant bacteria are like playing a game of cat and mouse, and at some point there will be a limit to such chemical therapies. In fact, the U.S. Center for Disease Control and Prevention (CDC) reported on Mar. 5, 2013, the spread of carbapenem-resistant Enterobacteriaceae (CRE), in which carbapenem antibiotics, often used as a final option for the treatment of virulent infections, have failed.

Previously used medicinal drugs are chemical remedies as typified by, for example, antibiotics, low-molecular-weight drugs, anticancer drugs, and antiviral drugs. Although pathogen growth inhibitors or virus growth inhibitors are available, it is nearly impossible to find medicinal drugs that have a physical effect on the induction of tissue destruction of pathogens or viruses themselves. The side effects of anticancer drugs are also a great concern. Furthermore, there are no techniques or production methods for easily producing these previously used medicinal drugs. In addition to medicinal drugs, cosmetic products and food products are also required to have functions such as health maintenance and anti-aging.

Patent Literature 1 discloses a multilayered ceramic porous material characterized in 1) having an oxide ceramic layer on part of or the entire surface, 2) containing non-oxide ceramics in a portion other than the ceramic layer, and (3) having a three-dimensional mesh structure. This ceramic porous material is produced by compacting a mixture powder composed of two or more types of inorganic powders and subjecting the compacted body to a combustion synthesis reaction in air or in an oxidative atmosphere.

According to Patent Literature 1, the usage of the above ceramic porous material includes a filter, a catalyst or catalyst support, a sensor, a biomaterial, an antibacterial or antifouling material, an evaporator, a heat sink or heat exchanger, an electrode material, a semiconductor wafer suction plate, an adsorbent, a vent hole for gas release, a vibration control or sound-insulating material, a heating element, and the like.

Patent Literature 2 discloses a material for forming silver ion water comprising a porous ceramic obtained by combustion synthesis of a mixed raw material containing (1) at least one kind from among Ti and Zr, (2) Ag, and (3) at least one kind from among C, B, BN, and $B_4C$. According to Patent Literature 2, the usage of the thus produced silver ion water includes deodorization, sterilization, antibacterial, and the like.

However, Patent Literature 1 and Patent Literature 2 nowhere specifically disclose using porous ceramics in medicaments, cosmetic products, foods, or drinks.

Patent Literature 3 discloses an in vivo free-radical generator that is brought to target tissues to be treated, and that comprises silver ions supported on a carrier formed of an inorganic ion exchanger or an organic ion exchanger.

Patent Literature 4 discloses ion water for rinsing the oral cavity obtained by bringing a metal ion-antibacterial agent comprising antibacterial metal ions, such as zinc ions, silver ions, or copper ions, supported on an inorganic or organic carrier to contact with tap water or the like.

However, neither Patent Literature 3 nor Patent Literature 4 discloses an Example that uses a material produced by a combustion synthetic reaction as a carrier.

CITATION LIST

Patent Literature

PTL 1: JP2003-055063A
PTL 2: JP2006-066935A
PTL 3: WO 95/14484
PTL 4: JP5102749B

SUMMARY OF INVENTION

Technical Problem

As stated above, novel medicaments that are different from known medicaments such as antibiotics and anticancer drugs have been in demand. Further, there have been no techniques or production methods for easily producing known medicinal drugs.

Until now, almost no medicinal drugs have been developed for the purpose of preventing, inhibiting, or treating various types of diseases with a single type of medicinal drug. In fact, it is a standard idea to use several types of medicinal drugs for a single type of disease. However, if a single type of medicinal drug can be used alone in the prevention or treatment of various diseases, it is possible to avoid, for example, excessive effects and antagonistic effects, as well as serious side effects that accompany intake of multiple drugs.

Therefore, an object of the present invention is to provide a novel pharmaceutical composition (a) that can be easily produced, (b) that can be used for the treatment and/or prevention of multiple diseases, and (c) that is different from known antibiotics or anticancer drugs.

Solution to Problem

The present inventors found that a porous ceramic that is easily produced by using a combustion synthetic technique, which is a production method performed within a time period as short as several seconds to several minutes, can serve as a medicament that has an effect in the treatment and/or prevention of multiple diseases. The inventors also found that this porous ceramic is applicable to cosmetic products, as well as foods and drinks.

The present invention has been accomplished based on these findings and as a result of further research. The invention provides the following pharmaceutical composition, blood treatment device, cosmetic product, and food and drink products.

(I) Pharmaceutical Composition (I-1) A pharmaceutical composition comprising a porous ceramic obtained by combustion synthesis of a starting material comprising (1) titanium and (2) at least one member selected from the group consisting of carbon, boron, nitrogen, and silicon.

(I-2) The pharmaceutical composition according to (I-1), wherein the starting material further comprises at least one member selected from the group consisting of silver, gold, platinum, iron, and copper.

(I-3) The pharmaceutical composition according to (I-1) or (I-2), wherein the porous ceramic has a structure in which positive charge and negative charge are finely dispersed.

(I-4) The pharmaceutical composition according to any one of (I-1) to (I-3), wherein the porous ceramic comprises an oxide ceramic layer partially or entirely on the surface thereof.

(I-5) The pharmaceutical composition according to any one of (I-1) to (I-4), wherein the porous ceramic is a molded body or a ground material of the molded body.

(I-6) A pharmaceutical composition comprising a radical- and nanobubble-containing liquid.

(I-7) The pharmaceutical composition according to (I-6), wherein the radical- and nanobubble-containing liquid is obtained by bringing the porous ceramic of any one of (I-1) to (I-5) into contact with a liquid.

(I-8) The pharmaceutical composition according to any one of (I-1) to (I-7) for use in preventing and/or treating a symptom or disease selected from the group consisting of inflammatory intestinal diseases, cancers, neurodegenerative diseases, influenza virus infections, HIV infections, norovirus infections, sepsis, food poisoning, glycometabolism-related diseases, liver diseases, arteriosclerosis, hypertension, dyslipidemia, tuberculosis, obesity, skin diseases, stomatitis, acute alcohol poisoning, drunken sickness, hangover, anorexia, periodontosis, dental caries, endocarditis, myocardial infarction, cerebral infarction, constipation, diarrhea, spasm, and muscle pain.

(I-9) The pharmaceutical composition according to any one of (I-1) to (I-7), which is a disinfectant for at least one member selected from the group consisting of *Helicobacter pylori* bacteria, cavity-causing bacteria, periodontal bacteria, *tubercle bacillus, Escherichia coli*, enteropathogenic *Escherichia coli, Campylobacter* bacteria, dysentery *bacillus*, and viruses, or which is an antiflatulent or an antiviral agent.

(I-10) The pharmaceutical composition according to any one of (I-1) to (I-7) for use in preventing a reduction in the survival rate, improving the survival rate, or anti-aging in a lifetime from youth to old age.

(I-11) A method for preventing and/or treating a symptom or disease selected from the group consisting of inflammatory intestinal diseases, cancers, neurodegenerative diseases, influenza virus infections, HIV infections, sepsis, food poisoning, glycometabolism-related diseases, liver diseases, arteriosclerosis, hypertension, dyslipidemia, tuberculosis, obesity, skin diseases, stomatitis, acute alcohol poisoning, drunken sickness, hangover, anorexia, periodontosis, dental caries, endocarditis, myocardial infarction, cerebral infarction, constipation, diarrhea, spasm, and muscle pain, the method comprising administering an effective amount of the pharmaceutical composition of any one of (I-1) to (I-7).

(I-12) A method for eradicating at least one type of bacteria selected from the group consisting of *Helicobacter pylori* bacteria, cavity-causing bacteria, periodontal bacteria, tubercle *bacillus, Escherichia coli*, enteropathogenic *Escherichia coli, Campylobacter* bacteria, dysentery *bacillus*, and viruses, or a method for regulating intestinal functions, the method comprising administering an effective amount of the pharmaceutical composition of any one of (I-1) to (I-7).

(I-13) A method for preventing a reduction in the survival rate, improving the survival rate, or anti-aging in a lifetime from youth to old age, the method comprising administering an effective amount of the pharmaceutical composition of any one of (I-1) to (I-7).

(II) Blood Treatment Device (II-1) A blood treatment device comprising a blood flow channel for extracorporeal circulation of a patient's blood, wherein the blood flow channel is provided with the porous ceramic of any one of (I-1) to (I-5), and the porous ceramic and the blood are brought into contact with each other.

(III) Cosmetic Product (III-1) A cosmetic product comprising a porous ceramic obtained by combustion synthesis of a starting material comprising (1) titanium and (2) at least one member selected from the group consisting of carbon, boron, nitrogen, and silicon.

(III-2) The cosmetic product according to (III-1), wherein the starting material further comprises at least one member selected from the group consisting of silver, gold, platinum, iron, and copper.

(III-3) The cosmetic product according to (III-1) or (III-2), wherein the porous ceramic has a structure in which positive charge and negative charge are finely dispersed.

(III-4) The cosmetic product according to any one of (III-1) to (III-3), wherein the porous ceramic comprises an oxide ceramic layer partially or entirely on the surface thereof.

(III-5) The cosmetic product according to any one of (III-1) to (III-4), wherein the porous ceramic is a molded body or a ground material of the molded body.

(III-6) A cosmetic product comprising a radical- and nanobubble-containing liquid.

(III-7) The cosmetic product according to (III-6), wherein the radical- and nanobubble-containing liquid is obtained by bringing the porous ceramic of any one of (III-1) to (III-5) into contact with a liquid.

(III-8) The cosmetic product according to any one of (III-1) to (III-7) for use in moisturizing skin, inhibiting or preventing breath odor, or preventing or improving skin aging.

(III-9) A method for moisturizing skin, inhibiting or preventing breath odor, or preventing or improving skin aging, the method comprising administering the cosmetic product of any one of (III-1) to (III-7).

(IV) Food or Drink Product (IV-1) A food or drink product comprising a porous ceramic obtained by combustion synthesis of a starting material comprising (1) titanium and (2) at least one member selected from the group consisting of carbon, boron, nitrogen, and silicon.

(IV-2) The food or drink product according to (IV-1), wherein the starting material further comprises at least one member selected from the group consisting of silver, gold, platinum, iron, and copper.

(IV-3) The food or drink product according to (IV-1) or (IV-2), wherein the porous ceramic has a structure in which positive charge and negative charge are finely dispersed.

(IV-4) The food or drink product according to any one of (IV-1) to (IV-3), wherein the porous ceramic comprises an oxide ceramic layer partially or entirely on the surface thereof.

(IV-5) The food or drink product according to any one of (IV-1) to (IV-4), wherein the porous ceramic is a molded body or a ground material of the molded body.

(IV-6) A food or drink product comprising a radical- and nanobubble-containing liquid.

(IV-7) The food or drink product according to (IV-6), wherein the radical- and nanobubble-containing liquid is obtained by bringing the porous ceramic of any one of (IV-1) to (IV-5) into contact with a liquid.

(IV-8) A food or drink product according to any one of (IV-1) to (IV-7) for use in preventing or inhibiting aging, reducing body weight, recovering from fatigue (in particular, muscle fatigue), promoting metabolism of, for example, alcohol, stimulating appetite, or reducing a risk of dental caries and/or periodontosis.

(IV-9) A method for preventing or inhibiting aging, reducing body weight, recovering from fatigue (in particular, muscle fatigue), promoting metabolism of, for example, alcohol, stimulating appetite, or reducing a risk of dental caries and/or periodontosis, the method comprising administering an effective amount of the food or drink product of any one of (IV-1) to (IV-7).

Advantageous Effects of Invention

The pharmaceutical composition of the present invention, which comprises, as a main component, a porous ceramic comprising non-oxide ceramic, such as a carbide, a boride, a nitride, or a silicide, or a radical- and nanobubble-containing liquid, is a novel medicament that is different from known medicaments, such as antibiotics and anticancer drugs. The pharmaceutical composition of the present invention alone has therapeutic and prophylactic effects on several types of diseases and disorders. This porous ceramic is easily produced by using a combustion synthetic technique, i.e., a production method performed within a time period as short as several seconds to several minutes.

The use of the porous ceramic or the radical- and nanobubble-containing liquid as a cosmetic product achieves effects such as moisturizing skin, inhibiting and preventing breath odor, and inhibiting and improving skin aging.

Further, the use of the porous ceramic or the radical- and nanobubble-containing liquid as a food or drink product is expected to achieve effects such as preventing and inhibiting aging and obesity, reducing body weight, recovering from fatigue, such as muscle fatigue, promoting metabolism of, for example, alcohol due to increased blood flow, stimulating appetite, and reducing a risk of dental caries and/or periodontosis by reducing cavity-causing bacteria and periodontal bacteria.

In addition, the porous ceramic is highly safe because it is free of chronic toxicity, acute toxicity, and genetic toxicity.

BRIEF DESCRIPTION OF DRAWINGS

FIG. 4-1 illustrates the results of the measurement of radical species using an electron spin resonator.

FIG. 4-2 illustrates the results of the measurement of radical species using an electron spin resonator.

FIG. 5-1 illustrates correlations between the number of nanobubbles and the size of nanobubbles.

FIG. 5-2 illustrates correlations between the number of nanobubbles and the size of nanobubbles.

FIG. 5-3 illustrates correlations between the number of nanobubbles and the size of nanobubbles.

FIG. 5-4 illustrates correlations between the number of nanobubbles and the size of nanobubbles.

FIG. 8-1 is a graph illustrating the results of an in vitro test for growth inhibition on brain tumor cell line A172.

FIG. 8-2 is a graph illustrating the results of an in vitro test for growth inhibition on colorectal cancer cell line Colo 205.

FIG. 8-3 is a graph illustrating the results of an in vitro test for growth inhibition on leukemia cell line Jurkat.

FIG. 8-4 is a graph illustrating the results of an in vitro test for growth inhibition on stomach cancer cell line Kato III.

FIG. 8-5 is a graph illustrating the results of an in vitro test for growth inhibition on lung cancer cell line PC9.

FIG. 8-6 is a graph illustrating the results of an in vitro test for growth inhibition on liver cancer cell line Hep G2.

FIG. 15-1 is a graph illustrating the body weight, neutral fat, and heart weight of rats after intake of high-cholesterol food.

FIG. 15-2 shows photographs of dissected tissues of rats after intake of high-cholesterol food.

FIG. 15-3 shows a photograph of liver tissue of a rat of the control group.

FIG. 18-1 is a graph illustrating the total food consumption of each group of rats.

FIG. 18-2 is a graph illustrating the average food consumption of each group of rats (per rat per day).

FIG. 19-1 is a graph illustrating changes in the number of colonies of bacterium SA31 over time.

FIG. 19-2 is a graph illustrating changes in the number of colonies of bacterium SA31 over time (partially magnified version).

DESCRIPTION OF EMBODIMENTS

Figure 1:
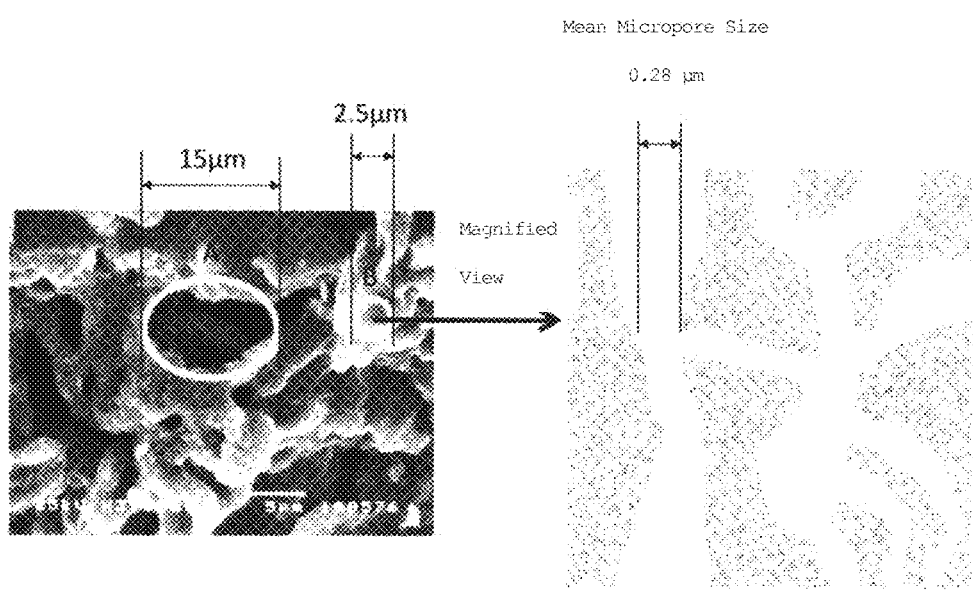
FIG. 1 illustrates the microstructure of a porous ceramic (formula (TC)) obtained by combustion synthesis.

The following describes the present invention in more detail.

The pharmaceutical composition, cosmetic product, and food and drink products of the present invention are characterized by comprising:
a porous ceramic obtained by combustion synthesis of a starting material comprising (1) titanium and (2) at least one member selected from the group consisting of carbon, boron, nitrogen, and silicon; or
a radical- and nanobubble-containing liquid.

The blood treatment device of the present invention is characterized by comprising a blood flow channel for extracorporeal circulation of a patient's blood. The blood flow channel is provided with the above porous ceramic, and the porous ceramic and the blood are brought into contact with each other.

In this specification, the terms "contain" and "comprise" also include the meanings of "essentially consist of" and "consist of."

Porous Ceramic

The feature of the porous ceramic contained in the pharmaceutical composition, cosmetic product, and food or drink product of the present invention (hereinafter sometimes referred to as the "porous ceramic of the present invention") is that it is obtained by combustion synthesis of a starting material comprising (1) titanium and (2) at least one member selected from the group consisting of carbon, boron, nitrogen, and silicon.

The starting material may be in the form of powder mixture, and is particularly preferably in the form of a molded body. To form a molded body, for example, well-known methods such as press molding or extrusion molding may be used. The shape and the size of molded body are not particularly limited, and may be designed in accordance with its application, the purpose of use, and the like. When component (2) is nitrogen gas, combustion synthesis may be performed in a state in which the powder is present in the gas. That is, the starting material in the present invention may be in a state such that titanium is present in a nitrogen atmosphere.

The mixing ratio of component (1) and component (2) above is not limited as long as combustion synthesis can be performed, and it may be suitably set according to, for example, the type of components used and the application of the final product. The weight ratio of component (1) to component (2), in terms of titanium:carbon-based component, is usually about 70 to 95 wt %:about 30 to 5 wt %, and preferably 75 to 89 wt %:25 to 11 wt %. Similarly, the weight ratio of component (1) to component (2), in terms of titanium:boron-based component, is about 60 to 90 wt %:about 40 to 10 wt %, and preferably 69 to 80 wt %:31 to 20 wt %. Further, the weight ratio of component (1) to component (2), in terms of titanium:nitrogen-based component, is about 70 to 95 wt %:about 30 to 5 wt %, and preferably 77 to 88 wt %:23 to 12 wt %. Furthermore, the weight ratio of component (1) to component (2), in terms of titanium:silicon-based component, is about 35 to 90 wt %:about 65 to 10 wt %, and preferably 47 to 80 wt %:53 to 20 wt %.

As component (2), carbon, boron, nitrogen, or silicon may be used alone as long as combustion synthesis can be performed. Alternatively, it is also possible to use, as component (2), a compound composed of any two or more of the following: carbon, boron, nitrogen, and silicon (e.g. silicon nitride, silicon carbide, boron nitride, or boron carbide).

The starting material may further comprise a component (component (3)), other than components (1) and (2), if necessary. Preferable examples of component (3) include silver, gold, platinum, iron, copper, and the like. These may be used alone or in a combination of two or more. The proportion of component (3) may be suitably set according to the type of component (3) and the like, and is usually about 1 to 50 wt %, and preferably 10 to 20 wt %, of the starting material.

As components (1), (2), and (3), different materials may be used separately, as long as combustion synthesis can be performed. Alternatively, as components (1), (2), and (3), a compound composed of components (1), (2), and (3) can also be used.

A combustion synthesis method is a production method in which a starting material is ignited locally to initiate a chemical reaction, and then, a chain reaction is allowed to proceed with heat of chemical reaction, the heat of which is released in the formation of a compound, thus yielding a reaction product within several seconds to several minutes. The method and operating conditions and the like of combustion synthesis reaction itself may be the same as those conventionally employed. For example, the reaction may be initiated by locally heating a starting material by ignition by, for example, electric discharge, laser irradiation, or a carbon heater. Once the reaction is initiated, the reaction proceeds due to a spontaneous exotherm to thus eventually obtain a target porous ceramic. The reaction time may be suitably set according to, for example, the size of starting material, but is usually about several seconds to several minutes. If component (3) is further mixed with the starting material in advance, it is possible to obtain a porous ceramic in which component (3) is finely dispersed.

The combustion synthesis reaction may be performed in a vacuum or in an inert atmosphere; however, it is desirable that the reaction be performed in air or in an oxidizing gas atmosphere. For example, a combustion synthesis reaction may be suitably performed in air at 0.1 atmospheres or higher (preferably 1 atmosphere or higher).

The porous ceramic of the present invention usually has a three-dimensional skeleton structure. The pores (communication holes), in particular, of the porous ceramic of the present invention are preferably through holes. The relative density of the porous ceramic of the present invention is not limited and may be suitably set. The relative density is usually preferably about 30 to 70%. The relative density or porosity may be controlled by, for example, the density of the molded body, as well as by the reaction temperature and atmospheric pressure for combustion synthesis. The micropore size distribution is usually about 0.1 to 30 µm.

When a combustion synthesis reaction is performed in the atmosphere (in air) or in an oxidizing atmosphere, it is possible to obtain a porous ceramic whose surface is formed of oxide ceramic while the inside is formed of non-oxide ceramic.

The form and size of the porous ceramic of the present invention are not limited, and may be designed in accordance with its application, the purpose of use, and the like. Examples of the form include discs, spherical, bars, plates, cylindrical, and the like. Examples of the form also include granules having a particle size of about several millimeters, as well as a powder of 0.5 to 100 µm (ground material) obtained by crushing the porous ceramic to such an extent that the porous shape is partly maintained. The crushing may be performed using a general-purpose grinder, such as a jaw crusher, a disc mill, an Orient mill, a rotating ball mill, a planetary ball mill, and a jet mill.

Even when titanium as component (1) is replaced with zirconium (Zr) or hafnium (Hf), which are elements in the same group of the periodic table (Group IV) as titanium, the same effects will be achieved. This can be theoretically explained based on the number of outermost shell electrons, which are involved in a chemical reaction. Resources of zirconium and hafnium, however, are available only small amounts, and a stable supply as a component of medicines, cosmetics, foods, or drinks is difficult.

When containing component (1) and component (2), the porous ceramic of the present invention may be produced by any one of the following reaction formulas (TC) to (TS), or a reaction formula in which these formulas are combined, i.e., by a combustion synthesis reaction by which the reaction product in the right-hand-side formula is continuously synthesized with heat of a chemical reaction, the heat of which is generated when the starting material powder mixture in the left-hand-side formula is ignited.

$$Ti+(1-X)C \rightarrow TiC_{1-X} \quad 0 \leq X \leq 0.4 \qquad \text{formula (TC)}$$

$$Ti+(2-X)B \rightarrow XTiB+(1-X)TiB_2 \quad 0 \leq X \leq 1 \qquad \text{formula (TB)}$$

$$2Ti+(1-X)N_2 \rightarrow 2TiN_{1-X} \quad 0 \leq X \leq 0.4 \qquad \text{formula (TN)}$$

$$5Ti+(3+7X)Si \rightarrow 5XTiSi_2+(1-X)Ti_5Si_3 \quad 0 \leq X \leq 1 \qquad \text{formula (TS)}$$

When a combustion synthesis is carried out in air or in an oxidizing gas atmosphere in accordance with any one of the reaction formulas (TC) to (TS), or a reaction formula in which these formulas are combined, a porous ceramic is obtained in which only the surface layer of the non-oxide ceramic, i.e., the main phase of reaction product, is reacted with oxygen to thus slightly form a thermodynamically stable oxide ceramic layer. The obtained porous ceramic is a reaction product represented by any one of the following formulas (TOC) to (TOS), or a reaction product represented by a formula in which these formulas are combined.

$$(1-Z)TiC_{1-X}+ZTiO_{2-X}$$

$$0 \leq X \leq 0.4, \ 0 \leq Z \leq 0.4 \qquad \text{formula (TOC)}$$

$$(1-Z)(XTiB+(1-X)TiB_2)+ZTiO_{2-X}$$

$$0 \leq X \leq 1, \ 0 \leq Z \leq 0.4 \qquad \text{formula (TOB)}$$

$$(1-Z)TiN_{1-X}+ZTiO_{2-X}$$

$$0 \leq X \leq 0.4, \ 0 \leq Z \leq 0.4 \qquad \text{formula (TON)}$$

$$(1-Z)(5XTiSi_2+(1-X)Ti_5Si_3)+ZTiO_{2-X}$$

$$0 \leq X \leq 1, \ 0 \leq Z \leq 0.4 \qquad \text{formula (TOS)}$$

When containing components (1) to (3), the porous ceramic of the present invention may be produced by any one of the following reaction formulas (TCM) to (TSM), or a reaction formula in which these formulas are combined, i.e., by a combustion synthesis reaction by which the reaction product in the right-hand side formula is continuously synthesized with heat of a chemical reaction, the heat of which is generated when the starting material powder mixture is ignited. In the formulas, M represents at least one metals from among silver, gold, platinum, iron, and copper, or an alloy of these metals.

$$(1-Y)(Ti+(1-X)C)+YM \rightarrow (1-Y)TiC_{1-X}+YM$$

$$0 \leq X \leq 0.4, \ 0 < Y \leq 0.4 \qquad \text{formula (TCM)}$$

$$(1-Y)(Ti+(2-X)B)+YM \rightarrow (1-Y)(XTiB+(1-X)TiB_2)+YM$$

$$0 \leq X \leq 1, \ 0 < Y \leq 0.4 \qquad \text{formula (TBM)}$$

$$(1-Y)(2Ti+(1-X)N_2)+YM \rightarrow 2(1-Y)TiN_{1-X}+YM$$

$$0 \leq X \leq 0.4, \ 0 < Y \leq 0.4 \qquad \text{formula (TNM)}$$

$$(1-Y)(5Ti+(3+7X)Si)+YM \rightarrow (1-Y)(5XTiSi_2+(1-X)Ti_5Si_3)+YM$$

$$0 \leq X \leq 1, \ 0 < Y \leq 0.4 \qquad \text{formula (TSM)}$$

When a combustion synthesis is carried out in air or in an oxidizing gas atmosphere in accordance with any one of the reaction formulas (TCM) to (TSM), or a reaction formula in which these formulas are combined, a porous ceramic is obtained in which only the surface layer of the non-oxide ceramic, i.e., the main phase of reaction product, is reacted with oxygen to thus slightly form a thermodynamically stable oxide ceramic layer. The obtained porous ceramic is a reaction product represented by any one of the following formulas (TOCM) to (TOSM), or a reaction product represented by a formula in which these formulas are combined.

$$(1-Z)((1-Y)TiC_{1-X}+YM)+ZTiO_{2-X}$$

$$0 \leq X \leq 0.4, \ 0 < Y \leq 0.4, \ 0 \leq Z \leq 0.4 \qquad \text{formula (TOCM)}$$

$$(1-Z)((1-Y)(XTiB+(1-X)TiB_2)+YM)+ZTiO_{2-X}$$

$$0 \leq X \leq 1, \ 0 < Y \leq 0.4, \ 0 \leq Z \leq 0.4 \qquad \text{formula (TOBM)}$$

$$(1-Z)(2(1-Y)TiN_{1-X}+YM)+ZTiO_{2-X}$$

$$0 \leq X \leq 0.4, \ 0 < Y \leq 0.4, \ 0 \leq Z \leq 0.4 \qquad \text{formula (TONM)}$$

$$(1-Z)((1-Y)(5XTiSi_2+(1-X)Ti_5Si_3)+YM)+ZTiO_{2-X}$$

$$0 \leq X \leq 1, \ 0 < Y \leq 0.4, \ 0 \leq Z \leq 0.4 \qquad \text{formula (TOSM)}$$

The following reaction formulas (BN) to (OBNM) or the reaction products of these formulas are with respect to when boron nitride is used as component (2). In the formulas, M represents at least one or more metals of silver, gold, platinum, iron, and copper, or an alloy of these metals.

$$(3-X)Ti+2(1-X)BN \rightarrow (1-X)TiB_2+2TiN_{1-X}$$

$$0 \leq X \leq 0.4 \qquad \text{formula (BN)}$$

$(1-Y)((3-X)Ti+2(1-X)BN)+YM \rightarrow (1-Y)((1-X)TiB_2+2TiN_{1-X})+YM$ $0 \leq X \leq 0.4, 0 < Y \leq 0.4$ formula (BNM)

$(1-Z)((1-X)TiB_2+2TiN_{1-X})+ZTiO_{2-X}$ $0 \leq X \leq 0.4, 0 \leq Z \leq 0.4$ formula (OBN)

$(1-Z)((1-Y)((1-X)TiB_2+2TiN_{1-X})+YM)+ZTiO_{2-X}$ $0 \leq X \leq 0.4, 0 < Y \leq 0.4, 0 \leq Z \leq 0.4$ formula (OBNM)

Radical- and Nanobubble-Containing Liquid

The pharmaceutical composition, cosmetic product, and food or drink product of the present invention is characterized by comprising a radical- and nanobubble-containing liquid.

This liquid is not limited, as long as the liquid can produce radicals and nanobubbles and as long as the liquid can be used in pharmaceutical compositions, cosmetic products, food products, and drink products. Examples include water, aqueous solutions, and the like. Specific examples include distilled water, pure water, ultrapure water, tap water, well water, mineral water, injectable solutions, infusions, physiological saline, buffer solutions, and the like.

The radicals (free radicals) are not particularly limited, as long as the effects of the present invention are obtained. They are preferably hydroxyl radicals (.OH), carbon radicals (.C), and methyl radicals (.$CH_m$, $1 \leq m \leq 3$), and more preferably hydroxyl radicals and methyl radicals. The radicals may either be of one type or two or more types.

The diameter distribution of nanobubbles is desirably within a range of 10 to 500 nm, and preferably 10 to 100 nm. The number of bubbles contained in the liquid is preferably 1 million to 100 million nanobubbles/mL, and more preferably 5 million to 50 million nanobubbles/mL.

The radical- and nanobubble-containing liquid may be produced by bringing the porous ceramic of the present invention into contact with the liquid. The ratio of the porous ceramic of the present invention to the liquid is not particularly limited, and may be suitably set. In general, the amount of the porous ceramic of the present invention may be suitably set from the range of about 0.01 mg to 100 g per liter of liquid. The porous ceramic of the present invention and the liquid may be mixed with each other at an ordinary temperature. It is possible to stir the mixture, if necessary.

At the time of mixing the porous ceramic of the present invention with the liquid, it is desirable to perform ultrasonic irradiation. The ultrasonic irradiation can more effectively facilitate the generation of radicals. The ultrasonic irradiation may be performed using a known device.

To remove the porous ceramic from the radical- and nanobubble-containing liquid, a filtration separation method may be performed with the use of a general-purpose filter or the like. Further, considering that it is possible to produce a porous ceramic containing a uniform fine distribution of iron or other magnetic bodies, after a radical- and nanobubble-containing liquid is produced by using such a magnetic porous ceramic, the magnetic porous ceramic may be removed by adsorption separation using magnet or the like.

Combustion synthesis using heat of chemical reaction, the heat of which is generated at the time of compound synthesis, produces a porous ceramic by rapid heating up to 2500 to 3500° C. and rapid cooling. Porous ceramics that are synthesized at a high speed with rapid temperature changes have a feature such that lattice defects remain frozen as a result of having no time to spare for alleviating the lattice defects. The resulting product is thus a lattice-defect-containing non-uniform product in which electron holes (holes) and electrons are partially localized. It is a well-known fact that heating of metal or the like produces thermoelectronic emission from the metal surface. Although this is not intended to be binding to any theory, the electric field generated by a potential difference resulting from the localization in the porous ceramic is considered to be a cause of the radical-generating mechanism. This is a phenomenon specific to combustion synthesis, and it is impossible to produce electron holes (holes) and electrons that are partially localized in a uniform ceramic sintered body as above.

As described above, the porous ceramic of the present invention, which is a combustion-synthesis material, has characteristics different from those of ceramic sintered bodies, and the effects of the present invention are achieved presumably based on the characteristics of a combustion-synthesis material. However, it is difficult to accurately analyze such characteristics, and it is thus difficult to directly define the porous ceramic of the present invention by its structure or characteristics.

Also, it is fundamentally difficult to directly define the radical- and nanobubble-containing liquid by its structure or characteristics since the radical lifetime is said to be about several microseconds to several seconds, and the amount of radicals greatly change over time.

Combustion synthesis is a production method that effectively uses an exothermic reaction that occurs when a compound is produced from a starting material, and the obtained porous ceramic has electrical characteristics different from those of ceramics obtained through typical synthesis methods. Rapid heating up to 3000° C. and rapid cooling occur on a second-to-second basis, which is believed to generate lattice defects and distortion in the crystal structure. Consequently, while maintaining electroneutrality as a whole, localized electric fields are believed to be generated, producing a polarization compound that achieves a finely dispersed distribution of positive charge and negative charge. Although it is difficult to directly measure such an electrical characteristic, proof is provided by the results of the following indirect experiments.

Observation under an optical microscope of a suspension obtained by dispersing the porous ceramic powder of the present invention in water revealed that powder particles that have a particle size of 100 μm or less were moving, e.g., rotating and travelling. This may be physically understood by considering polarized particles to receive electric power from surrounding particles, which allows them to move in a complicated manner. Also, some powder particles were bonded together. This is presumably because electrically opposite powder particles were electrically attracted when being close to each other and thus bonded together.

Pharmaceutical Composition

The pharmaceutical composition of the present invention is characterized by comprising the porous ceramic or radical- and nanobubble-containing liquid described above.

The pharmaceutical composition of the present invention is administered to mammals, including humans.

To prepare the pharmaceutical composition, the porous ceramic or radical- and nanobubble-containing liquid may be used as is, or mixed with a pharmaceutically acceptable non-toxic carrier, diluent, or excipient, and formed into tablets (including uncoated tablets, sugar-coated tablets, effervescent tablets, film-coated tablets, chewable tablets, troches, etc.), capsules, pills, powders (powdered drugs), granules, fine granules, liquids, emulsions, suspensions, syrups, pastes, injectable agents (including preparations formulated into liquids by admixture into distilled water or an infusion, such as an amino acid infusion or an electrolyte infusion, at the time of use), candies, gums, dentifrices, Table 1 shows a summary of examples of usages of the pharmaceutical composition, the usage of which is believed to be suitable for each major disease.

TABLE 1

Examples of usage of the pharmaceutical composition according to disease

|  |  | Oral administration | | | Administration into blood | | Blood |
|---|---|---|---|---|---|---|---|
|  |  | Liquid | Tablet, troche, candy | Gum, toothpaste | Injection | Drip infusion, infusion | treatment Blood circulation |
| Cavity-causing bacteria | For treatment | ✓ | ✓ | ✓ | ✓ | ✓ | ✓ |
| Periodontal bacteria | For prevention | ✓ | ✓ | ✓ |  |  |  |
| Helicobacter pylori | For treatment |  | ✓ | ✓ |  |  |  |
|  | For prevention | ✓ | ✓ | ✓ |  |  |  |
| Dementia | For treatment |  |  |  | ✓ | ✓ | ✓ |
|  | For prevention | ✓ | ✓ | ✓ |  |  |  |
| Cancer | For treatment |  |  |  | ✓ | ✓ | ✓ |
|  | For prevention | ✓ | ✓ | ✓ |  |  |  |
| Virus | For treatment BSL2 | ✓ | ✓ | ✓ | ✓ | ✓ |  |
|  | For treatment BSL3 |  |  |  | ✓ | ✓ | ✓ |
|  | For treatment BSL4 |  |  |  | ✓ | ✓ | ✓ | sheets, ointments, injectable solutions, infusions, dentifrices, gargling agents, atomization inhaler, sprays, and the like, to obtain a pharmaceutical formulation for medicaments.

The content of the porous ceramic in the pharmaceutical composition of the present invention may be suitably selected from the range of $10^{-7}$ to 100 wt %, preferably 0.01 to 99.9 wt %, and more preferably 0.1 to 99 wt %, of the total amount of the pharmaceutical composition.

The content of the radical- and nanobubble-containing liquid in the pharmaceutical composition of the present invention may be suitably selected from the range of $10^{-8}$ to 100 percent by volume, preferably 0.001 to 99.9 percent by volume, and more preferably 0.01 to 99 percent by volume, of the total amount of the pharmaceutical composition.

The method for administration of the pharmaceutical composition of the present invention may be any general-purpose administration method, and oral administration and parenteral administration may both be used. Examples of usable parenteral administration include administration into blood, direct administration to disease sites, intramuscular administration, subcutaneous administration, and the like. For parenteral administration for respiratory diseases, pulmonary administration by, for example, atomization inhalation using a nebulizer or the like may be used. It is also possible to use nasal administration to nasal mucosa such as the nasal cavity; transdermal administration through skin absorption or the like; and the like. It is also possible to directly attach a sheet containing the pharmaceutical composition to a disease site.

The dosage of the pharmaceutical composition of the present invention is suitably determined according to various conditions, such as the patient's body weight, age, gender, and symptoms.

The pharmaceutical composition of the present invention is effective in preventing and/or treating symptoms and diseases selected from the group consisting of inflammatory intestinal diseases (e.g., Crohn's disease and ulcerative colitis), cancers (e.g., stomach cancer, rectal cancer, colon cancer, hepatic cancer, pancreatic cancer, pulmonary cancer, pharyngeal cancer, esophageal cancer, renal cancer, gallbladder and bile duct cancer, head and neck cancer, bladder cancer, prostate cancer, breast cancer, uterine cancer, ovarian cancer, brain cancer, and leukemia), neurodegenerative diseases (e.g., polyglutamine disease, Alzheimer's disease, Parkinson's disease, and amyotrophic lateral sclerosis), influenza virus infections, HIV (human immunodeficiency virus) infections, norovirus infections, sepsis, food poisoning, glycometabolism-related diseases (e.g., diabetes, hyperglycemia, impaired glucose tolerance, and insulin resistance syndrome), liver diseases (e.g., fatty liver, hepatitis, and cirrhosis), arteriosclerosis, hypertension, dyslipidemia, tuberculosis, obesity, skin diseases (e.g., psychosomatic skin diseases, tinea pedis, inflammatory skin diseases, and atopic dermatitis), stomatitis, acute alcohol poisoning, drunken sickness, hangover, anorexia, periodontal diseases, dental caries, endocarditis, myocardial infarction, cerebral infarction, constipation, diarrhea, spasm, and muscle pain.

The pharmaceutical composition of the present invention may also be used as a disinfectant for at least one member selected from the group consisting of *Helicobacter pylori* bacteria, cavity-causing bacteria, periodontal bacteria, *tubercle bacillus*, *Escherichia coli*, enteropathogenic *Escherichia coli* (in particular, enterohemorrhagic *E. coli*, such as O-157), *Campylobacter* bacteria, dysentery *bacillus*, and viruses (in particular, influenza viruses, HIVs, and noroviruses), or as an antiflatulent or an antiviral agent.

The pharmaceutical composition of the present invention may also be used for preventing a reduction in the survival rate, improving the survival rate, or anti-aging in a lifetime from youth to old age.

Medicaments comprising a ceramic as a main component have few precedents, and existing medicaments comprising a ceramic are limited to those comprising an oxide ceramic. In contrast, the present invention uses a porous ceramic comprising a non-oxide ceramic, such as carbide, boride, and nitride, as a main component, or a radical- and nanobubble-containing liquid obtained by bringing the porous ceramic of the present invention into contact with a liquid.

Although this is not intended to be binding to any theory, the present invention is believed to be based on physical therapy in which pathogens, viruses, and cancer cells themselves are reduced or killed through tissue destruction, metabolism inhibition, growth inhibition, or the like, rather than based on a chemical therapy using antibiotics, low-molecular weight medicinal drugs, anticancer drugs, antiviral drugs, or the like. Therefore, it is expected that resistant bacteria as a result of heavy use of antibiotics will not be developed, that the pharmaceutical effect will be achieved on various viruses, pathogens, cancer cells, and the like, irrespective of the type, and that at the same time, the amount of antibiotics used will be reduced.

In addition to thus far predominant low-molecular-weight drugs, antibacterial drugs, antibiotics, antiviral drugs, and antitumor substances, the development of antibody drugs, nucleic acid drugs, regeneration-inducing drugs, and the like has currently been progressing. However, these drugs are all for limited diseases only, and none of them can serve as a preventive agent, an inhibitor, or a therapeutic agent that can be used alone for a wide range of diseases and disorders, as in the pharmaceutical composition of the present invention.

The pharmaceutical composition of the present invention is effective in prophylaxis and/or treatment in fields of various diseases, such as inflammation diseases, digestive organ system diseases, mouth organ diseases, circulatory system diseases, malignant neoplastic diseases, immune system diseases, neurological system diseases, respiratory system diseases, lifestyle-related diseases, dermal diseases, and viruses.

The pharmaceutical composition of the present invention is effective against *Campylobacter* bacteria, enterohemorrhagic *E. coli* O-157, and dysentery *bacillus*, which cause food poisoning. The pharmaceutical composition of the present invention is capable of inactivating viruses irrespective of their types, such as noroviruses, which are representative of non-enveloped types, and influenza viruses and HIV, which are representative of enveloped types. Accordingly, the effect is achieved against bacteria and viruses, and thus, it is also effective to administer into blood an aqueous solution that has been contacted with the porous ceramic of the present invention to treat sepsis.

The pharmaceutical composition of the present invention is also effective in directly decomposing acetaldehyde. In the liver, after drinking alcohol, alcohol dehydrogenase (ADH) converts the alcohol ($CH_3CH_2OH$) to acetaldehyde ($CH_3CHO$), and then acetaldehyde dehydrogenase (ALDH) metabolizes acetaldehyde to harmless acetic acid ($CH_3COOH$). Thereafter, acetic acid is converted into carbon dioxide ($CO_2$) and water ($H_2O$) to be discharged to the outside of the body. Among the above, ALDH consisting of 517 amino acids is one type of protein, and exhibits three genetic polymorphisms according to the difference in base sequences. The metabolic ability of ALDH of the AG type is only about 1/16 of that of the GG type, and the AA type has no metabolic ability. According to this fact, the types are classified as follows: the GG type can drink a lot of alcohol, the AG type cannot drink much alcohol, and the AA type cannot drink alcohol. Acetaldehyde is highly toxic and causes headache, vomiting, drunken sickness, and hangover. For the AA type, acetaldehyde is extremely dangerous since it remains inside the body for a long time. Acetaldehyde is not only produced from ingested alcohol but is also contained in the smoke of tobacco and is noted as a carcinogenic substance. A recent study revealed that acetaldehyde is also contained in expired air since tongue plaque produces acetaldehyde. The World Health Organization has reported that long-time exposure to acetaldehyde poses a risk of cancer even at a physiological concentration of 6.1 to 36.1 ppb (low concentration). Long-term, continuous exposure to acetaldehyde produced from tongue plaque is harmful.

In view of the above, changes in the concentration of acetaldehyde in expired air were measured before and after oral intake of an aqueous solution that has been brought into contact with the porous ceramic of the present invention, or a powder of the porous ceramic of the present invention. The results showed a significant reduction after the intake, which confirmed the decomposition of acetaldehyde (see the Test Examples). Although the mechanism of action is unknown, it is believed that radicals are generated when the porous ceramic of the present invention is brought into contact with an aqueous solution such as saliva, and these radicals function in a manner similar to that of ALDH to decompose acetaldehyde. In any event, continuous oral intake of an aqueous solution that has been brought into contact with the porous ceramic of the present invention or the porous ceramic powder makes it possible to reduce tongue plaque, and reduce the generation of acetaldehyde from tongue plaque. Accordingly, it is revealed that the porous ceramic of the present invention has the ability to decompose acetaldehyde, which is considered to be one of the causative substances of cancer, and continuous oral intake thus can serve as a prevention of cancer.

This ability to decompose acetaldehyde is applicable to medical use in the treatment of acute alcohol poisoning by oral administration or administration into blood to directly decompose acetaldehyde.

The pharmaceutical composition of the present invention is effective in removing plaque in the oral cavity, and is also effective antibacterially in the oral cavity. In home-visit dental care, it is difficult to keep clean the oral cavities of the elderly, in particular, those bedridden. Although current therapeutic methods involve sterilization with non-toxic low-concentration hypochlorous acid, there is considerable room for improvement in terms of safety and long-term sterilization maintenance. Specifically, a drug that is as safe as food, can be used daily, is effective in plaque removal, and has an antibacterial effect, has been in demand.

Therefore, a clinical test was performed that involves gargling three times per day using processed water that had been brought into contact with the porous ceramic of the present invention. As a result, almost all the test subjects showed a decrease in the plaque index obtained by scoring the plaque formation rate, which confirmed that the processed water inhibited plaque formation (see the Test Example). Characteristics of the clinical test were that tooth brushing using a toothpaste was not forbidden, and everyday life activities were performed as usual. Although it is natural that the index of the subjects who are not good at tooth brushing (having a plaque index of 2 or more) decreased, the index of the subjects who are good at tooth brushing (having a plaque index of 1 or less) also decreased. Accordingly, the use of the processed water makes it possible to remove dental plaque in a portion where it is difficult for a tooth brush to reach.

At the same time, the bacterial count in the oral cavity was also analyzed. As a result, the average bacterial count 1 week after gargling with tap water increased to about 170%, whereas the average bacterial count 1 week after gargling with the processed water decreased to about 60%. These results revealed that an antibacterial effect was achieved simultaneously with dental plaque removal, and that the use of the processed water is useful for oral care for bedridden elderly people who find it difficult to brush their teeth.

The pharmaceutical composition of the present invention is also effective for atopic dermatitis. Although atopic dermatitis, in which dry skin and dermatitis repeatedly occur, has been considered to be one type of autoimmune disease, a recent study based on a mouse experiment confirmed that the inflammation occurs as a result of an imbalance of resident microbiota caused by an overgrowth on the skin of multiple bacteria, including *Staphylococcus aureus*. At present, treatment methods for this disease include, for example, a method for inhibiting inflammation using steroids. Long-term heavy use of steroids, however, may cause side effects such as compromised disorders, steroid osteoporosis, steroid diabetes, steroid ulcers, and swelling (moon face), and therapeutic agents for atopic dermatitis that cause no side effects were in demand. Processed water obtained by adding the porous ceramic molded body of the present invention, and a suspension obtained by adding a powder of the porous ceramic exhibit a strong antibacterial effect, and thus serve as a candidate for a therapeutic agent for dermatitis that causes no side effects.

Blood Treatment Device

The blood treatment device of the present invention is characterized by comprising a blood flow channel for extracorporeal circulation of a patient's blood. The blood flow channel is provided with the porous ceramic of the present invention, and the porous ceramic and the blood are brought into contact with each other.

In the blood treatment device of the present invention, the blood flow channel is composed of a tube provided with a pump, and a column connected to the tube. When the pump is operated, the blood circulates through the blood flow channel. The column is filled with the porous ceramic of the present invention, and when the blood is brought into contact with the porous ceramic, the following effects are expected to be achieved in the blood: sterilization of bacteria, inactivation of viruses, disruption of cancer cells, and decomposition of, for example, unnecessary waste proteins and abnormal RNAs to make them harmless. The structure of the porous ceramic with which the column is filled is not particularly limited, and may be, for example, a molded body, a powder, or a sheet comprising the powder, as long as the blood can come into direct contact with the porous ceramic.

Cosmetic Product

The cosmetic product of the present invention is characterized by comprising the porous ceramic or the radical- and nanobubble-containing liquid.

The cosmetic product as used in the present invention includes any cosmetic product that is applicable to the skin, body hair, mucous membranes, head hair, nails, teeth, scalp, facial skin, lips, and the like of animals (including humans).

The content of the porous ceramic in the cosmetic product of the present invention may be suitably selected from the range of $10^{-7}$ to 100 wt %, preferably 0.01 to 99.9 wt %, and more preferably 0.1 to 99 wt %, of the total amount of the cosmetic product.

The content of the radical- and nanobubble-containing liquid in the cosmetic product of the present invention may be suitably selected from the range of $10^{-8}$ to 100 percent by volume, preferably 0.001 to 99.9 percent by volume, and more preferably 0.01 to 99 percent by volume, of the total amount of the cosmetic product.

In addition to the porous ceramic or radical- and nanobubble-containing liquid, components that are usually used for cosmetics may also be appropriately incorporated into the cosmetic product of the present invention, if necessary. Examples of such components include skin-whitening agents, antioxidants, oil components, humectants, ultraviolet absorbers, surfactants, thickeners, alcohols, colorants, aqueous components, powder components, water, various skin nutrients, and the like.

The dosage form of the cosmetic product of the present invention may be selected from a wide range, including an aqueous solution form, solubilized form, emulsion form, powder form, oil form, gel form, ointment form, aerosol form, water-oil bilayer form, water-oil-powder trilayer form, and the like.

The cosmetic product of the present invention may also be used for any purpose of use. Examples of such uses include basic cosmetic products, such as facial washes, skin lotions, milky lotions, serums, creams, gels, essences, packs, and masks; make-up cosmetic products, such as foundations, lipsticks, blushes, eyeliners, eye shadows, and mascaras; nail cosmetic products, such as nail polishes, base coats, top coats, and nail-polish removers; and other products such as facial washes, dentifrices (paste or liquid), mouthwashes, cleansing agents, massaging agents, after-shave lotions, pre-shave lotions, shaving creams, body soaps, soaps, shampoos, rinses, hair treatments, hair dressings, hair growing agents, hair tonics, antiperspirants, and bath agents.

The cosmetic product of the present invention is expected to exhibit effects such as moisturizing skin, inhibiting and preventing breath odor, and inhibiting and improving skin aging.

The pharmaceutical composition and cosmetic product of the present invention also encompass quasi-drugs.

Food and Drink Products

The food and drink products of the present invention are characterized by comprising the porous ceramic or radical- and nanobubble-containing liquid. The food and drink products of the present invention encompass any food and drink products that are edible for humans, and also encompass feed for animals and feed for fish.

The porous ceramic of the present invention is thermally and chemically stable due to covalency. Thus, even if food containing the porous ceramic is cooked by heating, no chemical change, dissolution, elution, modification, or the like will occur, and its intake efficacy will be maintained.

To prepare the food and drink products of the present invention, the porous ceramic or radical- and nanobubble-containing liquid may be used without further processing, or may be optionally mixed with minerals, vitamins, flavonoids, quinones, polyphenols, amino acids, nucleic acids, essential fatty acids, fresheners, binders, sweeteners, disintegrators, lubricants, coloring agents, fragrances, stabilizing agents, preservatives, sustained-release regulators, surfactants, solubilizers, wetting agents, and the like.

The type of food or drink product according to the present invention is not particularly limited. Examples include dairy products; fermented foods (e.g., yogurt); beverages (e.g., juices, coffee, black tea, green tea, and like soft drinks, carbonated drinks, milk beverages, lactic-acid-bacteria beverages, drinks containing lactic acid bacteria, yogurt drinks, Japanese sake, Western wines and spirits, fruit wines, and like liquors); spreads (e.g., custard cream); pastes (e.g., fruit pastes); confectioneries (e.g., gum, candies, troches, chocolate, doughnuts, pies, cream puffs, jelly, cookies, cakes, pudding, and pancakes); frozen desserts (e.g., ice cream, ice candies, and sherbets); foods (e.g., bread, curry, soup, meat sauce, pasta, pickles, jam, and tofu); seasonings (e.g., dressing, tasty seasonings, and soup bases); and the like.

The method for producing the food or drink product of the present invention is also not particularly limited. The food or drink product of the present invention can be suitably produced in accordance with known methods. For example, the porous ceramic or radical- and nanobubble-containing liquid may be mixed with or sprayed onto an intermediate or final product obtained in a process for producing the food and drink products mentioned above, thereby obtaining a food or drink product of the present invention.

Further, the food or drink product of the present invention may also be used as a health food, nutritional composition, functional food, food with function claims, nutraceutical, supplement (e.g., dietary supplement), food for health uses, or food for specified health uses. The dosage unit form for use as a supplement is not particularly limited, and can be suitably selected. Examples of such dosage forms include tablets, capsules, granules, liquids, powders, and the like.

The content of the porous ceramic in the food or drink product of the present invention may be suitably selected from the range of $10^{-7}$ to 100 wt %, preferably 0.01 to 99.9 wt %, and more preferably 0.1 to 99 wt %, of the total amount of the food or drink product.

The content of the radical- and nanobubble-containing liquid in the food or drink product of the present invention may be suitably selected from the range of $10^{-8}$ to 100 percent by volume, preferably 0.001 to 99.9 percent by volume, and more preferably 0.01 to 99 percent by volume, of the total amount of the food or drink product.

The amount of intake of the food or drink product of the present invention may be suitably set according to various conditions, such as the consumer's body weight, age, gender, and symptoms.

The food and drink products of the present invention are expected to exhibit effects such as biological self-healing, improving survival rate, preventing and inhibiting aging and obesity, reducing body weight, recovering from fatigue (in particular, muscle fatigue), promoting metabolism of, for example, alcohol due to increased blood flow, and stimulating appetite. Additionally, the food and drink products of the present invention are capable of reducing periodontal bacteria and cavity-causing bacteria, and are thus also expected to exhibit an effect of preventing various diseases associated with these bacteria (e.g., dental caries and periodontal disease).

When various foods containing the porous ceramic of the present invention are taken, direct decomposition of acetaldehyde is synergistically performed in addition to enzymatic decomposition, preventing drunken sickness and hangover. A curcumine component contained in, for example, commercially available turmeric improves the acetaldehyde decomposition rate by activating the metabolism of the liver; theoretically, however, no effect is produced on the AA type, which inherently does not have ALDH. In contrast, the intake of an aqueous solution that has been brought into contact with the porous ceramic of the present invention or the porous ceramic powder of the present invention leads to direct decomposition of acetaldehyde with or without the presence of acetaldehyde-metabolizing enzymes. Thus, the effect is produced even on the AA type, which does not have ALDH.

Noroviruses, which are highly likely to cause secondary infection, are resistant to alcohol, and must thus be sterilized using hypochlorous acid water or by cooking with heat. Although the use of hypochlorous acid water, cooking with heat, and other means are effective for raw foods, such as sliced raw fish or oysters, it is impossible to avoid deterioration of the food quality. In contrast, the porous ceramic of the present invention is odorless and tasteless; thus, if processed water that has been brought into contact with the porous ceramic is sprayed onto or applied to raw food, such as sliced raw fish, it is possible to perform sterilization, and destroy or inhibit the growth of bacteria without deteriorating the food quality. Accordingly, the processed water is expected to be used as a fungicide or an antibacterial agent that is safe and harmless even if eaten.

The food and drink products of the present invention also encompass those for livestock. The average mortality rate of calves in the first year of life is said to be about 10%. This is because calves that develop diarrhea loose physical strength, and thus easily catch a disease. Lowering this mortality rate is important in livestock management. When processed water that had been brought into contact with the porous ceramic of the present invention was continuously given to calves, the mortality rate of calves in their first year of life became substantially 0%. Accordingly, the use of the processed water as drinking water for livestock makes it possible to improve the survival rate.

In addition, as shown in the Test Examples, the porous ceramic of the present invention is highly safe, showing no chronic toxicity, acute toxicity, or genetic toxicity.

EXAMPLES

The present invention is described in more detail below with reference to Examples. However, the present invention is not limited to these Examples.

Production Example 1: Formula (TC)

A powder having a mean particle size of 45 μm was used as a titanium starting material. A carbon powder having a primary particle size of 0.1 μm or less was granulated to obtain granules having a secondary particle size of about 1 mm, and used as a carbon starting material. The titanium starting material and the carbon starting material were weighed so that the weight ratio was 0.8:0.2, and the resulting mixture was sufficiently mixed by stirring to be used as a starting material. The resulting starting material was press-molded into a cylindrical shape having a diameter of 20 mm and a height of 20 mm, thereby obtaining a green compact having a relative density of 50%. When a portion at the upper surface of the obtained green compact was ignited by laser in an argon atmosphere, a series of combustion waves was formed, and the combustion synthesis was completed within about 4 seconds. After being allowed to cool, the reaction product was collected, and the crystalline layer was identified with a powder X-ray diffractometer, which revealed that the principal component was titanium carbide ($TiC_{1-x}$). In this manner, a porous ceramic molded body of titanium carbide represented by formula (TC) was produced.

Production Example 2: Formula (TOC)

When a portion of the upper surface of the same green compact as in Production Example 1 was ignited by electric discharge in air, a series of combustion waves was formed, and the combustion synthesis was completed within about 3 seconds. After being allowed to cool, the reaction product was collected, and the crystalline layer was identified with a powder X-ray diffractometer. This revealed that the internal layer was formed of titanium carbide, and the surface layer was formed of a thermodynamically stable titanium oxide ($TiO_{2-x}$) obtained by a reaction of titanium carbide with oxygen in the air. In this manner, a titanium-oxide-containing porous ceramic molded body of titanium carbide represented by formula (TOC) was produced. The titanium oxide accounted for 10 wt % or less of the total weight.

Production Example 3: Formula (TCM)

A powder having a mean particle size of 45 μm was used as a titanium starting material. A carbon powder having a primary particle size of 0.1 μm or less was granulated to obtain granules having a secondary particle size of about 1 mm, and used as a carbon starting material. A silver powder having a mean particle size of 45 μm was used as a metal starting material. The titanium starting material, the carbon starting material, and the metal starting material were weighed so that the weight ratio was 0.66:0.17:0.17, and the resulting mixture was sufficiently mixed by stirring to be used as a starting material. The resulting starting material was press-molded into a cylindrical shape having a diameter of 20 mm and a height of 20 mm, thereby obtaining a green compact having a relative density of 45%. When a portion of the surface of the obtained green compact was ignited by laser in an argon atmosphere, a series of combustion waves was formed, and the combustion synthesis was completed within about 4 seconds. After being allowed to cool, the reaction product was collected, and the crystalline layer was identified with a powder X-ray diffractometer, which revealed that the principal components were titanium carbide ($TiC_{1-x}$) and silver (Ag). The element distribution was then analyzed using a fluorescent x-ray analyzer. As a result, silver was uniformly, finely dispersed around the titanium carbide, and no agglomerate was formed by melting and solidification. In this manner, a silver-containing porous ceramic molded body of titanium carbide represented by formula (TCM) was produced.

Production Example 4: Formula (TOCM)

When the same green compact as in Production Example 3 was ignited by electric discharge in air, a series of combustion waves was formed, and the combustion synthesis was completed within about 3 seconds. After being allowed to cool, the reaction product was collected, and the crystalline layer was identified with a powder X-ray diffractometer, which revealed that the internal layer was formed of titanium carbide and silver, and the surface layer was formed of titanium oxide ($TiO_{2-x}$) and silver. In this manner, a titanium-oxide-containing porous ceramic molded body of titanium carbide in which silver was finely dispersed (formula (TOCM)) was produced.

Production Example 5: Formula (TB)

A powder having a mean particle size of 45 μm was used as a titanium starting material. A powder having a particle size of 10 μm or less was used as a boron starting material. The titanium starting material and the boron starting material were weighed so that the weight ratio was 0.75:0.25, and the resulting mixture was sufficiently mixed by stirring to be used as a starting material. The resulting starting material was press-molded into a cylindrical shape having a diameter of 16 mm and a height of 30 mm, thereby obtaining a green compact having a relative density of 50%. When a portion at the upper surface of the obtained green compact was ignited by laser in an argon atmosphere, a series of combustion waves was formed, and the combustion synthesis was completed within about 1 second. After being allowed to cool, the reaction product was collected, and the crystalline layer was identified with a powder X-ray diffractometer, which revealed that the principal component was a mixed layer of titanium diboride ($TiB_2$) and titanium boride (TiB). In this manner, a porous ceramic molded body of titanium boride represented by formula (TB) was produced.

Production Example 6: Formula (TOB)

When a portion of the upper surface of the same green compact as in Production Example 5 was ignited by electric discharge in air, a series of combustion waves was formed, and the combustion synthesis was completed within about 1 second or less. After being allowed to cool, the reaction product was collected, and the crystalline layer was identified with a powder X-ray diffractometer, which revealed that the internal layer was formed of titanium boride, and the surface layer was formed of a thermodynamically stable titanium oxide ($TiO_{2-x}$) obtained by a reaction of titanium boride with oxygen in the air. In this manner, a titanium-oxide-containing porous ceramic molded body of titanium boride represented by formula (TOB) was produced. The titanium oxide accounted for 10 wt % or less of the total weight.

Production Example 7: Formula (TBM)

A powder having a mean particle size of 45 μm was used as a titanium starting material. A powder having a particle size of 10 μm or less was used as a boron starting material. A gold powder having a mean particle size of 45 μm was used as a metal starting material. The titanium starting material, the boron starting material, and the metal starting material were weighed so that the weight ratio was 6.75:2.25:1, and the resulting mixture was sufficiently mixed by stirring to be used as a starting material. The resulting starting material was press-molded into a cylindrical shape having a diameter of 16 mm and a height of 30 mm, thereby obtaining a green compact having a relative density of 50%. When a portion at the upper surface of the obtained green compact was ignited by laser in an argon atmosphere, a series of combustion waves was formed, and the combustion synthesis was completed within about 1 second. After being allowed to cool, the reaction product was collected, and the crystalline layer was identified with a powder X-ray diffractometer, which revealed that the principal components were titanium diboride ($TiB_2$), titanium boride (TiB), and gold (Au). The element distribution was then analyzed using a fluorescent x-ray analyzer. As a result, the gold was uniformly, finely dispersed around the titanium boride, and no agglomerate was formed by melting and solidification. In this manner, a gold-containing porous ceramic molded body of titanium boride represented by formula (TBM) was produced.

Production Example 8: Formula (TOBM)

When the same green compact as in Production Example 7 was ignited by electric discharge in air, a series of combustion waves was formed, and the combustion synthesis was completed within about 1 second. After being allowed to cool, the reaction product was collected, and the crystalline layer was identified with a powder X-ray diffractometer, which revealed that the internal layer was formed of titanium diboride (TiB$_2$), titanium boride (TiB), and gold (Au), and the surface layer was formed of titanium oxide (TiO$_{2-x}$) and gold. In this manner, a titanium-oxide-containing porous ceramic molded body of titanium boride in which gold was finely dispersed (formula (TOBM)) was produced.

Production Example 9: Formula (TN)

A powder having a mean particle size of 45 μm was used as a titanium starting material. This starting material was press-molded into a cylindrical shape having a diameter of 10 mm and a height of 20 mm to obtain a green compact having a relative density of 40%. When a portion at the upper surface of the obtained green compact was ignited by a heater in a nitrogen atmosphere (1.5 atm), a series of combustion waves was formed, and the combustion synthesis was completed within about 2 seconds. The nitriding degree at this time was as low as 10% or less, indicating the presence of titanium residue. Thus, the resulting product was collected after cooling, crushed to a size of about 45 μm or less, and press-molded again into the same shape to obtain a green compact having a relative density of 30%. When a portion at the upper surface of the obtained green compact was ignited by a heater in a high-pressure nitrogen atmosphere (60 atm), a series of combustion waves was formed, and the combustion synthesis was completed within about 4 seconds. After being allowed to cool, the reaction product was collected, and the crystalline layer was identified with a powder X-ray diffractometer, which revealed that the principal component was titanium nitride (TiN$_{0.9}$). In this manner, a porous ceramic molded body of titanium carbide represented by formula (TN) was produced.

Production Example 10: Formula (TON)

A powder having a mean particle size of 45 μm was used as a titanium starting material. This starting material was press-molded into a cylindrical shape having a diameter of 10 mm and a height of 20 mm to obtain a green compact having a relative density of 40%. When a portion at the upper surface of the obtained green compact was ignited by a heater in a nitrogen atmosphere (1.5 atm), a series of combustion waves was formed, and the combustion synthesis was completed within about 2 seconds. The nitriding degree at this time was as low as 10% or less, indicating the presence of titanium residue. Thus, the resulting product was collected after cooling, crushed to a size of about 45 μm or less, and press-molded again into the same shape to obtain a green compact having a relative density of 30%. When a portion at the upper surface of the obtained green compact was ignited by a heater in high-pressure air (30 atm), a series of combustion waves was formed, and the combustion synthesis was completed within about 4 seconds. After being allowed to cool, the reaction product was collected, and the crystalline layer was identified with a powder X-ray diffractometer, which revealed that the internal layer was formed of titanium nitride, and the surface layer was formed of a thermodynamically stable titanium oxide (TiO$_{2-x}$) obtained by a reaction of titanium nitride with oxygen in the air. In this manner, a titanium-oxide-containing porous ceramic molded body of titanium nitride represented by formula (TON) was produced. The titanium oxide accounted for 20 wt % or less of the total weight.

Production Example 11: Formula (TNM)

A powder having a mean particle size of 45 μm was used as a titanium starting material. A platinum powder having a particle size of 45 μm or less was used as a metal starting material. The titanium starting material and the metal starting material were weighed so that the weight ratio was 0.9:0.1, and the resulting mixture was sufficiently mixed by stirring to be used as a starting material. When a portion at the upper surface of the obtained green compact was ignited by a heater in a nitrogen atmosphere (1.5 atm), a series of combustion waves was formed, and the combustion synthesis was completed within about 2 seconds. The nitriding degree at this time was as low as 10% or less, indicating the presence of titanium residue. Thus, the resulting product was collected after cooling, crushed to a size of about 45 μm or less, and press-molded again into the same shape to obtain a green compact having a relative density of 30%. When a portion at the upper surface of the obtained green compact was ignited by a heater in a high-pressure nitrogen atmosphere (60 atm), a series of combustion waves was formed, and the combustion synthesis was completed within about 4 seconds. After being allowed to cool, the reaction product was collected, and the crystalline layer was identified with a powder X-ray diffractometer, which revealed that the principal components were titanium nitride (TiN$_{0.9}$) and platinum (Pt). The element distribution was then analyzed using a fluorescent x-ray analyzer. As a result, the platinum was uniformly, finely dispersed around the titanium nitride, and no agglomerate was formed by melting and solidification. In this manner, a porous ceramic molded body of titanium nitride in which platinum was finely dispersed (formula (TNM)) was produced.

Production Example 12: Formula (TONM)

A powder having a mean particle size of 45 μm was used as a titanium starting material. A platinum powder having a particle size of 45 μm or less was used as a metal starting material. The titanium starting material and the metal starting material were weighed so that the weight ratio was 0.9:0.1, and the resulting mixture was sufficiently mixed by stirring to be used as a starting material. When a portion at the upper surface of the obtained green compact was ignited by a heater in a nitrogen atmosphere (1.5 atm), a series of combustion waves was formed, and the combustion synthesis was completed within about 2 seconds. The nitriding degree at this time was as low as 10% or less, indicating the presence of titanium residue. Thus, the resulting product was collected after cooling, crushed to a size of about 45 μm or less, and press-molded again into the same shape to obtain a green compact having a relative density of 30%. When a portion at the upper surface of the obtained green compact was ignited by a heater in high-pressure air (30 atm), a series of combustion waves was formed, and the combustion synthesis was completed within about 4 seconds. After being allowed to cool, the reaction product was collected, and the crystalline layer was identified with a powder X-ray diffractometer, which revealed that the internal layer was formed of titanium nitride and platinum, and the surface layer was formed of platinum and thermodynamically stable titanium oxide ($TiO_{2-X}$) obtained by a reaction of titanium nitride with oxygen in the air. In this manner, a titanium-oxide-containing porous ceramic molded body of titanium nitride in which platinum was finely dispersed (formula (TONM)) was produced. The titanium oxide accounted for 20 wt % or less of the total weight.

Production Example 13: Formula (TS)

A powder having a mean particle size of 100 μm was used as a titanium starting material. A powder having a particle size of 1 μm or less was used as a silicon starting material. The titanium starting material and the silicon starting material were weighed so that the weight ratio was 0.74:0.26, and the resulting mixture was sufficiently mixed by stirring to be used as a starting material. The resulting starting material was press-molded to a bar shape whose one side was 15 mm and length was 100 mm, thereby obtaining a green compact having a relative density of 50%. When a portion at the upper surface of the obtained green compact was ignited by laser in an argon atmosphere, a series of combustion waves was formed, and the combustion synthesis was completed within about 6 seconds. After being allowed to cool, the reaction product was collected, and the crystalline layer was identified with a powder X-ray diffractometer, which revealed that the principal component was titanium silicide ($Ti_5Si_3$). In this manner, a porous ceramic molded body of titanium silicide represented by formula (TS) was produced.

Production Example 14: Formula (TOS)

When the same green compact as in Production Example 13 was ignited by electric discharge in air, a series of combustion waves was formed, and the combustion synthesis was completed within about 4 seconds. After being allowed to cool, the reaction product was collected, and the crystalline layer was identified by powder X-ray diffractometer, which revealed that the internal layer was formed of titanium silicide, and the surface layer was formed of titanium oxide ($TiO_{2-X}$). In this manner, a titanium-oxide-containing porous ceramic molded body of titanium silicide represented by formula (TOS) was produced. The titanium oxide accounted for 10 wt % or less of the total weight.

Production Example 15: Formula (TSM)

A powder having a mean particle size of 100 μm was used as a titanium starting material. A powder having a particle size of 1 μm or less was used as a silicon starting material. An iron powder having a mean particle size of 45 μm was used as a metal starting material. The titanium starting material, the carbon starting material, and the metal starting material were weighed so that the weight ratio was 0.67:0.23:0.1, and the resulting mixture was sufficiently mixed by stirring to be used as a starting material. The resulting starting material was press-molded to a bar shape whose one side was 15 mm and length was 100 mm, thereby obtaining a green compact having a relative density of 50%. When a portion at the upper surface of the obtained green compact was ignited by laser in an argon atmosphere, a series of combustion waves was formed, and the combustion synthesis was completed within about 6 seconds. After being allowed to cool, the reaction product was collected, and the crystalline layer was identified with a powder X-ray diffractometer, which revealed that the principal component was formed of titanium silicide ($Ti_5Si_3$) and iron (Fe). The element distribution was then analyzed using a fluorescent x-ray analyzer. As a result, the iron was uniformly, finely dispersed around the titanium silicide, and no agglomerate was formed by melting and solidification. In this manner, an iron-containing porous ceramic molded body of titanium silicide represented by formula (TSM) was produced.

Production Example 16: Formula (TOSM)

When the same green compact as in Production Example 15 was ignited by electric discharge in air, a series of combustion waves was formed, and the combustion synthesis was completed within about 5 seconds. After being allowed to cool, the reaction product was collected, and the crystalline layer was identified with a powder X-ray diffractometer, which revealed that the internal layer was formed of titanium silicide and iron, and the surface layer was formed of titanium oxide ($TiO_{2-X}$) and iron. In this manner, a titanium-oxide-containing porous ceramic molded body of titanium silicide in which iron was finely dispersed (formula (TOSM)) was produced. The titanium oxide accounted for 10 wt % or less of the total weight.

Production Example 17: Formula (BN)

A powder having a mean particle size of 45 μm was used as a titanium starting material. A powder having a mean particle size of several micrometers was used as a boron nitride starting material. The titanium starting material and the boron nitride starting material were weighed so that the weight ratio was 0.74:0.26, and the resulting mixture was sufficiently mixed by stirring to be used as a starting material. The resulting starting material was press-molded to a cylindrical shape having a diameter of 40 mm and a height of 40 mm, thereby obtaining a green compact having a relative density of 50%. When a portion at the upper surface of the obtained green compact was ignited by laser in an argon atmosphere, a series of combustion waves was formed, and the combustion synthesis was completed within about 8 seconds. After being allowed to cool, the reaction product was collected, and the crystalline layer was identified with a powder X-ray diffractometer, which revealed that the principal component was a mixed layer of titanium diboride ($TiB_2$) and titanium nitride (TiN). In this manner, a porous ceramic molded body of titanium boride and titanium nitride represented by formula (BN) was produced.

Production Example 18: Formula (OBN)

When a portion of the upper surface of the same green compact as in Production Example 17 was ignited by electric discharge in air, a series of combustion waves was formed, and the combustion synthesis was completed within about 7 seconds. After being allowed to cool, the reaction product was collected, and the crystalline layer was identified with a powder X-ray diffractometer, which revealed that the internal layer was formed of titanium boride and titanium nitride, and the surface layer was formed of a thermodynamically stable titanium oxide ($TiO_{2-X}$) obtained by a reaction of titanium boride and titanium nitride with oxygen in the air. In this manner, a titanium-oxide-containing porous ceramic molded body of titanium boride and titanium nitride represented by formula (OBN) was produced. The titanium oxide accounted for 10 wt % or less of the total weight.

Production Example 19: Formula (BNM)

A powder having a mean particle size of 45 μm was used as a titanium starting material. A powder having a mean particle size of several micrometers was used as a boron nitride starting material. A copper powder having a mean particle size of 10 μm was used as a metal starting material. The titanium starting material, the boron nitride starting material, and the metal starting material were weighed so that the weight ratio was 0.59:0.21:0.2, and the resulting mixture was sufficiently mixed by stirring to be used as a starting material. The resulting starting material was press-molded to a cylindrical shape having a diameter of 40 mm and a height of 40 mm, thereby obtaining a green compact having a relative density of 50%. When a portion at the upper surface of the obtained green compact was ignited by laser in an argon atmosphere, a series of combustion waves was formed, and the combustion synthesis was completed within about 8 seconds. After being allowed to cool, the reaction product was collected, and the crystalline layer was identified with a powder X-ray diffractometer, which revealed that the principal component was a mixed layer of titanium diboride ($TiB_2$), titanium nitride (TiN), and copper (Cu). The element distribution was then analyzed using a fluorescent x-ray analyzer. As a result, the copper was uniformly, finely dispersed around the titanium boride and titanium nitride, and no agglomerate was formed by melting and solidification. In this manner, a copper-containing porous ceramic molded body of titanium boride and titanium nitride represented by formula (BNM) was produced.

Production Example 20: Formula (OBNM)

When the same green compact as in Production Example 19 was ignited by electric discharge in air, a series of combustion waves was formed, and the combustion synthesis was completed within about 7 seconds. After being allowed to cool, the reaction product was collected, and the crystalline layer was identified with a powder X-ray diffractometer, which revealed that the internal layer was formed of titanium diboride ($TiB_2$), titanium nitride (TiN), and copper (Cu), and the surface layer was formed of titanium oxide ($TiO_{2-x}$) and copper. In this manner, a titanium-oxide-containing porous ceramic molded body of titanium boride and titanium nitride in which copper was finely dispersed (formula (OBNM)) was produced. The titanium oxide accounted for 10 wt % or less of the total weight.

Test Example 1: Porous Texture

Figure 2:
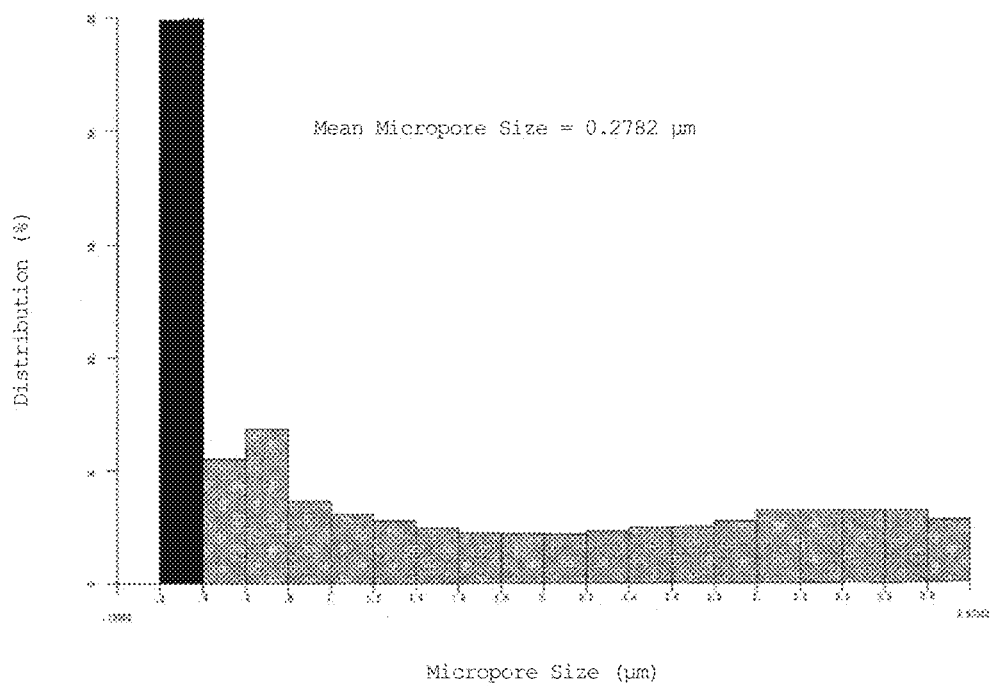
FIG. 2 is a graph illustrating the micropore size distribution of a porous ceramic (formula (TC)) obtained by combustion synthesis.
Figure 3:
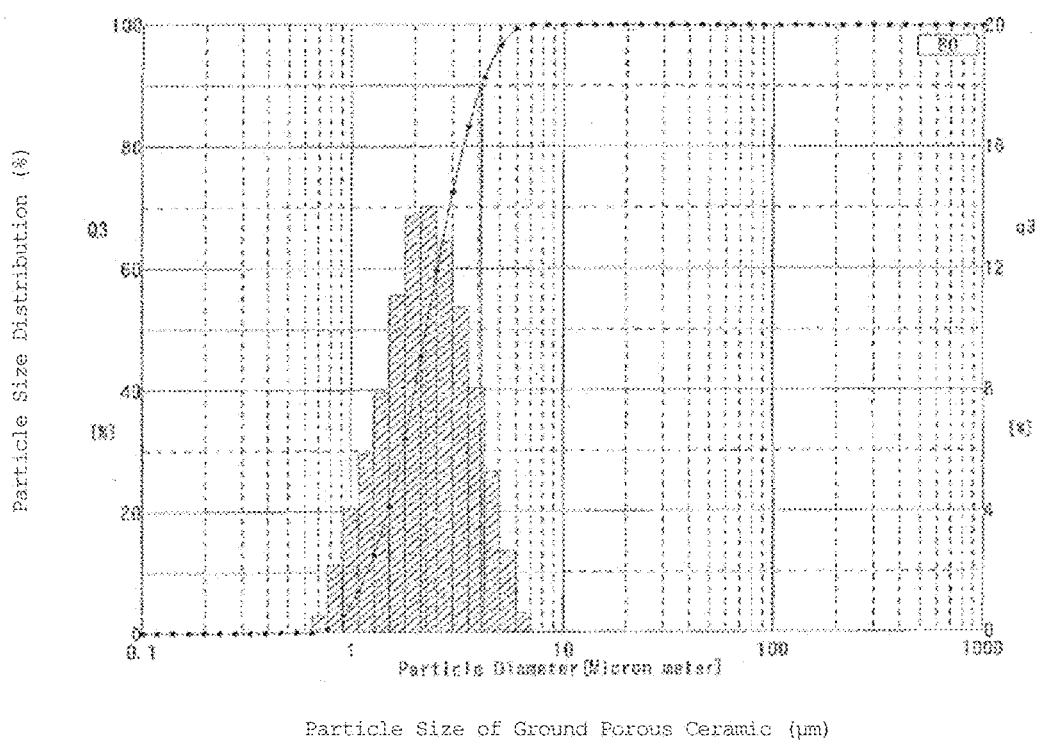
FIG. 3 is a graph illustrating the powder particle size distribution of a ground porous ceramic (formula (TC)) obtained by combustion synthesis.

FIG. 1 shows an example of an electron microscope photograph of the porous ceramic molded body of titanium carbide obtained in Production Example 1. The porosity of the entire molded body was 60%. The molded body had a skeleton structure in which the ceramic molecules were also three-dimensionally coupled, and the space was also three-dimensionally continuous, with various pore sizes ranging from about 0.2 μm to about 15 μm. As shown in FIG. 2, the mean pore size of the entire molded body was about 0.28 μm. FIG. 3 illustrates the particle size distribution of a powder obtained by coarsely crushing the porous ceramic molded body with an Orient mill, and then finely grinding the coarse powder with a jet mill. The resulting powder had a mean particle size ($D_{50}$) of 2.264 μm.

Because the powder obtained by grinding the molded body even had a mean pore size about 1/10 the size of the powder as described above, the ground material was porous ceramic. Substantially the same results were confirmed with the porous ceramic molded bodies and their ground materials of Production Examples 2 to 20.

In the Test Examples below, the molded body of porous ceramic (one continuous mass) is referred to as "ceramic molded body," and the ground molded body is referred to as "ceramic powder." The product obtained by adding the ceramic molded body to water or an aqueous solution is referred to as "processed water," and the product obtained by adding the ceramic powder to water or an aqueous solution is referred to as "powder-containing water."

Test Example 2: Measurement of Radicals

The porous ceramics of the present invention were brought into contact with a liquid, and radicals contained in the resulting liquid were measured. The ceramic powders used were of Production Examples 1 to 4, and the liquid was pure water.

Figures 1, 4:
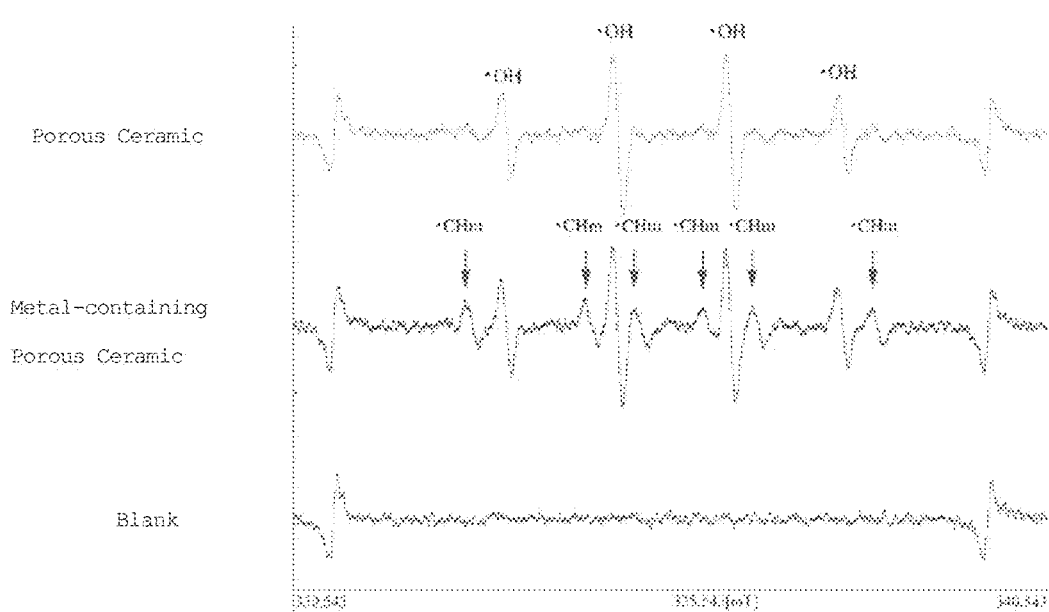
Figures 2, 4:
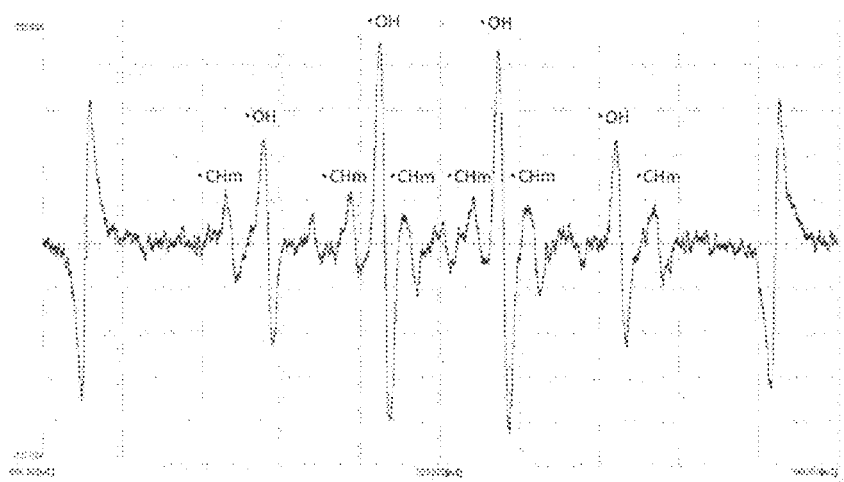

The radical species was measured with an electron spin resonator (ESR). DMPO (concentration: 5%) was used as a spin-trapping agent. The X band was used as the measurement frequency band. The maximum magnetic field intensity was 0.65 T, and the sweep time was 120 seconds. The upper part of FIG. 4-1 shows the radical species generated when pure water came into contact with the ceramic powder of Production Example 1, which is a typical non-oxide ceramic represented by formula (TC), or the ceramic powder of Production Example 2, which is a typical non-oxide ceramic containing a small amount of oxide ceramic represented by formula (TOC). In this case, signal analysis confirmed the presence of hydroxy radicals (.OH).

The radical lifetime is said to be about several microseconds to several seconds, and greatly varies over time. In this measurement also, the ceramic powder was added to pure water, and then a DMPO solution was added thereto. After the radicals were trapped, the solution was collected to measure the radical species with an electron spin resonator. Thus, the absolute amount of radicals varied over the course of the operation. For this reason, the absolute amount of radicals is unknown, but the relative amount of radicals can be speculated from the signal intensity of electron spin resonance. As shown in the bottom part of FIG. 4-1 (blank), the relative amount of radicals was determined from the relative ratio of the external standard peak intensity (the concentration is constant) of manganese ions at each end to the highest peak intensity of radical species. This resulted in the relative ratio of the hydroxy radical ranging from 50% to 500%.

The middle part of FIG. 4-1 shows the radical species generated when pure water came into contact with the ceramic powder of Production Example 3, which is a typical non-oxide ceramic having a metal dispersed, represented by formula (TCM) or the ceramic powder of Production Example 4, which is a typical non-oxide ceramic containing a small amount of a metal and an oxide ceramic, represented by formula (TOCM). In this case, the presence of methyl radicals ($.CH_m$) in addition to hydroxy radicals was confirmed.

FIG. 4-2 shows radical species generated when ultrasound with a frequency of about 1 MHz to 2 MHz was externally applied, with the ceramic powder of Production Example 1 or Production Example 2 in contact with pure water. The presence of methyl radicals in addition to hydroxy radicals was confirmed. This revealed that even porous ceramic containing no metal or alloy can also increase radical species through the application of ultrasonic energy.

Epigenetics, in which an epigenome such as DNA methylation and hydroxy methylation functions as a switch to turn genes on or off, will be an important topic in the post-genome, and studies of epigenetics are expected to reveal life phenomena and the causes of diseases that have remained unexplained by previous genome research. DNA methylation (5 mC) and hydroxy methylation (5 hmC) refer to a process by which a methyl group or a hydroxymethyl group is added to cytosine. This study confirmed the generation of hydroxy radicals and methyl radicals, which appears to be involved in the prevention of epigenetics failure (the prevention of abnormal gene expression, such as cancer and lifestyle-related diseases, different from the normal state).

Test Example 3: Measurement of Nanobubbles

Table 2 shows the number of nanobubbles contained in water prepared by bringing 12 different ceramic molded bodies obtained in Production Examples 1 to 12 as typical examples of porous ceramics obtained through combustion synthesis into contact with ultrapure water. The number of nanobubbles was determined by nanoparticle tracking analysis. The results indicate that the number of nanobubbles per milliliter was approximately $10^7$ in every case.

TABLE 2

Results of Measuring the Number of Nanobubbles

|  |  | Formula | Number of Nanobubbles per mL |
|---|---|---|---|
| Test Group | Production Example 1 | TC | $10^7$ |
|  | Production Example 2 | TOC | $10^7$ |
|  | Production Example 3 | TCM | $10^7$ |
|  | Production Example 4 | TOCM | $10^7$ |
|  | Production Example 5 | TB | $10^7$ |
|  | Production Example 6 | TOB | $10^7$ |
|  | Production Example 7 | TBM | $10^7$ |
|  | Production Example 8 | TOBM | $10^7$ |
|  | Production Example 9 | TN | $10^7$ |
|  | Production Example 10 | TON | $10^7$ |
|  | Production Example 11 | TNM | $10^7$ |
|  | Production Example 12 | TONM | $10^7$ |
| Control Group | Ultrapure Water |  | 0 |

Figures 1, 5:
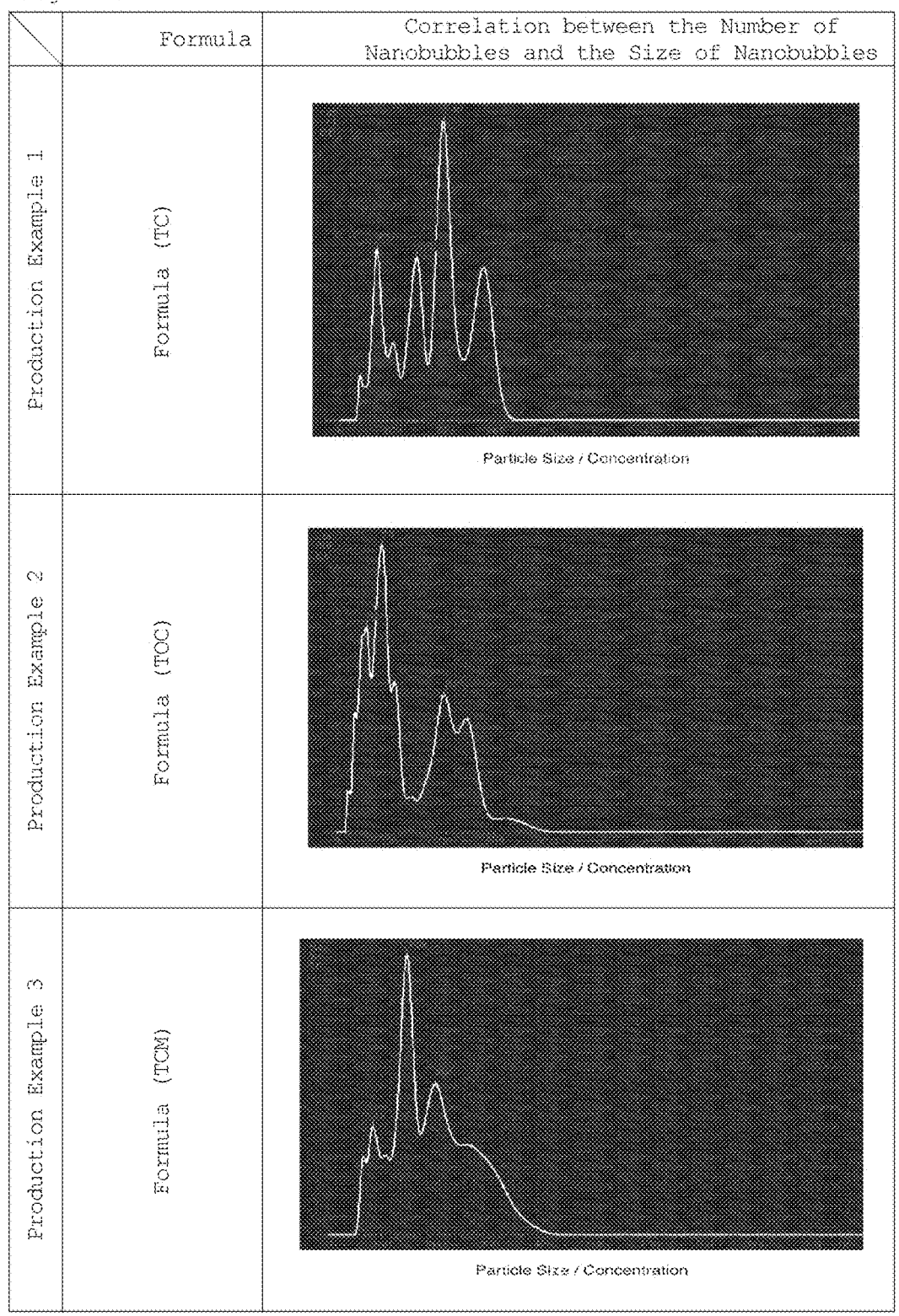

Subsequently, the size of the nanobubbles was measured. FIGS. 5-1 to 5-4 show the correlations between the number of the nanobubbles and the size of the nanobubbles contained in the water brought into contact with the ceramic molded bodies of Production Examples 1 to 12. Every Example has a bubble size distribution in the range of about 20 nm to about 400 nm. Emissions from automobiles and thermal power generation are an issue these days. Solid fine particles, such as PM 2.5, which has a size of about 2.5 μm, are less likely to enter the bloodstream through the respiratory organs, such as the lungs, but now PM 0.5 (500 nm) has emerged as a new problem. Secondhand smoke from cigarettes is considered to contain PM 0.5.

Epidemiological studies report that fine particles of this size can be captured by alveoli and taken into the bloodstream, causing serious impact on the human body (e.g., circulatory diseases as well as respiratory diseases). Given the fact that even solid fine particles such as PM 0.5 can be taken into the bloodstream, the nanobubbles generated by bringing the porous ceramics into contact with water are assumed to be easily absorbed into the body because of their gaseous form, not a solid form, and their smaller bubble size of about 20 nm to about 400 nm.

Test Example 4: Nanobubble Component Analysis

To find the amount of nanobubbles, the entire volume of nanobubbles was calculated by multiplying the volume determined from the average size of the nanobubbles by the number of nanobubbles. The results showed that the concentration of nanobubbles in a unit volume of water was about 5 ppb. Components of the nanobubbles were then analyzed. The ceramic molded bodies of Production Examples 1 to 4 shown in Table 3 were added to degassed water obtained by removing dissolved gas contained in ultrapure water, thereby preparing processed water. The processed water was measured with a dissolved hydrogen gas measurement device (measurement limit: 0.1 ppb). As a result, there was little difference in the concentration of hydrogen between ultrapure water and processed water, as shown in Table 3, indicating that hydrogen in the aqueous solution was not detected.

TABLE 3

Results of Measuring Dissolved Gas (Hydrogen) in Water

|  |  | Formula | Concentration of Hydrogen (ppb) |
|---|---|---|---|
| Test Group | Production Example 1 | TC | 0.79 |
|  | Production Example 2 | TOC | 0.79 |
|  | Production Example 3 | TCM | 0.74 |
|  | Production Example 4 | TOCM | 0.74 |
| Control Group | Ultrapure Water |  | 0.85 |

Next, the gas component contained in an amount of about 5 ppb was measured with a liquid chromatograph/mass spectrometer (LC/MS/MS), but the gas component could not be analyzed because it was an infinitesimal amount as small as the detection limit. However, since the presence of nanobubbles was confirmed regardless of the type of ceramic molded bodies in Production Examples 1 to 4, the gas component was assumed to be stabilized as, possibly not hydrogen gas, but gas that involves components derived from the porous ceramics or derived from a slight amount of unreacted starting materials present after combustion synthesis, or gas that involves oxygen (O) and/or nitrogen (N) dissolved in water in a secondary reaction of hydrogen radicals ($C_vB_wH_xN_yO_z$ ($0 \leq v, w, x, y, z \leq 1$)).

Test Example 5: pH Measurement

When hydrogen ions occurring from hydrogen radicals are present, the pH shifts toward the acidic range. Thus, normal tap water served as control groups, and processed water prepared by adding the ceramic molded bodies of Production Examples 1 to 12 to the same tap water served as test groups. The results of the pH measurement showed that while the control groups had an average pH of 7.42, the test groups exhibited a pH of 7.46, showing no significant difference between the groups. This indicates that even though hydrogen radicals were present in the test groups, the radicals did not convert into hydrogen ions, and there was no increase in hydrogen ions.

Test Example 6: Toxicity Test

As to chemical safety, the porous ceramic of the present invention is stable also in vivo due to its covalent character. Additionally, silver, gold, platinum, iron, and copper used in the present invention have already been prescribed in regulations for food additives and have no safety problems. Thus, a toxicity test was performed at the cell level, animal level, and clinical level.

1) In Vitro Test at Cell Level

Cytotoxicity on Madin-Darby canine kidney (MDCK) cells was examined using a test sample obtained by adding the ceramic molded body shown in Production Example 6, as an example of formula (TOB), to a culture solution. One ceramic molded body of Production Example 6 was added to 1 L of pure water, and the mixture was allowed to stand at room temperature for 24 hours to obtain a test sample stock solution. The solution was diluted 10 times stepwise with phosphate buffered saline (PBS). 50 µL of the test sample stock solution or the diluted solution and 50 µL of a suspension of MDCK cells in a Dulbecco's Modified Eagle's Medium (DMEM) containing 5% fetal bovine serum (FBS) were inoculated into a 96-well plate. The number of MDCK cells was $5 \times 10^4$. Thereafter, the cells were cultured in a $CO_2$ incubator for 4 days. After culture, 100 µL of PBS in which 4% formalin and 0.1% crystal violet were dissolved was added to each well, and the mixture was allowed to stand at room temperature for 10 minutes to stain the cells.

After staining, the culture was washed with tap water and dried, and then 50 µL of ethanol was added to each well to elute the crystal violet, followed by measuring absorbance at 585 nm. Cytotoxicity of each sample was confirmed taking the absorbance of the wells containing the cells to which PBS was added as 100% in the viable cell rate. Table 4 shows the results. The viable cell rate for each test sample was calculated taking the result of the control in which no porous ceramic was added as 100% in the viable cell rate. When the viable cell rate was 50% or less, the test sample was determined to be cytotoxic.

Even in the use of the test sample stock solution, the viable cell rate was 104.0±3.0%, showing little difference from the control. When the test sample obtained by diluting the stock solution was used, the viable cell rate was of course almost 100%. This indicates that the ceramic molded body of Production Example 6 exhibited no toxicity to MDCK cells when added to the culture solution.

TABLE 4

Results of Cytotoxicity Test on MDCK Cells

| Sample | Dilution Rate | Viable Cell Rate (%) |
|---|---|---|
| Test Sample | Stock Solution | 104.0 ± 3.0 |
|  | 1/10 | 99.9 ± 5.1 |
|  | 1/100 | 101.5 ± 7.0 |
|  | 1/1,000 | 97.0 ± 5.8 |
|  | 1/10,000 | 102.8 ± 7.6 |
| Control | No specimen added (PBS) | 100.0 ± 7.1 |

In the same manner as above, as an example of the porous ceramic represented by formula (TOC) or formula (TOCM), a culture solution to which the ceramic powder of Production Example 2 or 4 was added was prepared as a test sample, and cytotoxicity of each test sample was examined using Madin-Darby canine kidney (MDCK) cells. Table 5 shows the results. The test sample stock solution was added so that the culture solution had a ceramic powder concentration of 1000 ppm, and the stock solution was also diluted 10 times stepwise, thereby preparing 7 solutions, the lowest concentration of which was 0.001 ppm. The viable cell rate for each test sample was calculated taking the result of the control containing only PBS as 100% in the viable cell rate. When the viable cell rate was 50% or less, the test sample was determined to be cytotoxic.

TABLE 5

Results of Cytotoxicity Test on MDCK Cells

| Sample | Concentration of Powdery Porous Ceramic (ppm) | Viable Cell Rate (%) | |
|---|---|---|---|
| | | Production Example 4 (TOCM) | Production Example 2 (TOC) |
| Test Sample | 1,000 | 64 ± 2 | 63 ± 3 |
|  | 100 | 60 ± 4 | 91 ± 7 |
|  | 10 | 64 ± 4 | 90 ± 14 |
|  | 1 | 82 ± 7 | 105 ± 13 |
|  | 0.1 | 97 ± 7 | 90 ± 8 |
|  | 0.01 | 94 ± 7 | 91 ± 6 |
|  | 0.001 | 100 ± 7 | 100 ± 5 |
| Control | 0 (PBS) | 100 ± 6 | |

The results indicate that even in the use of the culture solution with the highest concentration, 1000 ppm, the viable cell rate was 60% or more, and that none of the ceramic powders exhibited cytotoxicity.

2) In Vivo Test at Animal Level: Chronic Toxicity

Next, since toxicity was not confirmed at the cell level, an in vivo test was performed on fish. Large amounts of the 20 different ceramic molded bodies of Production Examples 1 to 20 were placed on the bottom of a water tank so that the volume of the ceramic molded bodies was 20 vol % of water, and tropical fish were grown in the water. Because there was no problem with the fish for at least the last two years, the ceramic molded bodies were determined to be nontoxic.

Figure 6:
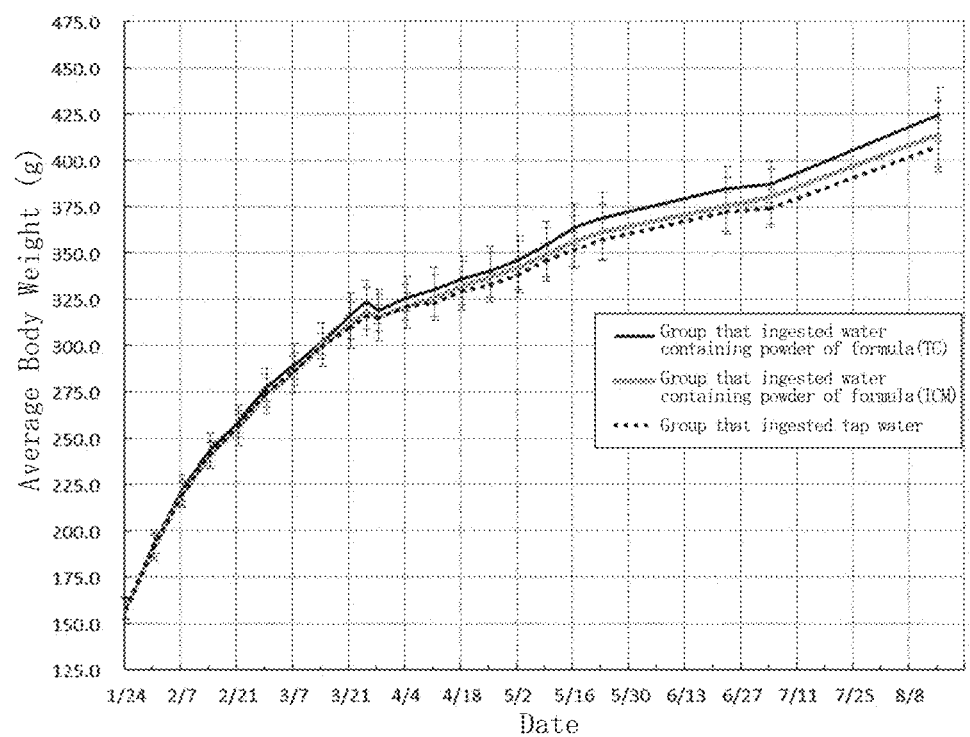
FIG. 6 is a graph illustrating the results of a toxicity test using Fischer rats.

Next, an in vivo chronic toxicity test was performed on rats. For the test group, as an example of the porous ceramic represented by formula (TC) or formula (TCM), two types of ceramic powders obtained in Production Examples 1 and 3 were individually added to tap water to give a concentration of 100 ppm, thereby preparing powder-containing water. Rats were freely able to orally intake the powder-containing water as drinking water through a water-feeding bottle every day. The control group was given normal tap water. For each group, n was 8. Because the daily water intake was 25 cc on average, the average intake of each ceramic powder was 2.5 mg/day. FIG. 6 shows changes in their body weight.

The rats were administered these two types of ceramic powder-containing water for 204 days (total intake of ceramic powder: 510 mg), but exhibited healthy growth without a decrease in body weight. This total intake corresponds to about 0.2% of the average body weight of the rats (about 280 g). If the porous ceramics of the present invention had any toxicity, the toxicity would manifest as weight loss; however, the rats instead exhibited an increase in body weight more than the group administered normal tap water. No test group showed decreased appetite, behavioral suppression, or the like, indicating that the porous ceramics had no chronic toxicity. The porous ceramic intake per unit body weight (body weight factor) was about 15.8 mg/kg/day in every group on the day the experiment was started, and 5.9 to 6.1 mg/kg/day on the day the experiment ended.

3) In Vivo Test at Clinical Level: Chronic Toxicity

Since toxicity was not confirmed at the animal level, a clinical test for chronic toxicity was performed on voluntary subjects. The ceramic molded body of Production Example 4 was used as a typical example of the porous ceramic represented by formula (TOCM). One ceramic molded body of Production Example 4 was added to 2 L of tap water, and the mixture was allowed to stand at room temperature for 12 hours to prepare processed water as a specimen. Voluntary subject A1 (male in his 70s) orally ingested the specimen in an amount of 1 L/day for two consecutive years, but exhibited no physical worsening, development of diseases, etc. Voluntary subject A2 (male in his 30s) also orally ingested the specimen in an amount of 2 L/day for six consecutive months, but did not exhibit physical worsening, disease development etc., instead maintaining excellent health conditions.

Next, a tablet containing 30 mg of the ceramic powder of Production Example 4 was prepared. Voluntary subjects A3 (male in his 60s), A4 (female in her 60s), A5 (male in his 50s), and A6 (male in his 30s) orally ingested the tablet at a dose of one tablet per day (30 mg) for two consecutive weeks together with drinking water, and exhibited no physical worsening, disease development, etc. The body weight factor was within the range of 0.4 to 0.6 mg/kg/day. Voluntary subjects A7 (male in his 70s) and A8 (female in her 80s) orally ingested the tablet at a dose of 3 tablets per day (90 mg) for six consecutive months, but there was no problem. The body weight factor was within the range of 1.1 to 2 mg/kg/day, and the total intake of the ceramic powder was 16.2 g. The results reveal that the ceramic molded bodies also have no chronic toxicity to the human body.

4) In Vivo Test at Clinical Level: Acute Toxicity

An acute toxicity test was performed on voluntary subjects. Voluntary subjects B1 (male in his 40s), B2 (female in her 20s), and B3 (male in his 30s) orally ingested ceramic powders of Production Example 2, Production Example 3, and Production Example 4, respectively, in an amount of 6 g one time, 5 times in total, together with drinking water, and exhibited no acute toxicity. The body weight factor was within the range of 100 to 150 mg/kg/day, and the total intake of the ceramic powder was 30 g.

Test Example 7: Crohn's Disease

Figure 7:
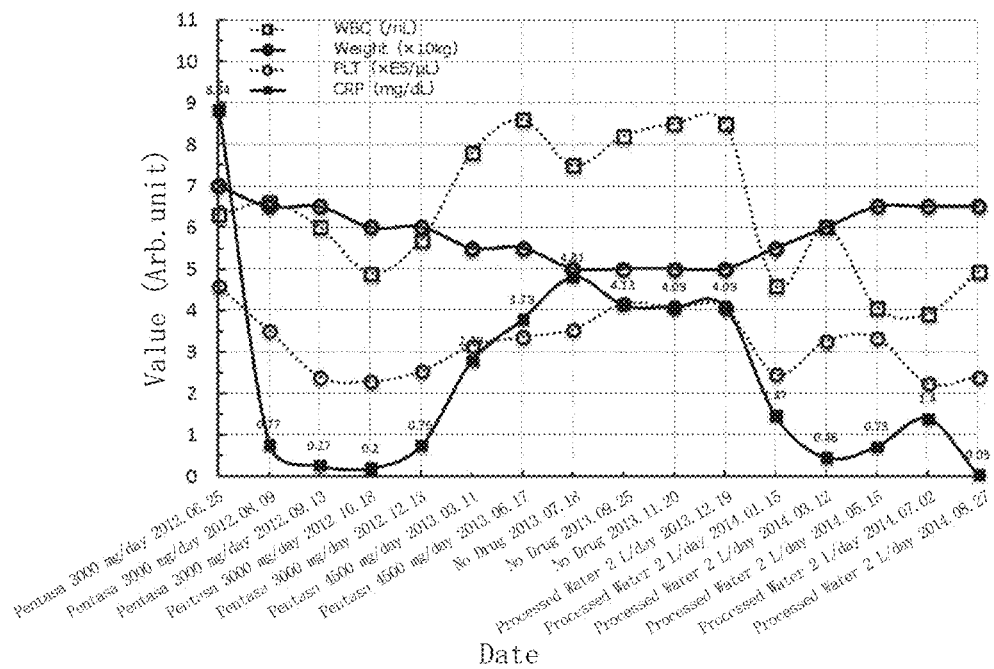
FIG. 7 is a graph illustrating changes in test values over time of a patient diagnosed with Crohn's disease.

Inflammatory intestinal diseases are largely represented by Crohn's disease and ulcerative colitis, and are specified by the Japanese government as intractable diseases. In this study, patient C (male in his 20s), who was a voluntary subject diagnosed with Crohn's disease, orally ingested the porous ceramic of the present invention, and various changes, including C-reactive protein (CRP), were measured. As a typical example of the porous ceramic represented by formula (TOCM), one ceramic molded body of Production Example 4 was added to 2 L of tap water, thereby preparing processed water. FIG. 7 shows the results of the test of this processed water intake in chronological order from emergency hospitalization at onset of the disease.

After discharge from the hospital as a result of CRP having become 0.2, the subject exhibited increases in C-reactive protein, white blood cells (WBC), and platelets (PLT), while having side effects such as fever, abdominal pain, general malaise, diarrhea, and bloody stool, despite the administration of a Pentasa drug (5-aminosalicylic acid) used in Crohn's disease treatment, and his body weight also decreased from 70 kg in a healthy condition to 50 kg. Thus, the administration of the Pentasa drug was discontinued for about 5 months. Thereafter, the subject orally ingested only processed water in an amount of 2 L/day. After about 8 months, CRP steeply dropped to 0.05 mg/dL, while blood conditions improved, with no side effects. His body weight also steadily increased to 65 kg.

The results reveal that only the intake of processed water containing the porous ceramic of the present invention can improve the medical conditions without the need of other drugs. Although not shown in the figure, in regular medical consultation in October 2014, CRP was 0.15 mg/dL, which was within the normal range (0.20 mg/dL or less). Thus, his doctor determined that the subject's conditions had returned to normal. The present invention may thus be able to provide a novel treatment method for Crohn's disease, which is currently recognized as an intractable disease with no basic treatment.

Test Example 8: Cancer In Vitro

Figures 1, 8:
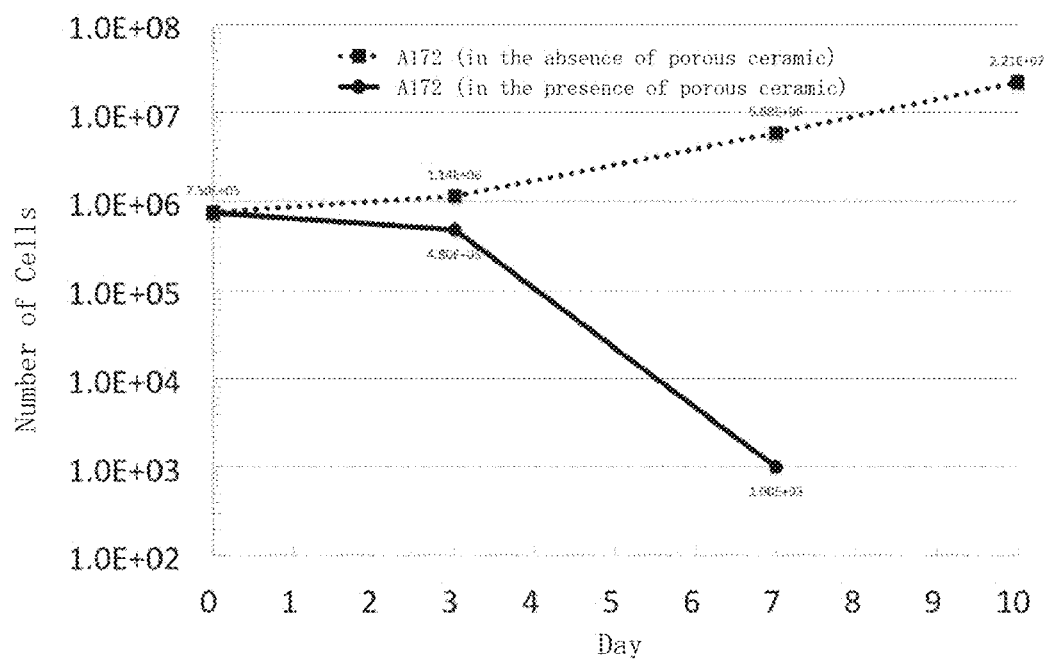
Figures 2, 8:
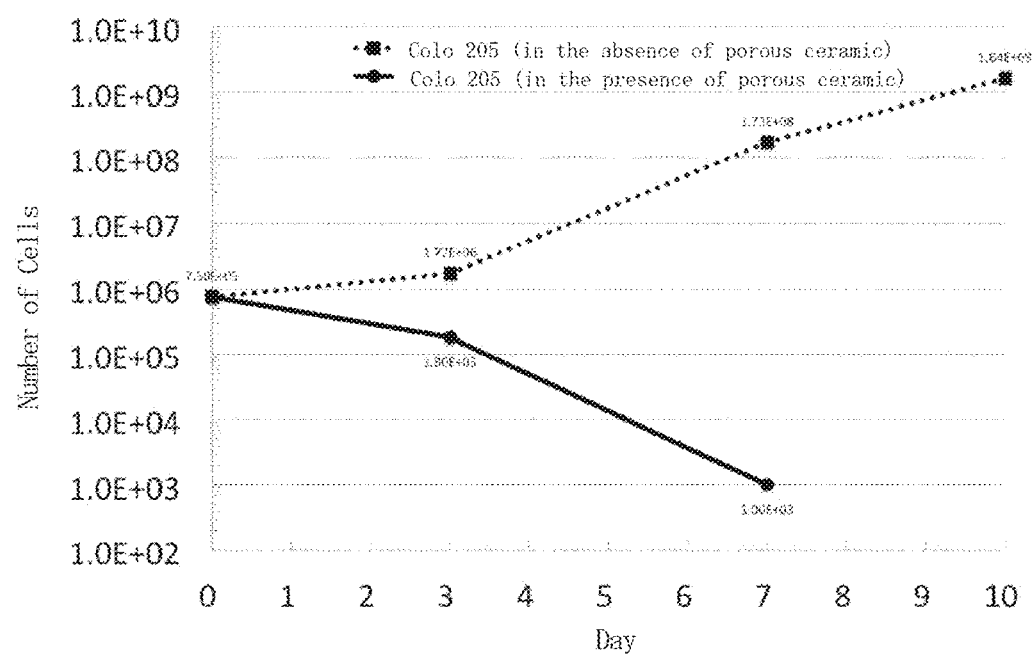
Figures 3, 8:
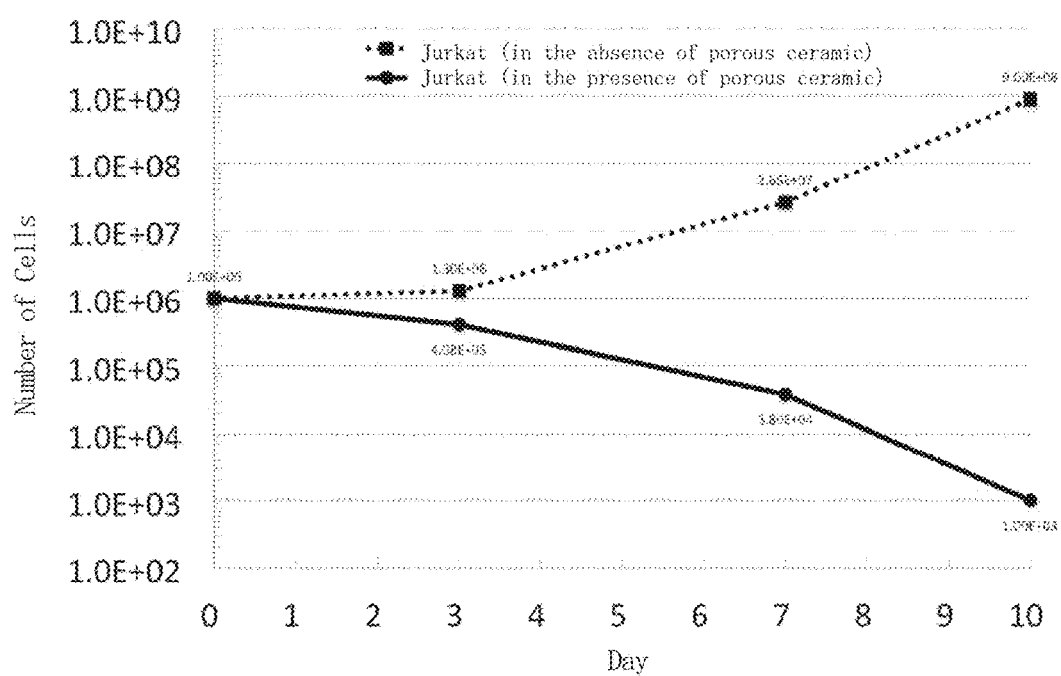
Figures 4, 8:
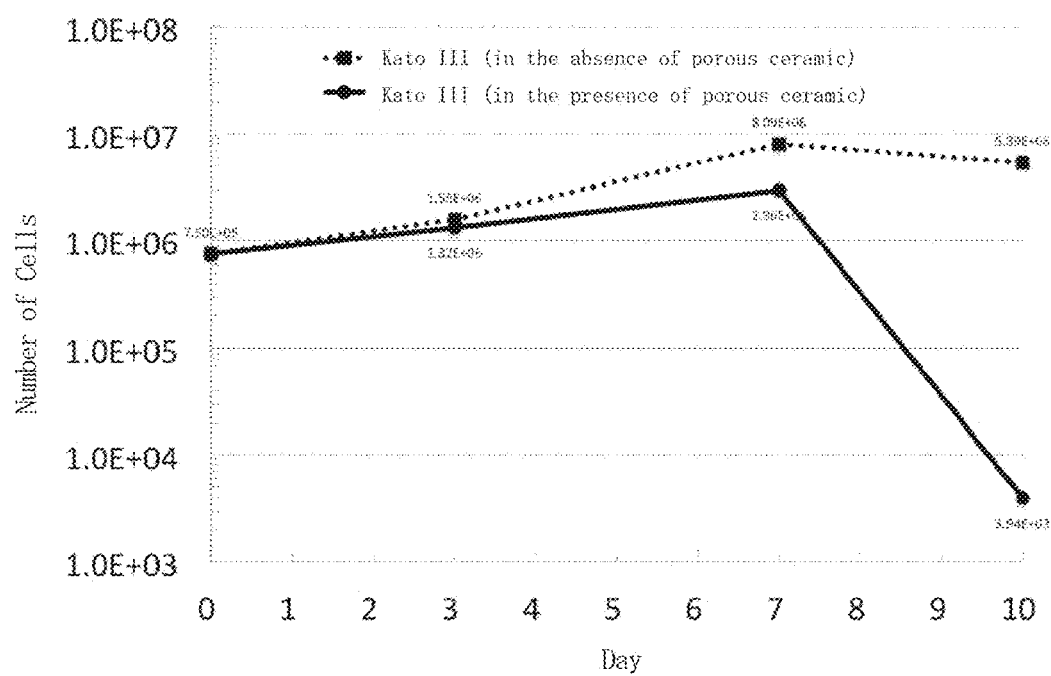
Figures 5, 8:
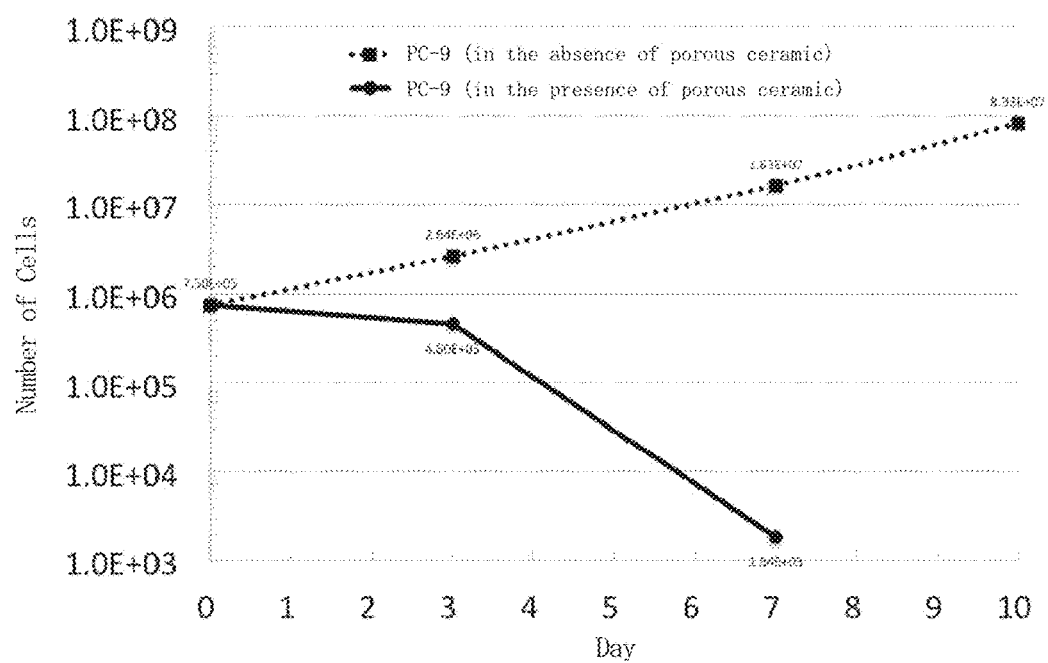
Figures 6, 8:
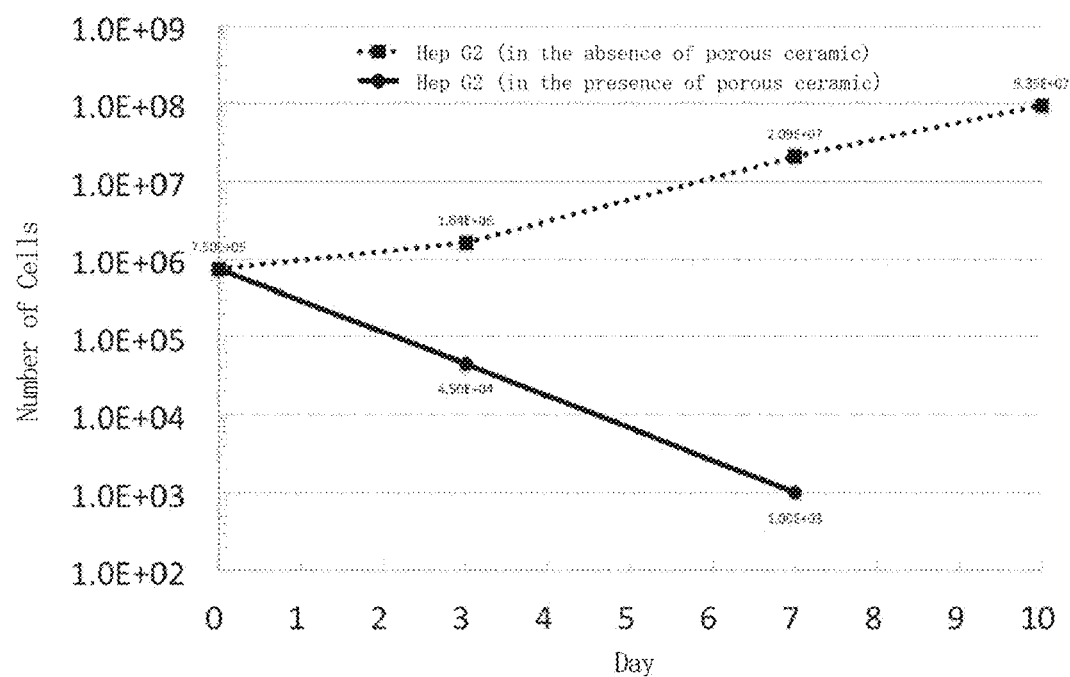

A study was performed to examine a growth inhibition effect on each of 6 types of human cancer cells in a culture solution to which 100 ppm of the ceramic powder of Production Example 4 was added as a typical example of the porous ceramic represented by formula (TOCM). FIGS. 8-1 to 8-6 show the results of in vitro tests each using brain tumor cell line A172, colorectal cancer cell line Colo 205, leukemia cell line Jurkat, stomach cancer cell line Kato III, lung cancer cell line PC9, or liver cancer cell line Hep G2. While the 6 types of cancer cells grew logarithmically in the absence of the porous ceramics, the use of the porous ceramics exhibited a potent inhibitory effect on all of the cancer cells regardless of the type of cancer, substantially decreasing the number of cells. The number of cancer cells on the order of $10^3$ or less in the figure was unmeasurable, and counting was discontinued. Similar growth inhibition effects were also confirmed with the ceramic powders of Production Examples 1 and 3 as typical examples of those represented by formula (TC) and formula (TCM). As noted above, the porous ceramic of the present invention can decrease the number of cancer cells, regardless of the type of cancer.

Figure 9:
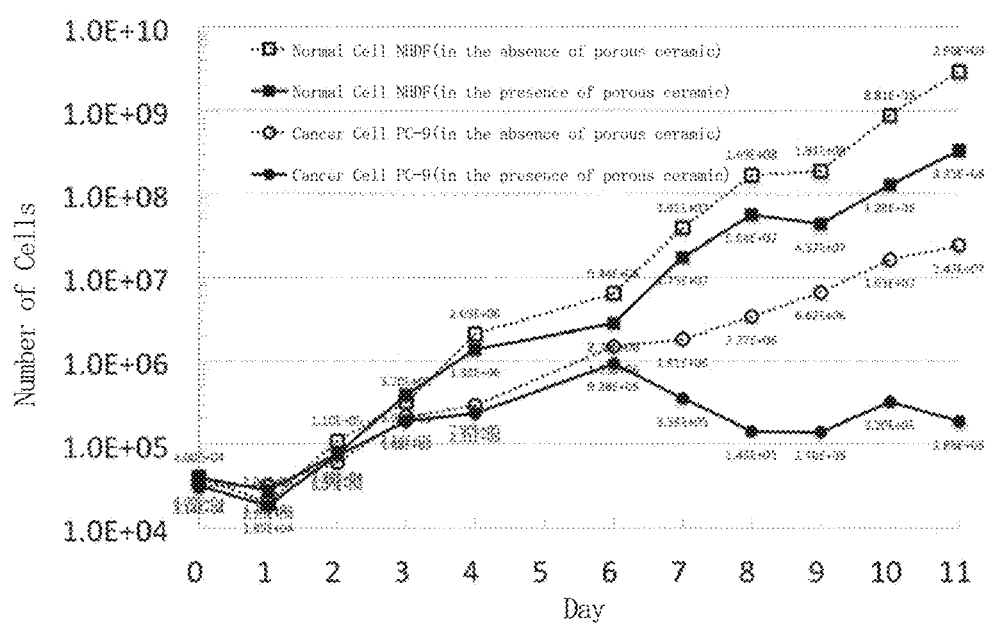
FIG. 9 is a graph illustrating the results of an in vitro test for growth inhibition on normal cell line NHDF and lung cancer cell PC9.

Next, as a typical example of the porous ceramic represented by formula (TOCM), one ceramic molded body of Production Example 4 was added to a culture solution, and the growth inhibition effect was examined with the cancer cells being not in direct contact with the porous ceramic. FIG. 9 shows the results of growth inhibition in the use of normal cell line NHDF (human derived fibroblast) and lung cancer cell line PC9 under the same conditions. In this test as well, due to the presence of the porous ceramic, a potent growth inhibition effect on lung cancer cells was observed, and the cells started to decrease on day 6. In normal cells, a slight degree of growth inhibition was observed as compared with the case in which the porous ceramic was absent, but the cells grew in a healthy manner without showing a decrease in its number. The results suggest that the porous ceramic of the present invention can be used as a cancer therapeutic drug and/or cancer preventive drug that can decrease only cancer cells with little influence on normal cells.

Figures 1, 18:
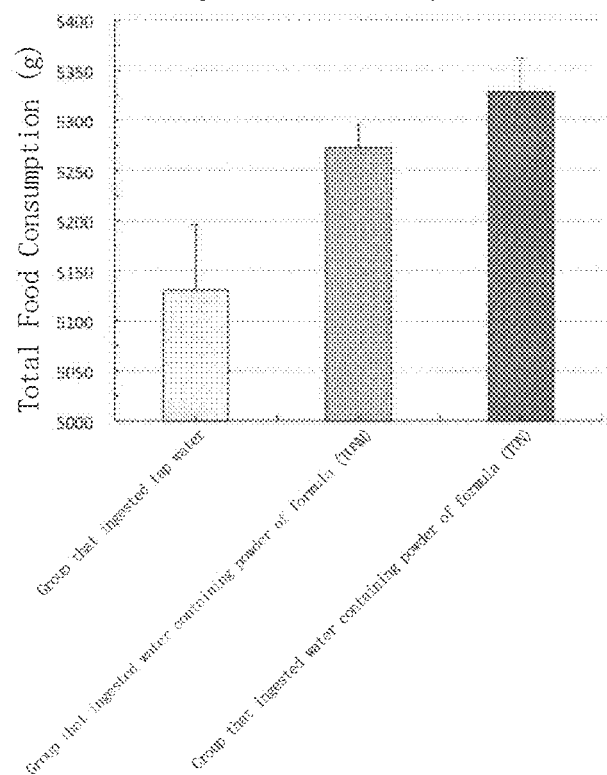
Figures 2, 18:
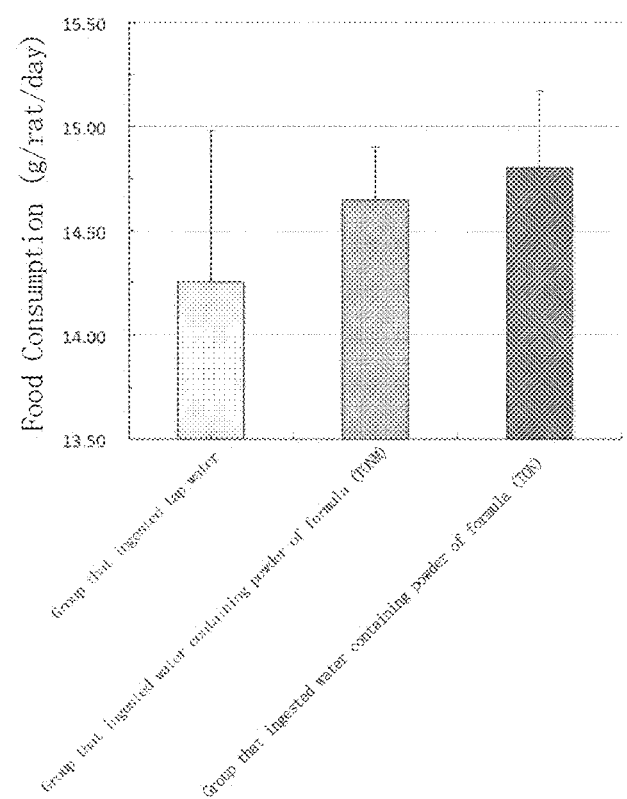
Figure 20:
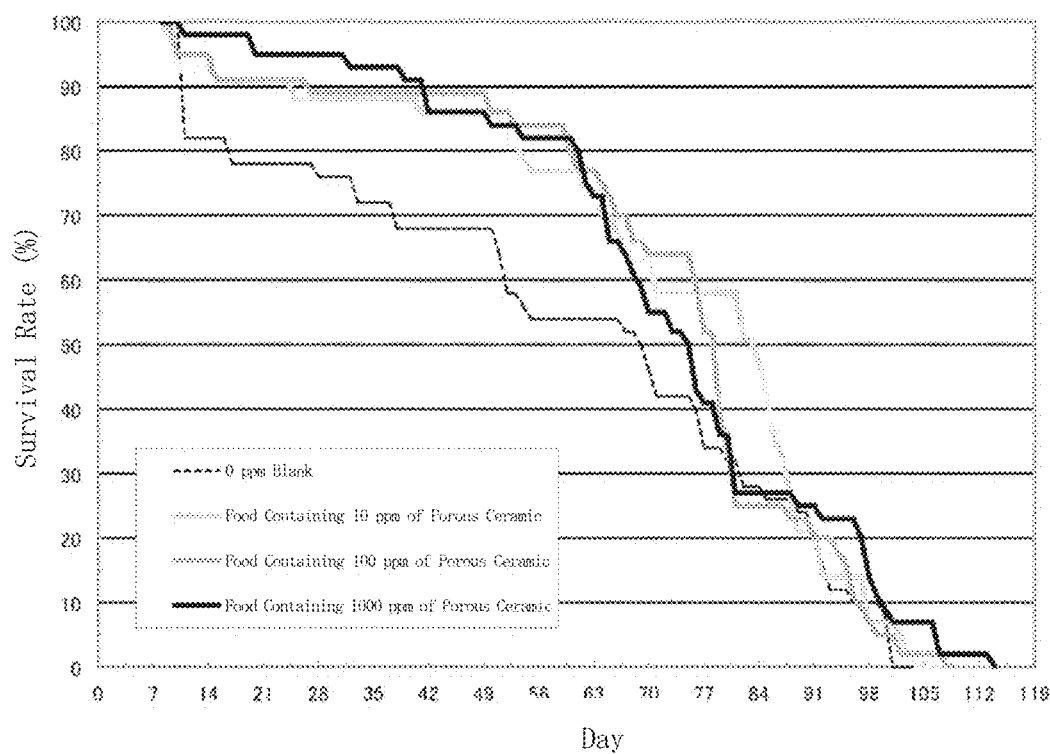
FIG. 20 is a graph illustrating changes in the survival rate of *Drosophila melanogaster* over time.

Commonly used anticancer agents even affect normal cells and have considerable side effects. In contrast, the porous ceramic of the present invention has a cancer-killing effect on cancer cells, while having no adverse effect on normal cells, or even favorably affecting normal cells. This has been demonstrated by the fact that the use of the porous ceramic of the present invention, as shown in FIG. 20, increased the survival rate at any of the wide-ranging stages of life, from youth to old age, and that the intake of the porous ceramic of the present invention improved appetite, as shown in FIGS. 18-1 and 18-2.

Cancers have been traditionally treated with a combination of chemical treatment (e.g., anticancer agent), surgical technique (surgery), radiation treatment, and immunotherapy in most cases. The porous ceramic of the present invention adds a new realm, physical action treatment, to the four fields of treatment. More specifically, it is strongly suggested that the cancer-killing effect of the porous ceramic of the present invention is due to the mechanism by which only cancer cells undergo tissue destruction, metabolic inhibition, etc., and are physically destroyed and killed. Additionally, toxicity was not observed in vivo, as shown in FIG. 6. The porous ceramic of the present invention appears to be able to serve as a physical action treatment with few side effects for patients. It is also suggested from this physical action treatment that the treatment is useful for numerous types of cancer because tissue destruction occurs regardless of the type of cancer. In fact, the results of experiments at cell levels using the porous ceramic of the present invention demonstrated the validity.

Currently, although therapeutic drugs, such as anticancer agents for cancers, are available, there are no preventive drugs that have proven to be clearly effective. The methyl radical confirmed with the porous ceramic of the present invention may play a role in preventing the collapse of epigenetics (preventing abnormal gene expression, such as cancer, different from the normal state) such as DNA methylation. This indicates that the porous ceramic of the present invention shows promise as a continuously usable cancer preventive drug with no toxicity or side effects.

Test Example 9: Neurodegenerative Disease

Typical examples of neurodegenerative diseases include polyglutamine disease, Alzheimer's disease, and Parkinson's disease. Polyglutamine disease causes conditions such as involuntary movement and gait disorder. Academic research has found that Alzheimer's disease develops conditions such as memory disorder and dementia because of the blocking of the nutrient supply from blood vessels to nerve cells and accumulation of denatured protein, such as amyloid β (waste products excreted from brain neurons), caused by the failure of discharge to blood. Parkinson's disease is a progressive disease that develops pathological conditions including dopamine shortage and relative increases in acetylcholine in the brain.

Figure 10:
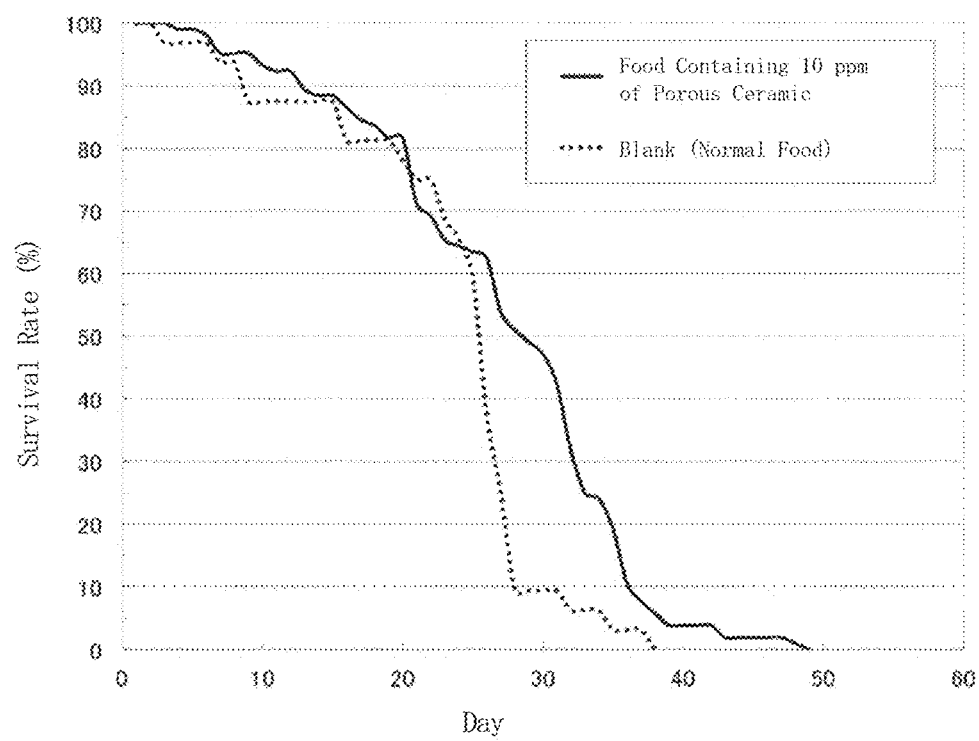
FIG. 10 is a graph illustrating changes in the survival rate over time of Parkinson's disease fly models.

FIG. 10 shows the results of the survival rate of Parkinson's disease fly models measured by examining the difference between the intake of the porous ceramic of the present invention and no intake of the ceramic. The ceramic powder of Production Example 20 as a typical example of formula (OBNM) was mixed with agar to give a concentration of 10 ppm, and fed to fly models. The survival rate of the flies was measured to examine the pharmacological effect. The control group, which was given normal food containing no porous ceramic of the present invention, abruptly started to die on day 25, and all were dead on day 37. The test group, which was given the porous ceramic of the present invention, exhibited a prolonged lifetime of 48 days. The results suggest that the porous ceramic of the present invention can be an effective therapeutic drug for Parkinson's disease.

Test Example 10: Influenza Virus

Viral infections can be prevented by producing neutralizing antibodies against viruses in the body; however, viruses are prone to mutation, and preventive-treatment, vaccines, must be made every time viruses mutate. Viruses parasitize in cells to proliferate, and anti-viral drugs to inhibit their growth are therefore available, but these drugs do not directly destroy the viruses. Thus, an in vitro test was performed using the porous ceramic of the present invention to examine virus inactivation.

Figure 11:
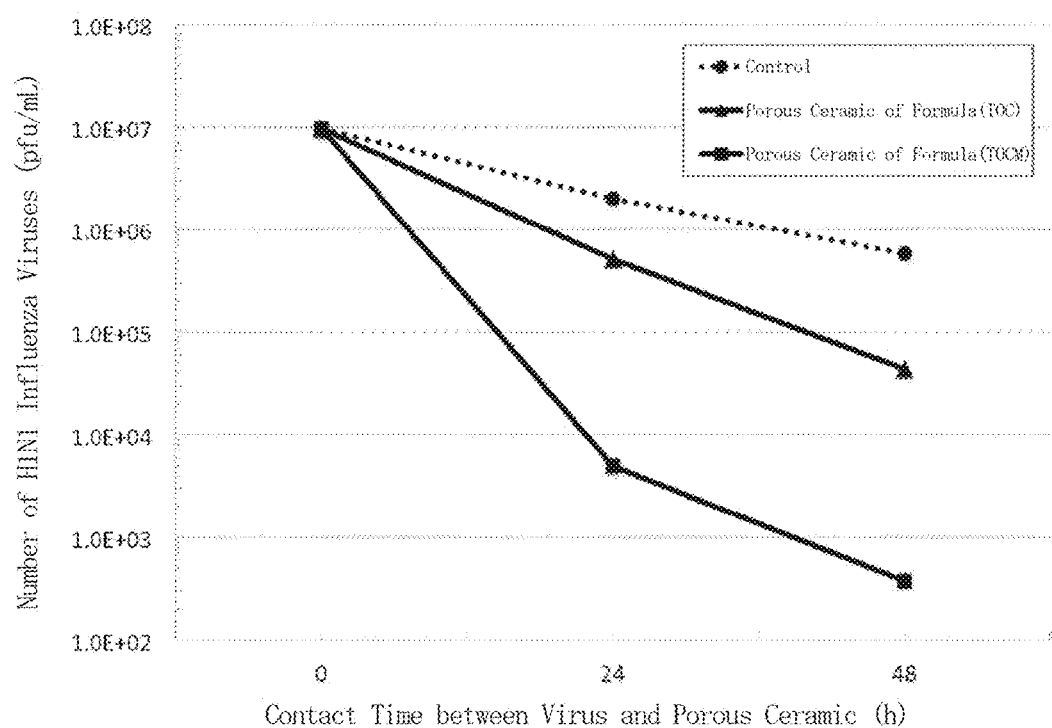
FIG. 11 is a graph illustrating the results of an inactivation test on an influenza virus.

0.2 mL of a virus solution containing influenza A virus (H1N1) as a target virus was seeded to culture solutions (20 mL each) to which the ceramic powder of Production Example 2 or Production Example 4 was added to give a concentration of 1000 ppm as a typical example of the porous ceramic represented by formula (TOC) or formula (TOCM). These reaction solutions were maintained in a thermostatic bath at 25° C. for 24 hours and 48 hours to allow for contact between the virus and the ceramic powder. Thereafter, 5 mL of each reaction solution was collected and filtered through a filter to separate each ceramic powder from its virus solution. These virus solutions were used as an original solution for measuring infectivity, and the infectivity was measured. After each original solution was diluted 10 times stepwise with PBS, 50 µL of each original solution or its diluted virus solution and 50 µL of a suspension of MDCK cells in 5% FBS-containing DMEM were inoculated into a 96-well microplate. Thereafter, they were cultured in a $CO_2$ incubator at 37° C. for 4 days. After culture, cytopathic effect (CPE) caused by viral proliferation was observed, and the virus infectivity ($TCID_{50}$/mL) was determined using the Reed-Muench technique and converted to the number of viruses (pfu/mL). FIG. 11 shows the results.

As compared with the control, which contained no porous ceramic of the present invention, the samples containing the porous ceramic of the present invention all exhibited decreases in the number of viruses. In particular, the porous ceramic of formula (TOCM) exhibited a decrease to about 1/400 after 24 hours, and even 1/1550 after 48 hours, as compared with the control. This indicates that the porous ceramic of the present invention is sufficiently effective against influenza A virus (H1N1). This test was also performed on influenza A virus (H3N2) using the same porous ceramics under the same conditions, and the test produced substantially the same results as those for influenza A virus (H1N1).

As noted above, the porous ceramic of the present invention had effective action on influenza viruses regardless of their type (subtype). This implies that the porous ceramic of the present invention is essentially different from currently available vaccines and anti-viral drugs in action mechanism, and has action to physically destroy viruses. In addition, since the porous ceramic does not biologically inhibit viruses but physically destroy them, the porous ceramic is assumed to be even able to handle mutated viruses. The use of this sort of virus inactivation technique shows promise for rapid mass production of safe inactivation vaccines in the event of a pandemic outbreak.

Test Example 11: HIV

Figure 12:
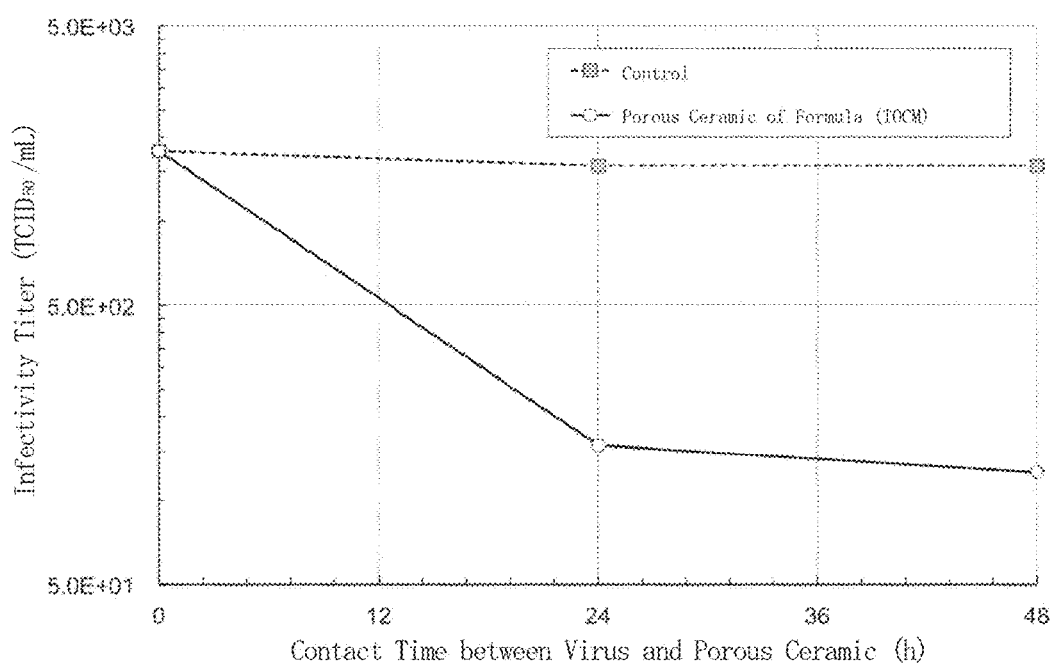
FIG. 12 is a graph illustrating the results of an inactivation test on HIV.

The human immunodeficiency virus (HIV-1) as a target virus in BSL3 level was placed in culture solutions containing 1000 ppm of the ceramic powder of Production Example 4 as a typical example of the porous ceramic represented by formula (TOCM) for 24 hours and 48 hours to allow them to come into contact with each other. These virus solutions were used as an original solution for measuring infectivity, and the infectivity was measured. The process for inactivation and the infectivity measurement experiment were the same as in Test Example 10. FIG. 12 shows the results. The control, which contained no porous ceramic of the present invention, had an infectivity of 1580 ($TCID_{50}$/mL) even after 48 hours, which was practically the same as the initial value. The test sample containing the porous ceramic of the present invention exhibited a decrease in the infectivity to 158 ($TCID_{50}$/mL) after 24 hours from the initial value of 1785 ($TCID_{50}$/mL), and a further decrease to 126 ($TCID_{50}$/mL) after 48 hours.

The results suggest that the porous ceramic of the present invention is sufficiently effective against the human immunodeficiency virus. Thus, the porous ceramic shows promise in use to prevent the development of acquired immunodeficiency syndrome (AIDS) in HIV carriers, who are estimated to have reached 50 million worldwide today.

Test Example 12: Glycometabolism, Liver Function, Lipid Abnormality, and Obesity Increases in cholesterol and neutral fat in the blood significantly increase the mortality rate from cardiovascular diseases or cerebrovascular diseases, largely caused by dyslipidemia or arteriosclerosis. Decreased extravascular exudation of sugar due to vascular degeneration, such as arteriosclerosis, elevates blood glucose levels, causing diabetes. The joint committee of the Japanese Cancer Association and the Japan Diabetes Society reports that diabetes has a high causal relation with cancer development.

Figure 13:
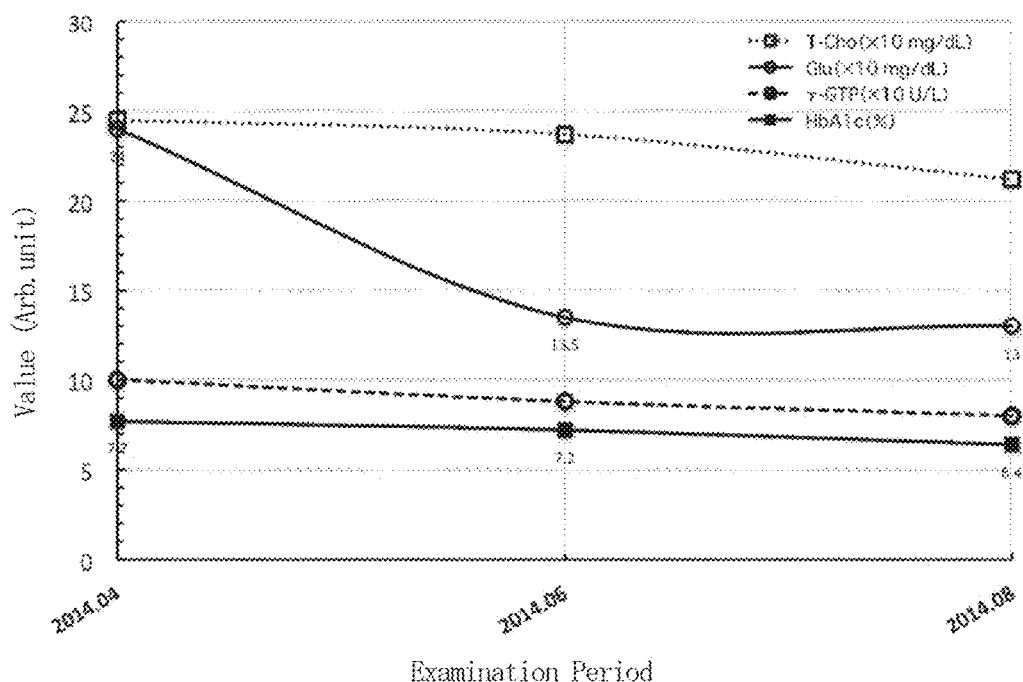
FIG. 13 is a graph illustrating changes in the blood test results (T-Cho, Glu, γ-GTP, and HbA1c) over time.

FIG. 13 shows the test results of the blood glucose level (Glu) and hemoglobin A1c (HbA1c) of subject D1 (male in his 60s) with problems of glycometabolism function. FIG. 13 also shows the test results of the total cholesterol (T-Cho) and γ-glutamyl transpeptidase (γ-GTP). One ceramic molded body of Production Example 2, as a typical example of the porous ceramic represented by formula (TOC), was added to 2 L of tap water, and subject D1 orally ingested this 2 L of processed water every day since the test in April 2014. The results of the test in August 2014, 2 months after the start of the intake, showed that Glu decreased by almost half from 240 to 130, which still remained higher than the normal range (75 to 105) though, and that HbA1c also decreased from 7.7 to 6.4, approaching its normal range (4.6 to 6.2). This indicates that the porous ceramic of the present invention has medicinal effects to improve glycometabolic function.

Figure 14:
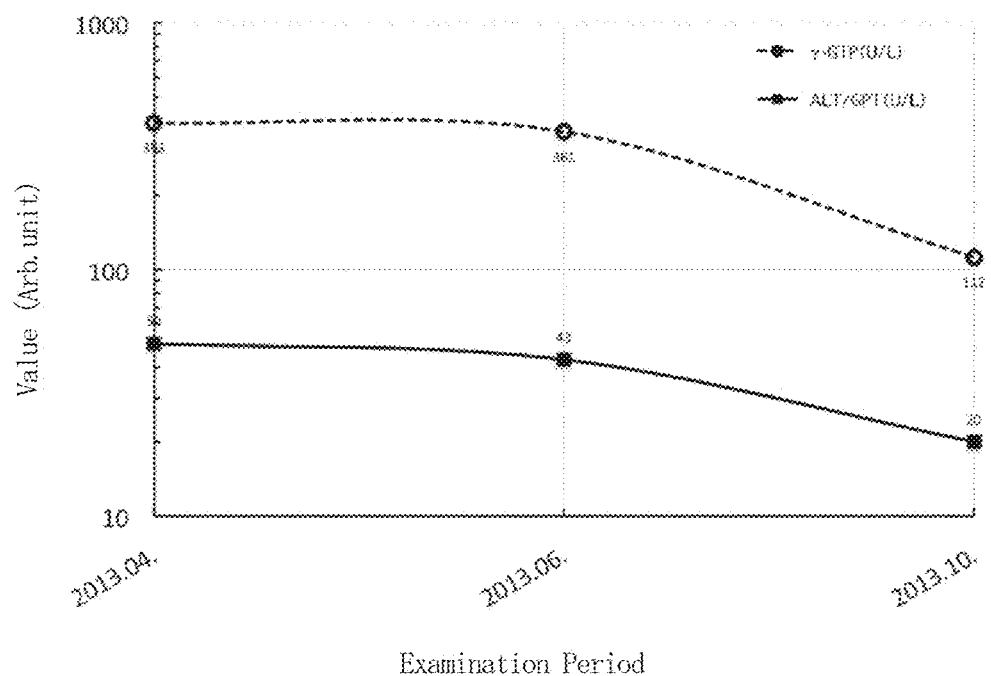
FIG. 14 is a graph illustrating changes in the blood test results (γ-GTP and ALT/GPT) over time.

FIG. 14 shows the test results of the alanine aminotransferase (ALT/GPT) and γ-glutamyl transpeptidase (γ-GTP) of subject D2 (male in his 40s) with impaired liver function. The test results in April and June 2013 both showed these levels to be higher than normal levels. One ceramic molded body of Production Example 4, as a typical example of the porous ceramic represented by formula (TOCM), was added to 2 L of tap water, and subject D2 orally ingested this 2 L of processed water every day since the test in June 2013. The results of the test in October 2013, 4 months after the start of the intake, showed that ALT/GPT significantly declined from the initial level of 50 to 20, falling within the normal range (4 to 36). The γ-GTP also significantly improved from the initial level of 393 to 112, falling by about ⅓, which is still higher than the normal range (4 to 68) though. This indicates that the porous ceramic of the present invention has medicinal effects to improve liver function.

Figures 1, 15:
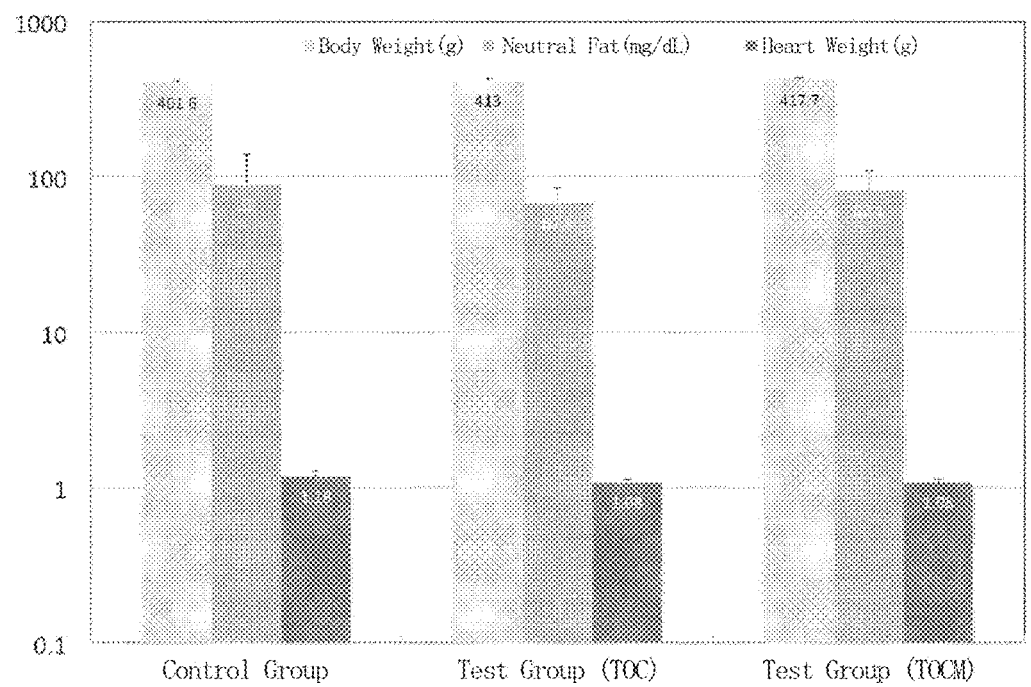
Figures 2, 15:
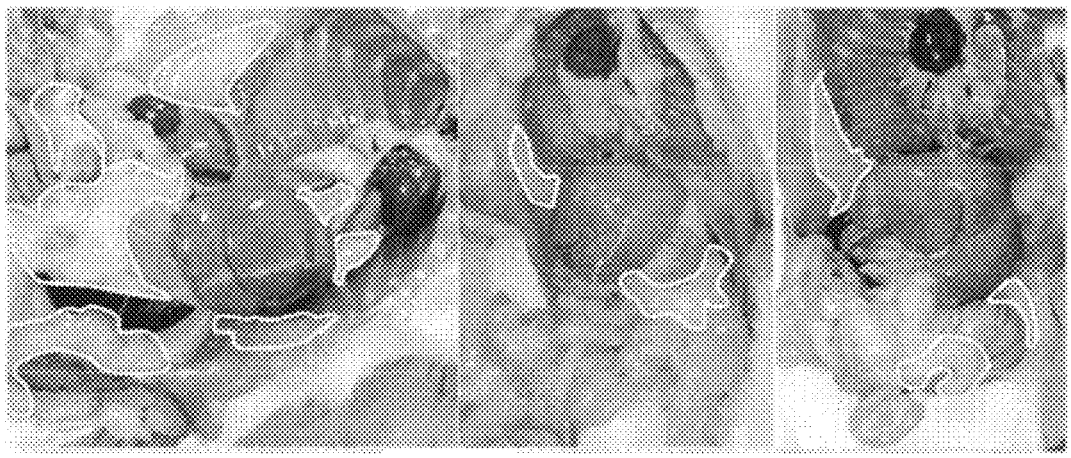
Figures 3, 15:
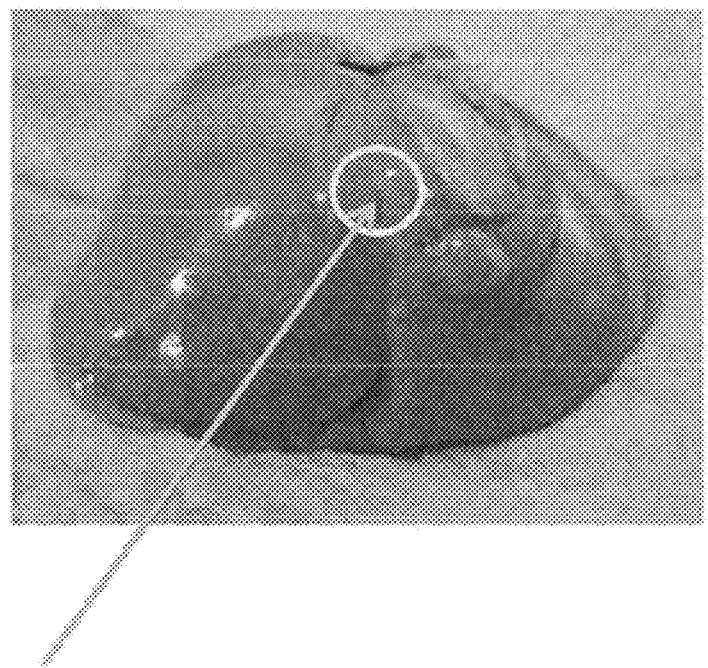

The porous ceramic of the present invention was also examined as to whether it has an effect on neutral fat (TG), which is one marker of dyslipidemia. Rats were fed a 4% high-cholesterol diet for one month under the following conditions: N=8, food amount of 14 g/rat/day for all rats. While being given the same amount of food, the control group was allowed to drink tap water freely, and the test groups were allowed to freely drink powder-containing water prepared by adding 100 ppm of the ceramic powder of Production Example 2 or Production Example 4, as a typical example of the porous ceramic represented by formula (TOC) or formula (TOCM), to tap water. FIG. 15-1 shows the results of their body weight, neutral fat in the blood, and heart weight determined from tissue dissection after one month. The test groups had a higher body weight than the control group, and given the fact that the rats were fed the same amount of food, this indicates that the intake of the porous ceramic of the present invention increased absorption efficiency. In general, an increase in body weight due to high absorption efficiency, as in this case, also increases neutral fat in the blood. In this experiment, however, the control group exhibited the highest neutral fat, with the groups that ingested the porous ceramic of the present invention exhibiting lower neutral fat levels. This is most probably because the intake of the porous ceramic of the present invention increased basal metabolism, which led to higher consumption of neutral fat.

The results indicate that when fed the porous ceramic of the present invention, the rats with lipid abnormality caused by a high-cholesterol diet exhibited high absorption efficiency and increased body weight, but more notably exhibited decreases in neutral fat as a result of activated metabolism. This was also confirmed with the dissected tissues shown in FIG. 15-2. The parts surrounded by a white line in FIG. 15-2 indicate body fat tissues. While the control group exhibited a noticeable increase in fat, the test groups that ingested the porous ceramic of the present invention exhibited obviously lower fat deposition. This suggests that the porous ceramic of the present invention can be a preventive and therapeutic drug for dyslipidemia and obesity. FIG. 15-1 also shows their heart weight. The control group exhibited a more enlarged heart than the test groups.

FIG. 15-3 shows a typical liver tissue of the control group. While the control group showed a fatty liver, 3 of 8 rats also showed the development of a swollen hepatic tissue around the diaphragm connection (the part indicated by an arrow in the figure). In contrast, 1 out of 8 rats in the test group that was fed the porous ceramics represented by formula (TOC) exhibited a small amount of pathological lesion, and none of the 8 rats in the test group that was fed the porous ceramics represented by formula (TOCM) exhibited such lesion. Because the intake of the porous ceramic of the present invention increases absorption efficiency, the ceramic may be usable as a preventive and therapeutic drug for obesity.

Test Example 13: Obesity and Slimming Effect

The Ministry of Health, Labour and Welfare defines obesity as having a body mass index (BMI) of 25 or more with health problems or potential health problems, or with excess visceral fat. Obesity causes complications that extend to 11 clinical conditions, such as diabetes, hypertension, and lipid abnormality.

Subject E (male in his 60s) with a BMI of 30, which translates to obesity (class 2) in the obesity criteria of the Japan Society for the Study of Obesity, volunteered in this experiment. One ceramic molded body of Production Example 4, as a typical example of the porous ceramic represented by formula (TOCM), was added to 2 L of tap water. Subject E orally ingested this processed water in an amount of 1 L/day, and a tablet containing 2 mg of the ceramic powder of Production Example 4 at a dose of 2 tablets/day together with drinking water every day. After 3 months, his BMI decreased to 24, which is within the normal range of 18 to 25, and this suggests that the porous ceramic of the present invention is potentially usable in the treatment of obesity.

Test Example 14: Skin Diseases

Figure 16:
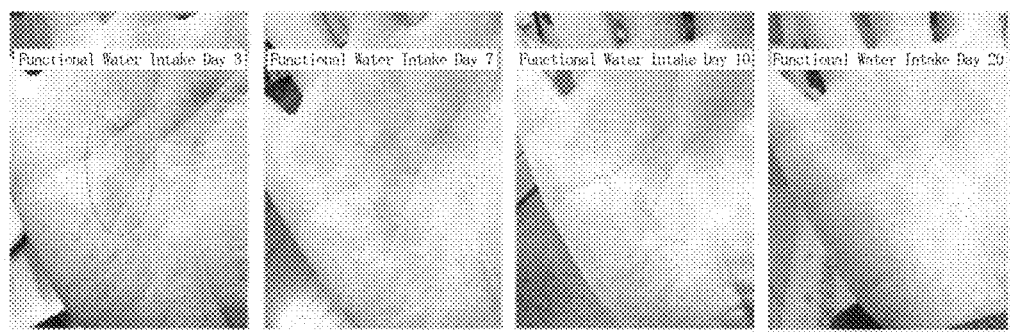
FIG. 16 shows photographs tracking the affected area of a patient diagnosed with psychosomatic skin disease.

There are many skin diseases, including inflammatory dermatosis, such as psychosomatic skin diseases, tinea pedis skin disease, psoriasis vulgaris, and bedsore. Subject F (male in his 60s), who had a psychosomatic skin disease, was administered the porous ceramic of the present invention. Subject F orally ingested a tablet containing 10 mg of the ceramic powder of Production Example 19 at a dose of one tablet/day together with drinking water every day. At the same time, subject F also orally ingested processed water prepared by adding a portion (5 g) of the ceramic molded body of production Example 18 to 2 L of tap water in an amount of 1 L/day. FIG. 16 shows the healing process of the patient. Although the effect was minimal on day 3 from the administration, the skin disease was almost fully healed on day 20. The same effect was also confirmed with patients with tinea pedis skin disease or psoriasis vulgaris.

Multiple subjects with inflammatory dermatosis such as bedsore in a senior care home had their affected areas sprayed with processed water prepared by adding a portion (5 g) of the ceramic molded body of Production Example 18 to 500 cc of tap water at a frequency of about 2 to 3 times/day, and then the affected areas were allowed to dry naturally. After three days, the healing effect was observed. The effect was probably because of its sterilizing action on microorganisms responsible for inflammation.

Test Example 15: Alcohol-Decomposition Accelerating Action

Figure 17:
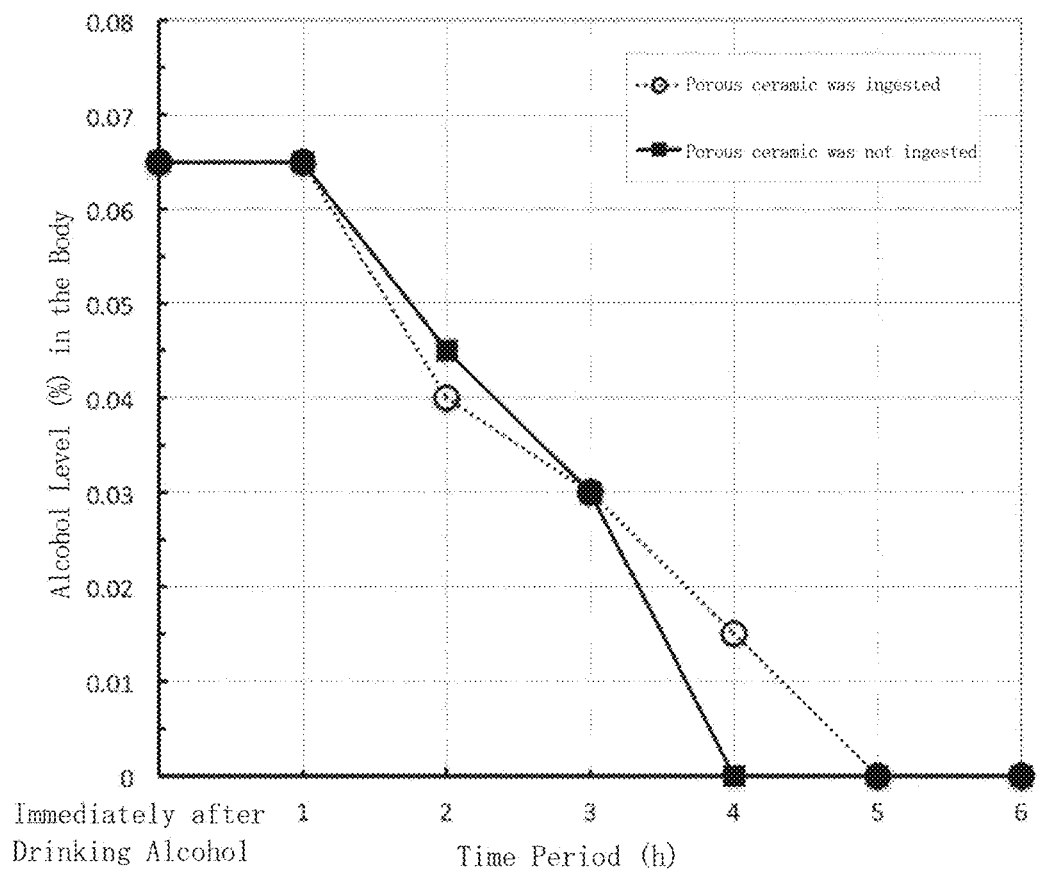
FIG. 17 is a graph illustrating changes in alcohol level in the body over time.

An examination was performed to determine whether the porous ceramic of the present invention accelerates alcohol decomposition after alcohol intake. The ceramic powder of Production Example 2, as an example of the porous ceramic represented by formula (TOC), was added to water to prepare powder-containing water. The alcohol decomposition rate of subject G (male in his 20s) was measured both when he orally ingested the powder-containing water before alcohol intake (test case) and when he did not ingest the powder-containing water (control case) before alcohol intake. The alcohol decomposition rate was measured two times with an interval of two weeks for each case. In the test case, subject G orally ingested 100 cc of the powder-containing water containing 3.5 mg of the ceramic powder of Production Example 2 before drinking alcohol, and 15 minutes later, subject G started to drink 360 mL of Japanese sake with an alcohol content of 15 to 16% and drank all of it in 15 minutes. Immediately after drinking, the alcohol level in the body was measured over time with a BEX alcohol detection kit in both cases. FIG. 17 shows the results.

After one hour from alcohol intake, both cases exhibited substantially the same alcohol level in the body, but after three hours, the alcohol level in the body started to decrease more rapidly in the test case than in the control case. After four hours, while the alcohol level in the body in the test case reached 0%, 0.015% of alcohol remained in the body in the control case. The same alcohol-decomposition accelerating action was observed in the intake of powder-containing water containing the ceramic powder of Production Example 1, Production Example 5, Production Example 9, Production Example 13, Production Example 6, Production Example 10, or Production Example 14, as a typical example of the porous ceramic represented by formula (TC), formula (TB), formula (TN), formula (TS), formula (TOB), formula (TON), or formula (TOS). The same effect was also observed in the intake of processed water prepared by adding the ceramic molded body, and in the intake of a tablet containing the ceramic powder.

As noted above, the oral intake of the porous ceramic of the present invention before alcohol intake accelerated alcohol decomposition in the body. This is probably because the intake of the porous ceramic of the present invention increased the blood flow, and thus accelerated the alcohol metabolism rate in the liver. The increased blood flow was presumably caused by nitrogen monoxide (NO), which is one of the endothelium-derived vascular-relaxing factors. Probably, after only the aqueous portion of the ceramic powder-containing aqueous suspension is absorbed into the body, the secondary reaction shown in Test Example 4 produces NO in the body during the metabolization process. At any rate, since the intake of the porous ceramic of the present invention accelerates alcohol decomposition and metabolization, the porous ceramic may be usable, for example, as a therapeutic drug for acute alcohol poisoning or a preventive drug for hangover.

Reference Example 1

The results revealed that the oral intake of powder-containing water containing the ceramic powder of the present invention before alcohol intake accelerates decomposition of alcohol in the body after alcohol consumption, as compared with when the powder-containing water is not taken. To show that the decrease in the alcohol level was caused by accelerated metabolization in the body, an in vitro test was performed to confirm that the porous ceramic of the present invention added to an aqueous alcoholic solution does not directly decompose the alcohol. For porous ceramic, the ceramic powder of Production Example 2 was used as in Test Example 15.

7 mL of ethanol with a purity of 99.5% was mixed with 493 mL of ion-exchanged water to prepare an aqueous alcoholic solution, and the alcohol content was measured over time with an alcoholometer (alcohol content: 0 to 10%, precision 0.1%) both when the ceramic powder of Production Example 2 was present and when absent. The initial alcohol content of the aqueous alcoholic solution was 1.7%. The ceramic powder of Production Example 2 was added to a test sample to give a concentration of 100 ppm. After 4 days, the control (the ceramic powder not added) had an alcohol content of 1.2% and the test sample also had the same alcohol content, 1.2%.

This indicates that the porous ceramic of the present invention does not directly decompose alcohol, revealing that the intake of the porous ceramic of the present invention produces a blood-flow-increasing effect and/or alcohol-decomposition-accelerating effect in the body, not directly decomposing alcohol.

Test Example 16: Appetite Stimulating Effect

Decreased appetite caused by illness may decrease physical strength, which may worsen the illness, leading to a vicious cycle. Thus, an examination was performed to determine whether the intake of the porous ceramic of the present invention has an appetite-stimulating effect. The test was performed using Fischer rats, allowing the rats to freely ingest food. The rats were divided into three groups: one control group, which was given tap water, and two test groups, which were given powder-containing water prepared by adding the ceramic powder of Production Example 10 or Production Example 12, as a typical example of the porous ceramic represented by formula (TON) or formula (TONM) to tap water so as to give a concentration of 100 ppm. FIG. 18-1 shows the total food consumption of each group during 45 days. FIG. 18-2 shows their food consumption converted as per rat per day.

Both the total food consumption and the food consumption per rat per day were higher in the test groups than in the control group. In particular, the group that was given the water containing the ceramic powder of Production Example 10 as an example of the porous ceramic represented by formula (TON) exhibited the highest appetite stimulating effect, which was about 4% higher than that of the control group. This indicates that the intake of the porous ceramic of the present invention produces an appetite-stimulating effect.

Test Example 17: Pylori Bacterium

Diseases that involve *Helicobacter pylori* include chronic gastritis, gastric ulcer, duodenal ulcer, and stomach cancer. The *Helicobacter pylori*, in particular, correlates to stomach cancer, and the World Health Organization (WHO) designates *Helicobacter pylori* as an unequivocal carcinogen on the grounds of epidemiological research. While antibiotics have been primarily used to clean away *Helicobacter pylori* so far, the emergence of drug-resistant bacteria and their side effects have been considered issues.

An in vitro test was performed to examine the antibacterial capability of the porous ceramic of the present invention against *Helicobacter pylori* (JCM 12093). *Helicobacter pylori* was subjected to microaerobic culture containing 5% equine defibrinated blood at 37° C.±1° C. for 6 to 8 days, and suspended in physiological saline, followed by adjustment of the bacterial count to $10^3$/mL to $10^4$/mL, thereby preparing a test solution of the bacterium.

Agar plates containing 5% equine defibrinated blood were used as a medium. For the test samples, a medium containing 100 ppm of the ceramic powder of Production Example 1 or Production Example 3, as a typical example of the porous ceramic represented by formula (TC) or formula (TCM), was used. For the control, a medium containing no porous ceramic was used. 0.1 mL of the test solution of the bacterium was smeared onto each of the three media, and microaerobic culture was performed at 37° C.±1° C. for a predetermined period of time (5 to 7 days), followed by counting of growing colonies on the agar plates. Table 6 shows the results.

TABLE 6

Effect of the Porous Ceramic on *Helicobacter pylori*

| | | Concentration (ppm) | Number of Growing Colonies | |
|---|---|---|---|---|
| | | | Day 5 of Culture | Day 7 of Culture |
| Test Sample | Production Example 3: Formula (TCM) | 100 | 0 | 0 |
| | Production Example 1: Formula (TC) | 100 | 703 | 748 |
| Control | No Addition of Porous Ceramic | 0 | 1900 | 1980 |

The porous-ceramic-containing test samples both exhibited decreases in the number of growing colonies than the control containing no porous ceramic. The *Helicobacter pylori* had all already been killed on day 5 of the culture, in particular, in the use of the porous ceramic of Production Example 3 represented by formula (TCM).

With the backing of the results above and the biological non-toxicity, an in vivo test using the porous ceramic of Production Example 4 represented by formula (TOCM) was performed in two voluntary subjects H1 (male in his 30s) and H2 (male in his 50s) who were *pylori*-positive in a breath test performed beforehand (using UBT). Voluntary subject H1, whose Δ level was 6.9% (the normal level is less than 2.5%) in the breath test beforehand, orally ingested the ceramic powder of Production Example 4 at a dose of 5 mg/day together with drinking water for 2 weeks, and his Δ level decreased to 1.1%, showing success in clearing the *Helicobacter pylori*. Voluntary subject H2, whose Δ level was previously 28.6%, orally ingested the same ceramic powder at a dose of 30 mg/day together with drinking water for one week, and then continuously ingested the same ceramic powder at a dose of 60 mg/day together with drinking water for two weeks. His Δ level decreased to 1.9%, and the *Helicobacter pylori* were successfully cleared away in this case as well. The results indicate that the oral intake of the porous ceramic of the present invention can clear away *Helicobacter pylori* without the use of antibiotics.

Test Example 18: Periodontal Bacteria

There are many diseases caused by periodontal bacteria and cavity-causing bacteria, such as pyorrhea and tooth decay. The 2012 vital statistics reported by the Ministry of Health, Labour, and Welfare ranked pneumonia as the third highest cause of death, following cancer and cardiovascular diseases. Of the types of pneumonia, in particular, aspiration pneumonia is thought to be caused partly by periodontal bacteria and cavity-causing bacteria, and effective disinfectants need to be developed. Some research papers also report the causal relation between ulcerative colitis and cavity-causing bacteria.

An in vitro test was performed on periodontal bacteria using the porous ceramic. One ceramic molded body of Production Example 8, as a typical example of the porous ceramic represented by formula (TOBM), was added to 1 L of pure water to prepare a culture solution. *Porphyromonas gingivalis* (PG) was then added to the culture solution to give a concentration of $3.49 \times 10^6$. After culture at 37° C. for 24 hours, the number of the bacteria was counted. Table 7-1 shows the results. While the bacterial count of the pure water culture solution containing no porous ceramic was about $10^3$ CFU/mL, the bacterial count of the culture solution containing the porous ceramic was 0 CFU/mL.

TABLE 7-1

In Vitro Test of the Porous Ceramic on Periodontal Bacterium *Porphyromonas gingivalis*

| | Bacterial Count (CFU/mL) | |
|---|---|---|
| | At the Start | After 24 Hours |
| Production Example 8 | $3.49 \times 10^6$ | 0 |
| Pure Water | $3.49 \times 10^6$ | $2.48 \times 10^3$ |

In the same manner, one ceramic molded body of Production Example 12, as a typical example of the porous ceramic represented by formula (TONM), was added to 1 L of pure water to prepare a culture solution. PG was then added to the culture solution to give a concentration of $2.22 \times 10^6$. After culture at 37° C. for 24 hours, the number of the bacteria was counted. Table 7-2 shows the results. The bacterial count was 0 CFU/mL when the culture solution containing the porous ceramic was used.

TABLE 7-2

In Vitro Test of the Porous Ceramic on Periodontal Bacterium *Porphyromonas gingivalis*

| | Bacterial Count (CFU/mL) | |
|---|---|---|
| | At the Start | After 24 Hours |
| Production Example 12 | $2.22 \times 10^6$ | 0 |
| Pure Water | $2.22 \times 10^6$ | $2.52 \times 10^3$ |

Since the results indicate that the porous ceramic of the present invention is useful as a disinfectant for periodontal bacteria, the ceramic appears to be usable as a preventive drug and/or therapeutic drug for periodontal diseases.

Test Example 19: Cavity-Causing Bacteria

An in vitro test was performed to examine the effect of the porous ceramic of the present invention on *Streptococcus mutans* MT8148, which can develop tooth decay although its toxicity is low. The ceramic powder of Production Example 20, as a typical example of the porous ceramic represented by formula (OBNM), was added to pure water to give a concentration of 100 ppm and the ceramic powder was also added to phosphate buffer to give a concentration of 100 ppm, thereby preparing two types of powder suspensions as test samples. For the control, pure water and a phosphate buffer were used as media without adding the porous ceramic. MT8148 was added to each medium to give a concentration of $10^8$, and the bacteria were cultured at 37° C. for 24 hours, followed by measuring the bacterial counts. Table 8-1 shows the results. The bacterial count after 24 hours varied by $10^5$ or more depending on whether the porous ceramic was present.

TABLE 8-1

In Vitro Test of the Porous Ceramic on *Streptococcus mutans* MT8148 (Cavity-Causing Bacterium)

| | Bacterial Count (CFU/mL) | |
|---|---|---|
| | At the Start | After 24 Hours |
| Production Example 20, Pure Water | $1 \times 10^8$ | 40 |
| Production Example 20, Phosphate Buffer | $1 \times 10^8$ | 50 |
| Pure Water | $1 \times 10^8$ | $5 \times 10^7$ |
| Phosphate Buffer | $1 \times 10^8$ | $5 \times 10^6$ |

The same test was performed under the same conditions using 100 ppm of the ceramic powder of Production Example 18 as a typical example of the porous ceramic represented by formula (OBN). Table 8-2 shows the results. After 24 hours, the test samples both exhibited a bacterial count of 0 CFU/mL, indicating complete destruction of the bacteria.

TABLE 8-2

In Vitro Test of the Porous Ceramic on *Streptococcus mutans* MT8148 (Cavity-Causing Bacterium)

| | Bacterial Count (CFU/mL) | |
|---|---|---|
| | At the Start | After 24 Hours |
| Production Example 18, Pure Water | $1 \times 10^7$ | 0 |
| Production Example 18, Phosphate Buffer | $1 \times 10^7$ | 0 |
| Pure Water | $1 \times 10^7$ | $5 \times 10^6$ |
| Phosphate Buffer | $1 \times 10^7$ | $5 \times 10^5$ |

Endocarditis is one of the diseases in which cavity-causing bacteria are involved. Highly toxic SA31 is reported as a contributing factor in the development of severe endocarditis, and antibiotics have been primarily used as a drug to eradicate the bacterium. Antibiotics, however, have many drawbacks, such as side effects and emergence of drug-resistant bacteria due to heavy use, and disinfectants to replace antibiotics have been desired. Thus, an in vitro test was performed to examine the effect of the porous ceramic on SA31. The ceramic powder of Production Example 4, as a typical example of the porous ceramic represented by formula (TOCM), was added to pure water to give a concentration of 100 ppm, and the ceramic powder was also added to phosphate buffer to give a concentration of 100 ppm, thereby preparing two types of powder suspensions as test samples. For the control, pure water and a phosphate buffer were used as media without adding the porous ceramic. SA31 was added to each medium to give a concentration of $10^8$, and the bacteria were cultured at 37° C. for 24 hours, followed by measuring the bacterial count. Table 9-1 shows the results. After 24 hours, the test samples both exhibited a bacterial count of 0 CFU/mL, indicating complete destruction of the bacteria.

TABLE 9-1

In Vitro Test of the Porous Ceramic on *Streptococcus mutans* SA31 (Cavity-Causing Bacterium)

| | Bacterial Count (CFU/mL) | |
| --- | --- | --- |
| | At the Start | After 24 Hours |
| Production Example 4, Pure Water | $1 \times 10^8$ | 0 |
| Production Example 4, Phosphate Buffer | $1 \times 10^8$ | 0 |
| Pure Water | $1 \times 10^8$ | $5 \times 10^7$ |
| Phosphate Buffer | $1 \times 10^8$ | $5 \times 10^6$ |

The same test was performed under the same conditions using 100 ppm of the ceramic powder of Production Example 2 as a typical example of the porous ceramic represented by formula (TOC). As shown in Table 9-2, after 24 hours, the test samples both exhibited a bacterial count of 0 CFU/mL, indicating complete destruction of the bacteria.

TABLE 9-2

In Vitro Test of the Porous Ceramic on *Streptococcus mutans* SA31 (Cavity-Causing Bacterium)

| | Bacterial Count (CFU/mL) | |
| --- | --- | --- |
| | At the Start | After 24 Hours |
| Production Example 2, Pure Water | $1 \times 10^7$ | 0 |
| Production Example 2, Phosphate Buffer | $1 \times 10^7$ | 0 |
| Pure Water | $1 \times 10^7$ | $5 \times 10^6$ |
| Phosphate Buffer | $1 \times 10^7$ | $5 \times 10^5$ |

Since the results indicate that the porous ceramic of the present invention is useful as a disinfectant for cavity-causing bacteria, such as MT8148 and SA31, the ceramic appears to be usable as a preventive drug and/or therapeutic drug for, for example, tooth decay.

Figures 1, 19:
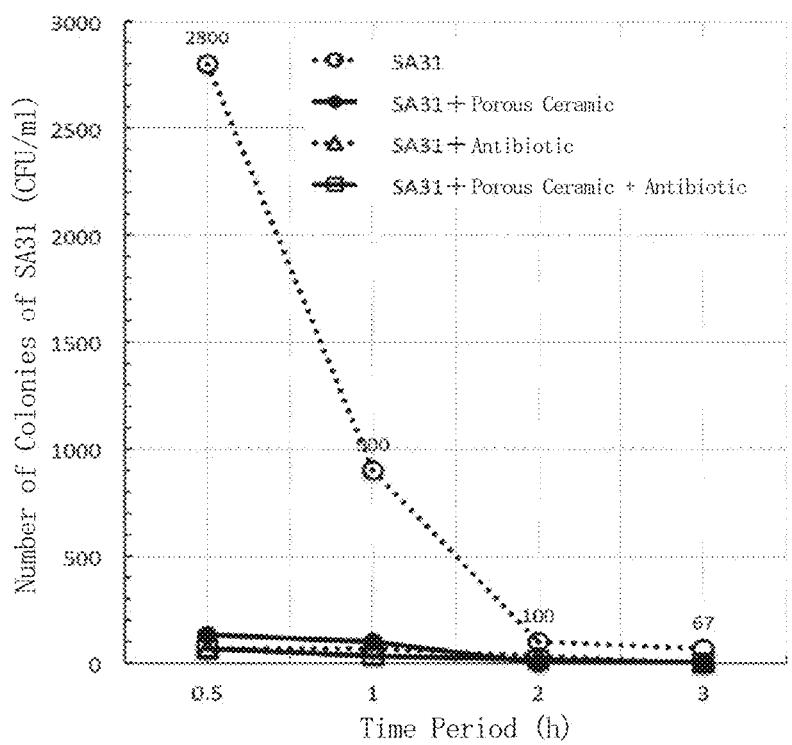
Figures 2, 19:
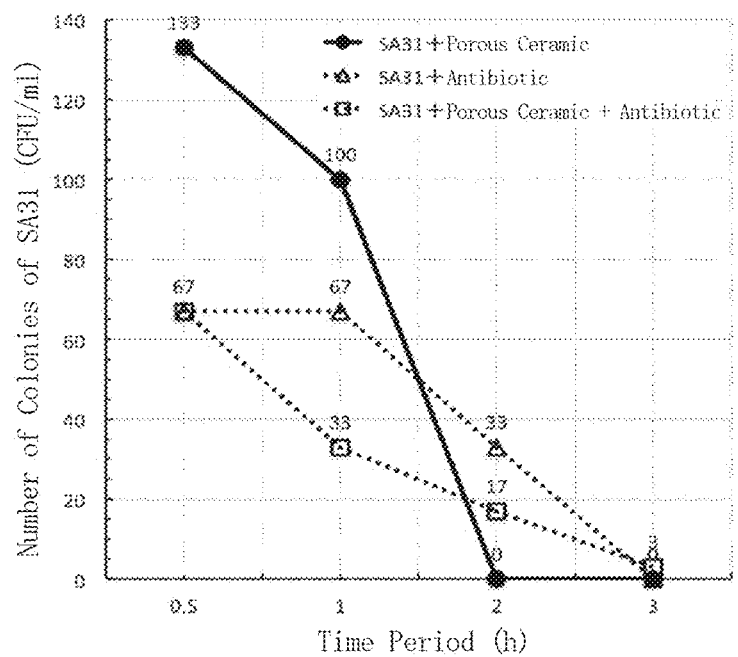

Subsequently, an in vivo test was performed using healthy rat models. This test was performed using four groups of rats by adding the following to the blood of the rats: physiological saline to which $10^8$ of SA31 was added; a physiological saline aqueous solution obtained by adding $10^8$ of SA31 and the ceramic molded body of Production Example 4 represented by formula (TOCM); physiological saline obtained by adding $10^8$ of SA31 and an antibiotic; and a physiological saline aqueous solution obtained by adding $10^8$ of SA31, an antibiotic, and the ceramic molded body of Production Example 4 represented by formula (TOCM). The blood was collected at a predetermined time interval and cultured, followed by measuring the number of SA31 colonies. FIG. 19-1 shows the results. FIG. 19-2 is a magnified view of part of FIG. 19-1. SA31 in the blood of healthy rats is ingested by white blood etc., and thus decreases without proliferation. The use of the porous ceramic or antibiotic, however, decreased SA31 to 1/20 or less in 30 minutes, exhibiting its medicinal effect. In particular, the use of the physiological saline aqueous solution obtained by adding the porous ceramic decreased SA31 to 0 CFU/mL in 2 hours, showing its faster eradication effect than the antibiotic, which eradicated SA31 in 3 hours.

The results indicate that the porous ceramic of the present invention may be usable not only to eradicate SA31 but also as a severity-preventive drug and/or therapeutic drug for endocarditis caused by SA31. In addition, due to its higher pharmacological effect than antibiotics, the porous ceramic shows promise as a replacement for antibiotics and also for preventing multidrug-resistant bacteria.

Test Example 20: Improved Survival Rate

A survival rate measurement examination employed a wild-type reference line of *Drosophila melanogaster* (Canton S) that emerged from the pupa with n=100 (50 males and 50 females) for statistical work. Food and water were fed to the *drosophila* through agar. The agar for the control group was composed of dry yeast, cornmeal, glucose, agarose, propionic acid, Bokinin (preservative), agar, and water. For food, the test groups were given agar containing 10 ppm, 100 ppm, or 1000 ppm of the ceramic powder of Production Example 20 as a typical example of the porous ceramic represented by formula (OBNM), in addition to the components of the agar for the control group. The obtained data were analyzed with the Kaplan-Meier method to study the survival rate, and with the log-rank test to examine whether there is any significant difference between the two groups (the control group and the test group) in their survival rate. Regarding the test period, the test was performed until the survival rate reached 50% at which the sample food was assumed to have been sufficiently eaten, thus producing the effect.

The Kaplan-Meier method is a survival analysis performed by calculating the survival rate every time any subject dies. The log-rank test examines the difference in survival rate between two groups calculated by the Kaplan-Meier method. Specifically, the null hypothesis (i.e., there being no difference between two groups in their survival rate) is tested. When the results of the test indicate that the probability is significantly low under the null hypothesis, the null hypothesis is rejected. A cutoff value of the probability at which the null hypothesis is rejected must be set. This cutoff value is called "risk ratio ($\alpha$)" because the value may potentially reject the null hypothesis by mistake, even if the hypothesis is true. The probability of obtaining test statistic $\chi$ under the null hypothesis is indicated as "P" and is called the "p-value." If set as $\alpha$, the p-value is the value at which the null hypothesis is rejected. Thus, in general, when $P \le 0.05$, a result is statistically significant, while when $P \le 0.01$, a result is statistically extremely significant. Table 10 shows the results.

TABLE 10

Log-rank Test Results

| | $X^2$ | P Value (Upper Probability) | $X^2$ (0.95) |
| --- | --- | --- | --- |
| Male | | | |
| Control Group vs. Test Group 10 ppm | 1.84 | 0.175 | 3.84 |
| Control Group vs. Test Group 100 ppm | 5.76 | 0.016 | 3.84 |
| Control Group vs. Test Group 1000 ppm | 4.75 | 0.029 | 3.84 |
| Female | | | |
| Control Group vs. Test Group 10 ppm | 0.37 | 0.544 | 3.84 |
| Control Group vs. Test Group 100 ppm | 1.04 | 0.307 | 3.84 |

TABLE 10-continued

Log-rank Test Results

|  | $X^2$ | P Value (Upper Probability) | $X^2$ (0.95) |
|---|---|---|---|
| Control Group vs. Test Group 1000 ppm | 0.33 | 0.565 | 3.84 |

Note:
$P \leq 0.05$ is statistically significant, and $P \leq 0.01$ is statistically extremely significant Table 10 indicates that of the control group and 3 test groups (10 ppm, 100 ppm, and 1000 ppm), the male test group that was given a sample food containing 100 ppm or 1000 ppm of the porous ceramic of the present invention exhibited a survival rate considered to be statistically significant as compared with the control group.

The statistically processed data of this experiment also reveal that the survival rate of the test groups composed of male *Drosophila melanogaster* improved more than that of the control group. FIG. 20 shows changes in the survival rate. On and after day 8, by which the subjects had been habituated, the survival rates of the test groups were clearly higher than that of the control group. In particular, from day 10 to day 88, due to the effect of the intake of the porous ceramic-containing agar, the test groups exhibited high survival rates. The survival rate on or after day 88 was substantially the same between the control group and the test groups; this is because as aging progressed, the subjects became inactive and stopped eating agar, thus not taking the porous ceramic. However, after day 88, while the subjects of the control group were all dead on day 101, those of the test groups were all dead on day 104, day 108, and day 114 in increasing order starting from the lower concentration of the porous ceramic, indicating their prolonged lifetime. This reveals that even after day 88, from which the subjects did not ingest the porous ceramic, the ceramic still had an effect on the subjects for a maximum of nearly two weeks.

The results appear to reveal that the intake of the porous ceramic did not extend their lifetime, but maintained various biological functions of the test groups better than in the control group, extending the good health span (healthy life expectancy), thereby lowering the mortality rate. This means that excellent quality of life can be maintained even later in life. In particular, there was a sharp contrast during the time period from day 71 to day 81 between the test group that was given agar containing 10 ppm of the porous ceramic and the control group. While the survival rate of the test group remained 58%, the survival rate of the control group declined from 42% to 32%. When this is translated to humans, the population that lives a healthy life until about 80 years of age is considered to have increased by 26%. The average life expectancy of Japanese males is about 80 years, and their healthy life expectancy is said to be about 70 years. Due to health problems, it is currently difficult for Japanese males to live a healthy life during the decade after reaching 70 years of age, but the intake of this porous ceramic appears to contribute to the extension of their healthy life expectancy.

As noted above, the intake of the porous ceramic of the present invention maintains the health of biological functions, thus increasing the likelihood of living a healthy life. Although the exact reaction mechanism in vivo cannot be confirmed, the intake of the porous ceramic of the present invention has been found to be capable of improving the survival rate. In particular, the intake of the porous ceramic of the present invention has been found to be capable of decreasing not only the age-related mortality rates in old age but also capable of increasing the survival rate at any stage of life from youth to old age.

Test Example 21: Flow-Mediated Dilation

The strain on blood vessels due to hypertension, diabetes, etc. damages vascular endothelial cells and impairs the function for preventing arteriosclerosis. This causes cholesterol and fat to accumulate on the endothelial lining, allowing plaque to develop, which then leads to blood flow disturbance. The rupture of the plaque also generates a blood clot, which leads to circulatory system diseases such as myocardial infarction and cerebral infarction. Although thrombolytics are available as a preventive drug for these diseases, the drugs are not an essential treatment, and improvement in vascular endothelial conditions is important.

The flow-mediated dilation (FMD) test provides an indication for arteriosclerosis, hypertension etc., and is used to measure the dilation of blood vessels. Declines in vascular endothelial cell function decrease the generation of NO, which is a vasodilatory factor, thereby lowering FMD. A rough guide for the normal level is 6% or more, and less than 5% suggests damage to blood vessel endothelia. The FMD of subject I (male in his 30s) was measured before and after the intake of the porous ceramic. One ceramic molded body of Production Example 3, as a typical example of the porous ceramic represented by formula (TCM), was added to 2 L of tap water to prepare processed water, and subject I ingested the processed water in an amount of 1 L/day everyday. While his FMD before the intake was as low as 5.5%, his FMD significantly improved to 11.5% after 6-month intake. The other porous ceramics of the present invention also exhibited a similar FMD improving effect. The results indicate that the porous ceramic of the present invention has an excellent effect in improving the vascular endothelial conditions.

Test Example 22: Intestinal Regulation

Subject J1 (male in his 60s) with paraplegia from spinal cord nerve injury had constipation that was assumed to be due to gait inability and nerve damage, and was given a suppository every 10 days to induce defecation. Subject J1 then ingested processed water prepared by adding a portion of the porous ceramic solid of Production Example 16 (mass: 5 g) as a porous ceramic to 2 L of tap water in an amount of 2 L/day. After day 3, subject J1 defecated almost every day, exhibiting an improvement in constipation caused by nerve damage. This indicates that the porous ceramic of the present invention has a beneficial effect on not only intestinal regulation but also the nerve system. At the same time, defecation odor substantially decreased.

Subject J2 (male in his 60s), who had had diarrhea every day since his childhood, also ingested the processed water described above in an amount of 1 L/day, and on and after day 3, intestinal regulation from diarrhea to normal feces was observed. When subject J2 stopped drinking the processed water, he started to have diarrhea a week later as before. This indicates that the improvement in defecation returning from diarrhea to normal feces was due to the porous ceramic of the present invention.

Test Example 23: Spasm

The fundamental factors of spasms remain largely unknown. Of long-distance expressway drivers, subject K (male in his 60s) was chosen, who complained of a spasm in his right leg caused by constantly pressing the accelerator and its long-term persistence once it developed. He ingested about 200 cc of processed water prepared by adding a portion of the porous ceramic solid of Production Example 15 (5 g) as a typical example of the porous ceramic to 2 L of tap water, when he had the spasm. As a result, the spasm subsided in 5 to 10 minutes after the oral intake of the processed water. This appears to be due to increased blood flow as described in Test Example 21.

Test Example 24: Muscle Fatigue

Twenty voluntary subjects were divided into substantially equal groups, taking into consideration their gender, age, and level of daily physical activity. The subjects of the control group drank 1 L of commercially available bottled water, and the subjects of the test group drank powder-containing water prepared by adding the ceramic powder of Production Example 12, which had a mean particle size of 2 μm, to 1 L of commercially available bottled water to give a concentration of 10 ppm. The subjects of both groups walked 10 km round trip (5 km each way, including a slope), during which the subjects drank their water little by little. Immediately after this, the next day, and the day after that (3 days), the subjects answered a survey about muscle fatigue and muscle pain. 10 subjects of the control group and 9 subjects of the test group had muscle fatigue immediately after the exercise, showing little difference between them. However, the next day and the day after that, while 8 subjects of the control group had muscle pain, none of the test group had muscle pain, showing a significant difference. The results indicate that the intake of the water containing the ceramic powder can soothe fatigue in a shorter time and remove muscle pain that generally occurs the next day.

Subject L (male in his 60s), who practices golf for about 3 hours per week, had muscle fatigue accompanied by muscle pain on days after practice. He drank processed water prepared by adding one ceramic molded body of Production Example 12 as a porous ceramic to 2 L of tap water in an amount of 2 L/day and practiced golf as usual. Unlike before, he had no muscle pain on or after the next day, and also had no muscle fatigue as a subjective symptom.

Test Example 25: Paste Dentifrice, Gum Agent

In addition to the essential components (an abrasive and a foaming agent), 5% by weight of the ceramic powder of Production Example 8 (mean particle size: 2 μm) as an example of the porous ceramic, which serves as a medicinal component, was added to prepare a paste dentifrice. Subject M (male in his 20s) brushed his teeth with the dentifrice twice a day. As a result, the use of the dentifrice exhibited not only decreases in periodontal bacteria and cavity-causing bacteria as demonstrated in Test Example 18 and Test Example 19, but also exhibited a preventive effect on inflammation caused by these microorganisms, an accelerated tartar-controlling effect due to radical decomposition, and a preventive effect on build-up of plaque, such as biofilm. The radicals also facilitated the decomposition of tar stains on teeth, indicating the higher removing effect of the dentifrice than that of typical dentifrices. When subject M chewed gum prepared by adding 1% by weight of the ceramic powder of Production Example 8 (mean particle size: 2 μm) as a porous ceramic, which serves as a medicinal component, twice a day, the same effects were observed.

Test Example 26: Liquid Dentifrice, Gargling Agent, Troche, Candy

Commonly available liquid dentifrices and gargling agents are usually intended to be spat out after use. The user may also gargle with water after using such a dentifrice or gargling agent, and the sterilizing effect decreases in either case. The processed water of the present invention can be used as a liquid dentifrice or a gargling agent, and may be swallowed after having it in the mouth and gargling, because it is not toxic, as described in Test Example 6. In addition, the processed water does not require rinsing after use, and thus its sterilizing effect does not decrease, having an advantage over typical liquid dentifrices and gargling agents in the longer-lasting effect. Moreover, teeth brushing may leave many unpolished parts, but the processed water penetrates periodontal pockets, suggesting that processed water may be able to delay or prevent the development of tooth decay and pyorrhea highly effectively.

Figure 21:
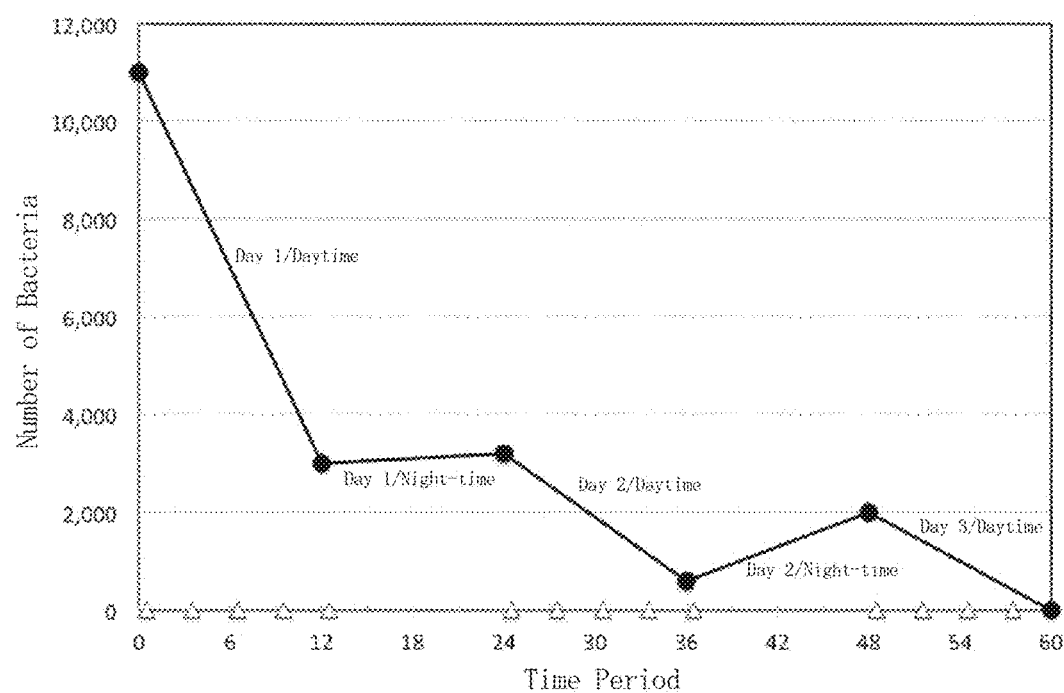
FIG. 21 is a graph illustrating a change in the count of *Streptococcus mutans* over time observed when gargling was performed.

To examine these effects, subject N, who had a relatively high mouth bacteria count, was chosen. Subject N used processed water prepared by adding one ceramic molded body of Production Example 4 as an example of porous ceramic to 2 L of tap water as a gargling agent. Unstimulated saliva of the subject was collected and the change in *Streptococcus mutans* bacterial count in an MSB medium was examined over time. FIG. 21 shows the results. Each day, the subject gargled after 9 am, after noon, after 3 pm, after 6 pm, and after 9 pm for 10 seconds each time (Δ in FIG. 21), and the saliva was collected every 12 hours a day (twice a day) to study the bacterial count. The saliva was collected immediately before gargling; thus, the bacterial count was not the count immediately after gargling. The bacterial count clearly decreased during the day as the subject gargled every 3 hours. Although bacteria typically proliferate during sleep, gargling with the processed water also exhibited a noticeable antiproliferative effect during night-time, and the bacterial count was reduced to zero at 9 pm on day 3 after the start of the experiment. Instead of the gargling agent, troches and candies containing about 0.1 mg to 1 mg of the ceramic powder of Production Example 4 per tablet were prepared, and the same test was performed using these troches and candies. The troches and candies had a more noticeable sterilizing effect than gargling because of their longer retention in the oral cavity.

The results indicate that the continuous use of a liquid dentifrice, a gargling agent, a troche, a candy, or the like that contains the porous ceramic of the present invention can maintain the cavity-causing bacteria count at substantially zero. Keeping the oral cavity clean is also expected to prevent other diseases caused by cavity-causing bacteria as shown in Test Example 19.

Test Example 27: Stomatitis

As revealed in Test Examples 18 and 19, the porous ceramic of the present invention can remove periodontal bacteria and cavity-causing bacteria. As is clear from the results of Test Examples 25 and 26, the paste dentifrice, gum agent, liquid dentifrice, gargling agent, troche, candy, and the like that contain the porous ceramic have a potent sterilizing effect.

Following the results, 3 subjects with stomatitis ingested a gum agent (one tablet per dose), a gargling agent (100 cc per dose), or a troche (one tablet per dose), all of which were the same as those described in Test Examples 25 and 26, three times a day, and all subjects made a full recovery in two days. This indicates that the porous ceramic of the present invention can serve as a therapeutic drug for stomatitis. Thereafter, the subjects continuously ingested the respective agents for 6 months, and they did not develop stomatitis during the period. This indicates that the porous ceramic of the present invention can serve as a preventive drug for stomatitis.

Test Example 28: Stratum Corneum

Subject P1 (female in her 60s) and subject P2 (male in his 60s), who had a hard stratum corneum on the heels, applied to their affected areas cotton impregnated with processed water prepared by adding one ceramic molded body of Production Example 4 as a porous ceramic represented by formula (TOCD) to 1 L of tap water multiple times a day, and after about 1 month, the stratum corneum decreased and healthy soft skin had returned.

Test Example 29: Breath Odor

Breath before and after intake of the processed water was measured with a breath checker (on a scale of 0 to 5). Five subjects who had level 4 or more before the intake of the processed water were chosen. The subjects gargled with the processed water of Test Example 28 for 10 seconds per gargle, 5 times a day, for 1 week, and then their breath was measured. As a result, 2 subjects showed a decrease in breath odor to level 0, with 3 subjects showing level 1. Since the oral intake of the processed water of Test Example 28 can sterilize the oral cavity as described in Test Example 26, the breath odor, largely caused by bacteria and bacteria metabolites, can be inhibited and prevented.

Test Example 30: Moisturizing Effect

Processed water prepared by adding one ceramic molded body of Production Example 4 as a typical example of the porous ceramic represented by formula (TOCM) to 1 L of tap water is usable as a cosmetic product excellent in cell absorption, although its detailed mechanism is unknown. In particular, the nanobubbles contained in the processed water are easily absorbed into the body. Multiple female subjects used this processed water as facial pack or skin toner. As a result, the processed water exhibited its excellent moisture retention and normalized dry skin, while significantly alleviating facial wrinkles. These results indicate that the porous ceramic of the present invention can prevent skin aging or improve aging skin.

Production Example 21: Method for Producing Food or Drink Product

Supplement

In addition to 2 mg of the ceramic powder of Production Example 3 as a typical example of the porous ceramic represented by formula (TCM), commonly used excipients (fillers) such as dextrin and crystalline cellulose, a binder such as silica, and an anti-adhesive agent such as calcium stearate (198 mg in total except for the ceramic powder) were mixed and compressed to prepare round tablets with a diameter of 8 mm and a weight of 200 mg. When these tablets are taken as a supplement, the daily intake of the ceramic powder is approximately the number of tablets calculated from a body weight factor of 0.2 mg/kg to 0.5 mg/kg. For example, if the body weight factor is 0.2 mg/kg, a person who weighs 60 kg ingests the ceramic powder in an amount of 12 mg/day, which is converted to 6 tablets. In some circumstances, film-coated tablets or sugar-coated tablets can also be suitably selected. Taking these tablets together with drinking water allows the porous ceramic to come into contact with water, thereby forming radical- and nanobubble-containing water.

Troches, Candy, Gum

About 0.1 mg to 2 mg of the ceramic powder of Production Example 7 was added to the starting materials of troches, candy, or gum, thereby preparing troches, candy, or gum.

Bread

Powders (hard flour, sugar, salt, dry yeast, and 100 ppm of the ceramic powder of Production Example 11) and warm water were added to a bowl and mixed, and the mixture was thoroughly kneaded for about 15 minutes. The dough was shaped into round pieces, covered with a wet towel, and allowed to rest at about 35° C. for primary fermentation until the dough rose about twice. The risen dough was pressed to release gas, and subjected to second fermentation for further rise. The fermented dough was then placed in a loaf pan and baked in an oven, which was preheated to about 200° C., for 10 minutes, thereby making bread. The porous ceramic did not inhibit the fermentation process, and the bread was normal.

Pancake

Eggs, some water, and 100 ppm of the ceramic powder of Production Example 15 were added to commercially available pancake powder and mixed, thereby preparing dough. The dough was baked on a hot plate preset to about 180° C., thereby making a pancake. The addition of about 100 ppm of the ceramic powder did not change the appearance or the texture of the pancake.

Chocolate

A commercially available chocolate starting material was melted by putting the bowl in hot water, and 10 ppm to 5000 ppm of the ceramic powder of Production Example 19 that was formed so as to have a mean particle size of 2 μm was added thereto. The mixture was stirred well, placed in a pan, and cooled, thereby preparing chocolate. The chocolate had the taste and texture as typical chocolate, with no strange feel.

Agar Jelly 2 g of commercially available agar powder was added to 300 cc of water with heating, and fully dissolved. Some sugar and 20 ppm of the ceramic powder of Production Example 19 that was formed so as to have a mean particle size of 2 μm were added thereto. The mixture was placed in a mold and cooled in a refrigerator, thereby preparing porous-ceramic-containing agar jelly.

Tofu 10 ppm of the ceramic powder of Production Example 19, formed so as to have a mean particle size of 2 μm, was added to commercially available soybean milk for preparing tofu (concentration: 13%), mixed, and heated to 70 to 75° C., followed by addition of bittern. The resultant was slowly mixed and allowed to stand for about 10 minutes until it solidified, thereby preparing tofu.

Beverage

The ceramic powder of Production Example 4, formed so as to have a mean particle size of 2 μm, was added to 500 cc of commercially available bottled drinking water to give various concentrations of 1 ppm to 5000 ppm. The prepared water with a concentration of 10 ppm or less was substantially transparent when observed with the naked eye. However, water with a concentration of more than 100 ppm had a color of gray to black as the concentration increased.

The ceramic powder of Production Example 4, formed so as to have a mean particle size of 2 μm, was added to beverages such as carbonated water, green tea, black tea, and coffee to give various concentrations of 1 ppm to 5000 ppm, thereby preparing porous-ceramic-containing beverages.

Test Example 31: Effects Produced by Intake of Food or Drink Product

The intake of the food or drink products prepared in Production Example 21 is expected to provide not only a survival-rate-improving effect and a biological-self-healing effect necessary to improve the survival rate, but also a preventive and inhibitory effect on aging and obesity, an effect in recovering from fatigue, an metabolism promotion effect on alcohol and the like due to increased blood flow, an appetite stimulation effect, etc. The intake of the food or drink products can also naturally decrease periodontal bacteria and cavity-causing bacteria, thus providing a preventive effect on various diseases associated with these bacteria.

Production Example 22: Chewable Tablet

A chewable tablet, a type of disintegrating tablet that is licked and melted in the oral cavity, was prepared. A filler and some other components that serve as a food starting material was added to 100 mg of the ceramic powder of Production Example 4 as a typical example of the porous ceramic represented by formula (TOCM) and compressed, thereby preparing chewable tablets having a diameter of 15 mm and a weight of 1 g.

Test Example 32: Measurement of Acetaldehyde in Expired Air

Figure 22:
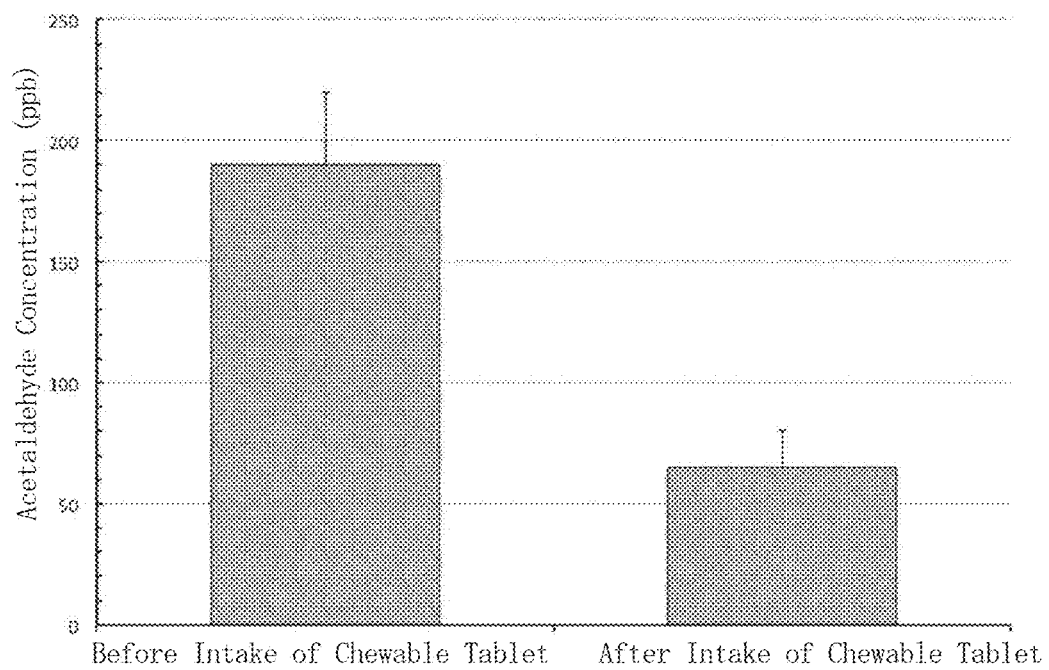
FIG. 22 is a graph illustrating a change in the acetaldehyde concentration in expired air before and after intake of chewable tablets.

Carcinogenic and hazardous acetaldehyde can be contained in the blood and expired air through alcohol drinking and smoking, and acetaldehyde is also now known to be chronically generated from the tongue plaque and the like. Ten healthy subjects orally ingested one chewable tablet of Production Example 22, taking about 5 minutes, and the acetaldehyde concentration in their expired air was measured before and after ingesting the tablet with sensor gas chromatography (FiS, SGEA-P2). FIG. 22 shows the results.

While the acetaldehyde concentration was 190±30 ppb before intake of the chewable tablet, the concentration after intake decreased by about ⅓ to 65±15 ppb. This indicates that daily intake of the porous ceramic of the present invention is expected to reduce the risk of developing cancer due to long-term exposure to a physiological concentration (a low concentration) of acetaldehyde.

A decrease in the acetaldehyde concentration was also confirmed with the intake of processed water prepared by adding the ceramic molded body of Production Example 4 as a typical example of the porous ceramic represented by formula (TOCM) to tap water. After intake, the acetaldehyde concentration decreased to ½ or less.

Test Example 33: Plaque Clinical Test and Change in Bacterial Count in the Oral Cavity (Antibacterial Effect)

Figure 23:
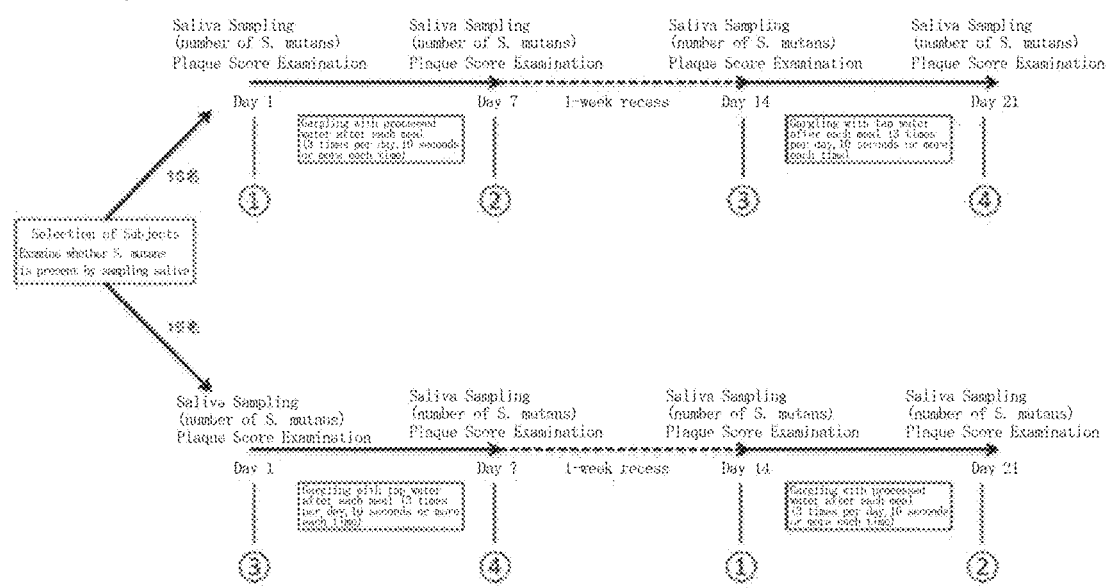
FIG. 23 is a graph illustrating the protocol of a clinical test for the effect of gargling on plaque formation.

Two types of gargle solutions (processed water obtained by adding the ceramic molded body of Production Example 4 as a typical example of the porous ceramic represented by formula (TOCM) to tap water and tap water for comparison) were used. The subjects gargled 3 times a day for 10 seconds or more each time. To determine the difference between the processed water and tap water, the plaque score (PS) and oral bacterial count in saliva were measured in a double-blind experiment. The subjects were allowed to brush their teeth as usual. With the number of subjects being n=30, the subjects were divided into 2 groups in accordance with the clinical protocol shown in FIG. 23. One group was scheduled to gargle with processed water for 1 week (Start (1) to End (2) in FIG. 23), not gargle for 1 week, and then gargle with tap water for 1 week (Start (3) to End (4) in FIG. 23), while the other group followed the schedule in reverse order. Plaque scoring (PS) and saliva sampling were performed at time points (1), (2), (3), and (4).

Figure 24:
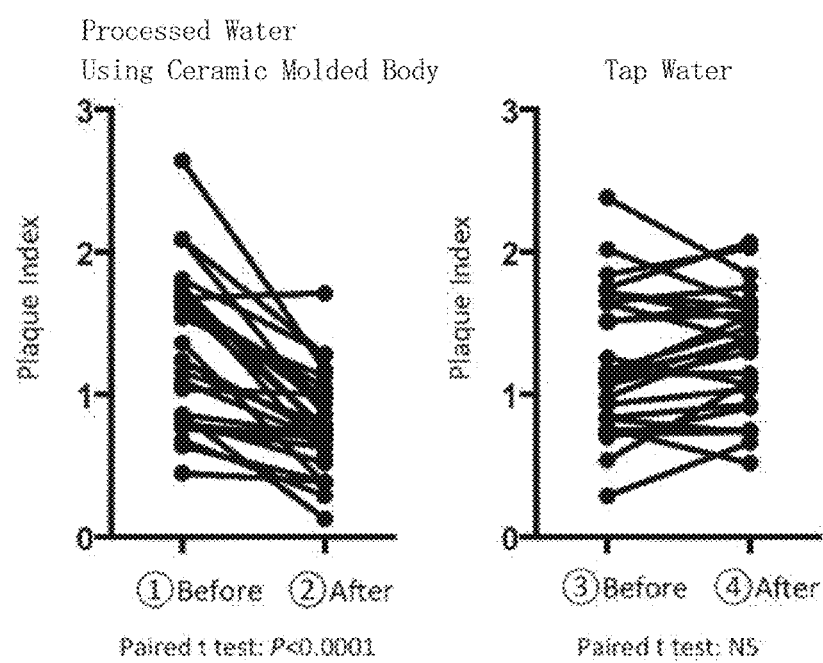
FIG. 24 is a graph illustrating changes in plaque index (plaque formation rate) made by gargling with processed water and tap water.

FIG. 24 shows plaque indices (PI) observed at Start (1) to End (2) of gargling with processed water shown in the clinical protocol and plaque indices (PI) observed at Start (3) to End (4) of gargling with tap water. The PI shown in the vertical axis was determined from the PS of each subject, with the highest PI being 3 (most contaminated) and the lowest PI being 0 (no plaque). While tap water did not show a constant trend of plaque formation rate, gargling with the processed water clearly decreased the plaque formation rate as compared with that before gargling. The results indicate that the statistically determined P-value for gargling with processed water was P<0.0001, showing a significant difference.

Figure 25:
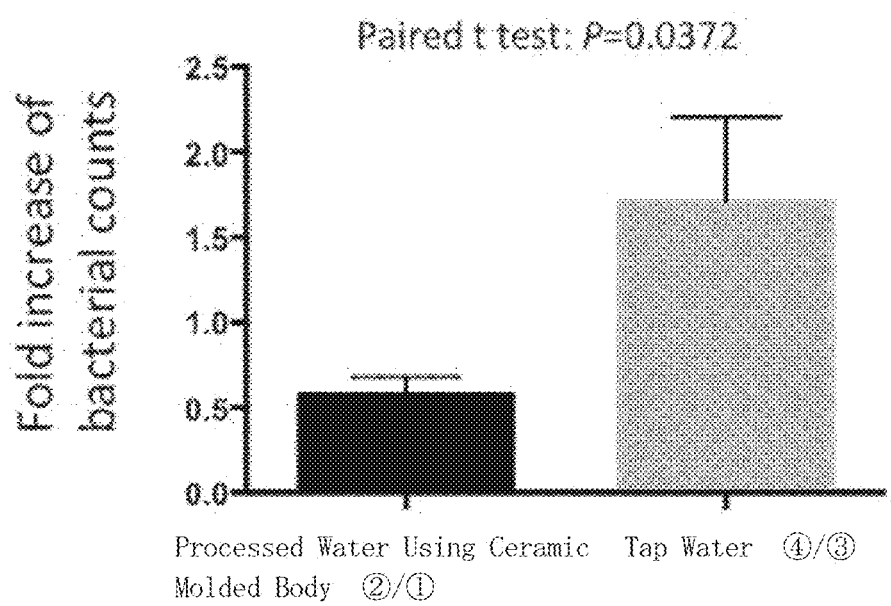
FIG. 25 is a graph illustrating changes in bacterial count in the oral cavity made by gargling with processed water and tap water.

FIG. 25 shows changes in bacterial count in the oral cavity. The change in bacterial count caused by gargling with processed water or tap water is shown by an index of "bacterial count after gargling (at time point (2) or (4))/bacterial count before gargling (at time point (1) or (3))." The index for no change in bacterial count is 1, and less than 1 indicates a decrease, while more than 1 indicates an increase. Gargling with processed water for 1 week decreased the oral bacterial count to about 60%; in contrast, gargling with tap water increased the oral bacterial count to 170%. This reveals that gargling with processed water has an antibacterial effect.

Test Example 34: Inhibition of Atopic Dermatitis Worsening

Mouse experiments confirmed that multiple bacteria, including *Staphylococcus aureus*, overgrow in the skin to disrupt the balance of resident microbiota, thereby causing inflammation (atopic dermatitis). A study was performed to examine the antibacterial effect of the porous ceramic of the present invention on *Staphylococcus aureus*.

A bacterium, *Staphylococcus aureus*, was cultured in a 4% NaCl-containing LB liquid medium at 37° C. for 24 hours. The cultured bacterium was seeded onto an agar medium, and a positive control and a test sample (concentration: 20 μL each) were individually applied to a paper disk placed in the center of a Petri dish. Ampicillin, which is a penicillin antibiotic, served as the positive control, and a suspension containing the ceramic powder of Production Example 4 as a typical example of the porous ceramic represented by formula (TOCM) served as the test sample. After culture at 37° C. for 36 hours, the antibacterial effect was indicated as the ratio of "Halo diameter/paper disk diameter." The larger the ratio, the greater the antibacterial effect on *Staphylococcus aureus*.

Figure 26:
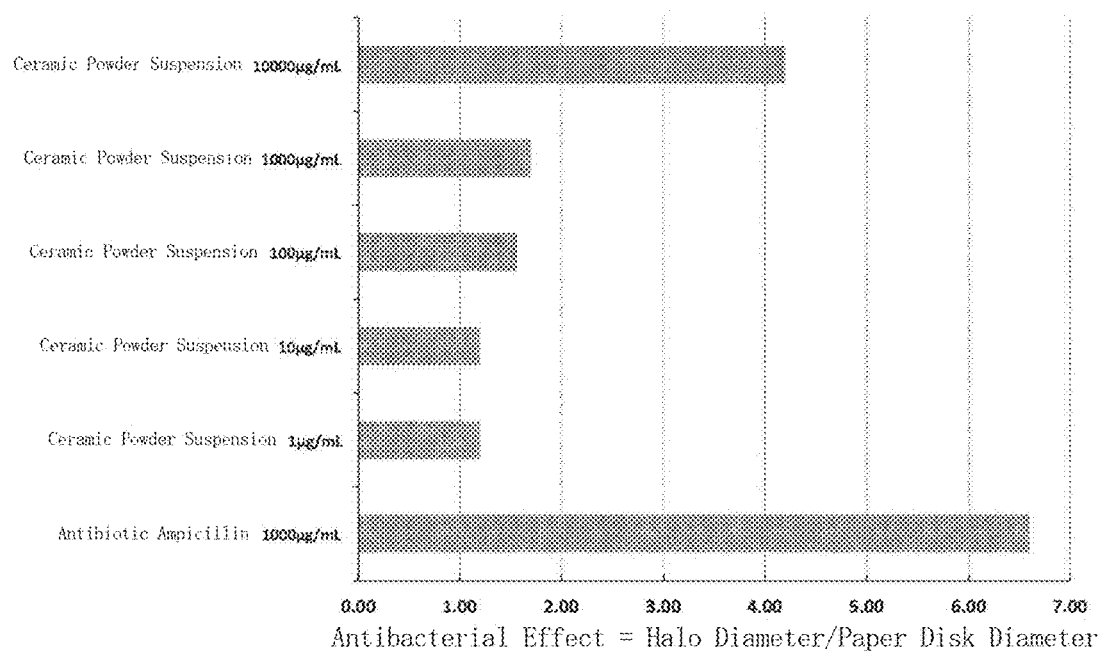
FIG. 26 is a graph illustrating the rate of an antibacterial effect on *Staphylococcus aureus*, which worsens atopic dermatitis.

FIG. 26 shows the results of the examination. The ceramic powder suspension with a concentration of 1 μg/mL to 10

μg/mL had a slight antibacterial effect, and the antibacterial effect increased as the concentration increased. When the concentration of the ceramic powder was 10000 μg/mL, the antibacterial effect rate was 4 or more, which was still far below that of the antibiotic ampicillin though. The results reveal that the ceramic powder has an antibacterial effect on *Staphylococcus aureus*.

Subsequently, subjects with atopic dermatitis sprayed the suspension onto their affected areas 6 times a day. This decreased itchiness and improved the conditions of their affected areas. The results reveal that the porous ceramic of the present invention can improve the symptoms of atopic dermatitis.

Test Example 35: Polyglutamine Diseases

Figure 27:
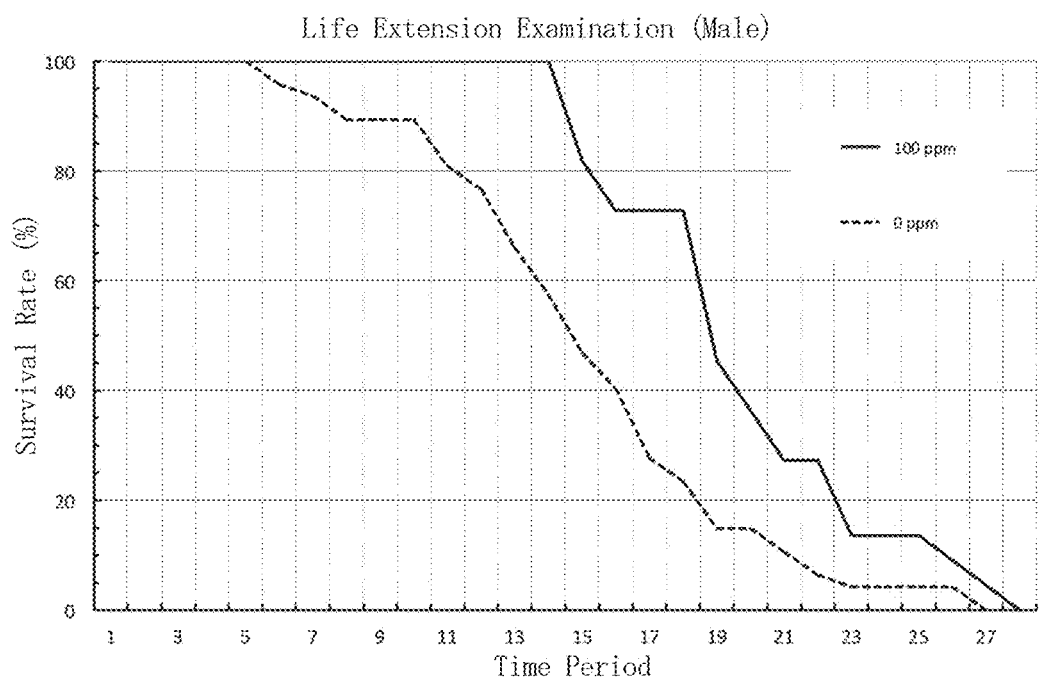
FIG. 27 is a graph illustrating changes in the survival rate of polyglutamine disease fly models over time.

Polyglutamine diseases, a group of neurodegenerative diseases, causes involuntary movement, gait disorder, etc. FIG. 27 shows the results of measuring the survival rate of polyglutamine disease fly models to examine the difference between the intake of the porous ceramic of the present invention and no intake of the ceramic. Flies were fed agar mixed with 100 ppm of the ceramic powder of Production Example 4 as a typical example of the ceramic represented by formula (TOCM), and the pharmacological effect was examined by observing the survival rate of the flies. Test group: n=22, control group: n=47.

While the control group fed a normal food containing no porous ceramic of the present invention had a mortality rate of 50% on day 14 and 100% on day 26, the test group given the porous ceramic of the present invention had a mortality rate of 50% on day 18 and 100% on day 27, showing their prolonged lifetime. The obtained data was analyzed with the Kaplan-Meier method to study the survival rate, and with the log-rank test to examine whether there was any significant difference between the control group and the test group in their survival rate. Regarding the test period, the test was performed until all of the subjects died. As a result, the p value was 0.005, which indicates that there was a statistically significant difference between the test group and the control group. When $P<0.05$, a result is determined to have a significant difference.

The results suggest that the porous ceramic of the present invention is usable as an effective therapeutic drug or preventive drug for polyglutamine diseases.

Test Example 36: Reduction in Mortality Rate of Calf

Fifty calves were allowed to freely drink processed water prepared by adding the ceramic molded body of Production Example 4 as a typical example of the porous ceramic represented by formula (TOCM) to tap water, and the calves did not develop diarrhea symptoms, showing a mortality rate of substantially 0% in the first year of life. As described above, giving processed water to livestock as drinking water improved their survival rate.

Test Example 37: Campylobacter Bacterium

An examination was performed to determine an antibacterial effect on *Campylobacter* bacterium, which causes food poisoning. The ceramic powder of Production Example 4 as a typical example of the porous ceramic represented by formula (TOCM) was added to Blood Agar Base No. 2 containing 5% equine defibrinated blood to give a ceramic powder concentration of 100 μg/mL. 15 mL of the mixture was added to a plastic Petri dish (diameter: 90 mm) and solidified, followed by application of 0.1 mL of a *Campylobacter* liquid (bacterial count: $10^3$/mL) thereto. After culture for 5 and 7 days, the number of growing colonies on the test plate was measured. The culture was performed at 35° C. in a microaerobic culture. As a control, the same test was performed without adding the ceramic powder.

Table 11 shows the results. When the porous ceramic of Production Example 4 represented by formula (TOCM) was used, *Campylobacter* bacterium was already dead on day 5 of culture. The same results were also confirmed with the porous ceramic of Production Example 3.

TABLE 11

Effect of the Porous Ceramic on *Campylobacter* bacterium

|  |  | Concentration (ppm) | Number of Growing Colonies per Plate | |
|---|---|---|---|---|
|  |  |  | Day 5 of Culture | Day 7 of Culture |
| Test Sample | Production Example 4: Formula (TOCM) | 100 | 0 | 0 |
| Control | No Addition of Ceramic Powder | 0 | 128 | 128 |

Test Example 38: Enteropathogenic *Escherichia Coli*

The microorganism responsible for enterohemorrhagic *Escherichia coli* infection is verotoxin-producing enteropathogenic *Escherichia coli*. An examination was performed to determine an antibacterial effect on 0157, which is one strain of enteropathogenic *Escherichia coli*. The ceramic powder of Production Example 4 as a typical example of the porous ceramic represented by formula (TOCM) was added to a nutrient agar medium to give a concentration of 100 μg/mL, and 20 mL of the mixture was added to a plastic Petri dish (diameter: 90 mm) and solidified, followed by application of 0.1 mL of an *Escherichia coli* liquid (serotype 015: H7, verotoxin I and II-producing strain, bacterial count: $10^3$/mL) thereto. After culture for 1 and 2 days, the number of growing colonies on the test plate was measured. The culture temperature was 35° C. As a control, the same test was performed without adding the ceramic powder.

Table 12 shows the results. When the porous ceramic of Production Example 4 represented by formula (TOCM) was used, about half of the enteropathogenic *Escherichia coli* were dead on day 1 of culture, but the rest even survived on day 2.

Thus, the concentration of the ceramic powder was increased by 10 times to 1000 μg/mL. Table 13 shows the results. Except for the concentration, the culture conditions were all the same as in the examination above. As a result, all of the enteropathogenic *Escherichia coli* were already dead on day 2 of culture. The same results were confirmed with the porous ceramics of Production Example 7 and Production Example 8.

TABLE 12

Effect of the Porous Ceramic on Enteropathogenic *Escherichia Coli*

| | | Concentration (ppm) | Number of Growing Colonies per Plate | |
|---|---|---|---|---|
| | | | Day 1 of Culture | Day 2 of Culture |
| Test Sample | Production Example 4: Formula (TOCM) | 100 | 59 | 59 |
| Control | No Addition of Ceramic Powder | 0 | 106 | 106 |

TABLE 13

Effect of the Porous Ceramic on Enteropathogenic *Escherichia Coli*

| | | Concentration (ppm) | Number of Growing Colonies per Plate | |
|---|---|---|---|---|
| | | | Day 2 of Culture | Day 5 of Culture |
| Test Sample | Production Example 4: Formula (TOCM) | 1000 | 0 | 0 |
| Control | No Addition of Ceramic Powder | 0 | 175 | 175 |

Test Example 39: Dysentery *Bacillus*

A study was performed to examine an antibacterial effect on dysentery *bacillus*. The ceramic powder of Production Example 4 as a typical example of the porous ceramic represented by formula (TOCM) was added to a nutrient agar medium to give a concentration of 1000 µg/mL, and 20 mL of the mixture was added to a plastic Petri dish (diameter: 90 mm) and solidified, followed by application of 0.1 mL of a dysentery *bacillus* liquid (bacterial count: $10^3$/mL) thereto. After culture for 2 and 5 days, the number of growing colonies on the test plate was measured. The culture temperature was 35° C. As a control, the same test was performed without adding the ceramic powder.

Table 14 shows the results. When the porous ceramic of Production Example 4 represented by formula (TOCM) was used, all of the dysentery *bacillus* were already dead on day 2 of culture. The same results were confirmed with the porous ceramics of Production Example 11 and Production Example 12.

TABLE 14

The Effect of the Porous Ceramic on Dysentery *Bacillus*

| | | Concentration (ppm) | Number of Growing Colonies per Plate | |
|---|---|---|---|---|
| | | | Day 2 of Culture | Day 5 of Culture |
| Test Sample | Production Example 4: Formula (TOCM) | 1000 | 0 | 0 |
| Control | No Addition of Ceramic Powder | 0 | 113 | 113 |

Reference Example 2: *Bacillus subtilis*

A study was performed to examine antibacterial activity on *Bacillus subtilis*. *Bacillus subtilis* was cultured in an LB liquid medium at 37° C. for 1 day to prepare its culture solution. Subsequently, the ceramic powder of Production Example 4 as a typical example of the porous ceramic represented by formula (TOCM) was added to a nutrient agar medium to give a concentration of 0, 1, 10, 100, or 1000 µg/mL. 20 mL of the resultant was added to a plastic Petri dish (diameter: 90 mm) and solidified to prepare an agar plate, followed by application of 0.3 mL of the culture solution (bacterial count: $10^3$/mL) to the agar medium. After culture for 1 day, the number of growing colonies on the test plate was measured. As a result, *Bacillus subtilis* proliferated in every case, regardless of the concentration of the ceramic powder. An antibacterial effect on *Bacillus subtilis* was not confirmed even with the concentration of 1000 µg/mL.

While the porous ceramic was confirmed to have effective antibacterial effects on bacteria poisonous for humans, such as *pylori* bacteria in Test Example 17, *Staphylococcus aureus* in Test Example 34, *Campylobacter* bacterium in Test Example 37, enteropathogenic *Escherichia coli* in Test Example 38, and dysentery *bacillus* in Test Example 39, the ceramic did not exhibit an inhibitory effect on bacteria good for humans, such as *Bacillus subtilis*. The results of this study demonstrate an example that supports the understanding of the oral intake of the porous ceramic of the present invention as having no adverse effect on the intestinal flora.

Test Example 40: Norovirus

An inactivation test was performed to examine whether the ceramic powder of Production Example 4 as a typical example of the porous ceramic represented by formula (TOCM) inactivates feline calicivirus (FCV:F9 strain), widely used as an alternative virus for human norovirus. The following describes the outline of the test system.

Equivalent amounts of a serum-free MEM culture to which 2000 ppm of the ceramic powder was added and a feline calicivirus solution adjusted to $5.0 \times 10^6$ $TCID_{50}$/ml (solvent: 5% serum-containing MEM) were mixed, and reacted at below 4° C. 24 hours after the start of the reaction, the reaction solution was collected and filtered through a membrane filter with a pore size of 0.2 µm to separate the ceramic powder from the reaction solution. The collected filtrate was immediately subjected to $TCID_{50}$ assay using a cat-kidney-derived cell line (CRFK cell) to determine the viral titer.

The viral titer determined in each test was compared with the titer in the absence of the test sample to evaluate the FCV inactivation action of the test sample. The test was performed with N=2 (duplicate). Table 15 shows the results of measuring the viral titer. Table 16 shows the value relative to the average of the control after 24 hours taken as 100%.

TABLE 15

Results of Measuring the Viral Titer

| | | | FCV Tier ($TCID_{50}$/mL) | |
|---|---|---|---|---|
| | | Time (h) | Average | Standard Deviate |
| Test Sample | Production Example 4: Formula (TOCM) | 0 | 3,905,853 | 1,547,357 |
| | | 24 | 198,298 | 117,200 |
| Control | No Addition of Ceramic Powder | 0 | 3,905,853 | 1,547,357 |
| | | 24 | 2,218,639 | 901,561 |

TABLE 16

FCV Titer Relative Value and P Value
Determined from Student's t-Test

| | | FCV Titer Relative Value (%) | | |
|---|---|---|---|---|
| | | Average | Standard Deviate | P Value |
| Test Sample | Production Example 4: Formula (TOCM) | 8.9 | 5.3 | <0.01 |
| Control | No Addition of Ceramic Powder | 100 | 40.6 | |

The results reveal that subjecting feline calicivirus together with a test sample containing 2000 ppm of the ceramic powder to a reaction at below 4° C. for 24 hours can significantly decrease the viral titer statistically, producing a noticeable inactivation effect.

Norovirus has a potent second infectious capacity, and people catch the infection through a transmission route such as contact with a carrier or eating cooked food that a carrier has been in contact with, and develop diarrhea and fever. Preventive measures such as adequate hand washing are important, but there is no way to find the virus in food such as sliced raw fish (uncooked fish) and raw vegetables. It is ideal to, as much as possible, not come into contact with such food, but a more desirable approach is to sanitize food or perform antibacterial treatment on food by using a material that is safe to eat and harmless, without damaging food quality. In principle, it is possible to sanitize food by spraying, for example, commonly used hypochlorous acid, but this method cannot be a practical solution due to its minimal antibacterial effect and accompanying smell. By contrast, the porous ceramic of the present invention is bland and odor-free, non-toxic, and usable as a starting material for food; in addition, the porous ceramic itself has a sterilizing effect and antibacterial effect. Thus, the porous ceramic has an advantage in its use because it can be sprayed on or added to raw food.

Test Example 41-1: Gene Toxicity Test (AMES Test)

A bacterial reverse mutation assay was performed to examine mutagenesis induction by the ceramic powder of Production Example 4 as a typical example of the porous ceramic represented by formula (TOCM). The assay was performed in compliance with the GLP in the Ordinance on Implementation Standards for Non-Clinical Studies on Safety of Drugs (MHW Ordinance No. 21, Mar. 26, 1997) with reference to the OECD Guideline for the Testing of Chemicals 471 (Jul. 21, 1997: Bacterial Reverse Mutation Test) set by the OECD.

To examine mutagenesis induction by the ceramic powder, a reverse mutation assay was performed using *Salmonella typhimurium* (TA100, TA98, TA1535 and TA1537 strains) and *Escherichia coli* (WP2 uvrA strain). The assay was performed with a preincubation technique both in the presence of a metabolic activation system of rat liver S9 (+S9 treatment) and in the absence of the metabolic activation system (−S9 treatment). The groups for testing the ceramic powder were treated with doses including the highest dose prescribed in the guideline (the pre-test: 0.500 to 5000 μg/plate, the dose-finding study: 0.762 to 5000 μg/plate, the main test: 19.5 to 5000 μg/plate).

As a result, regardless of the presence or absence of the metabolic activation system, the increase in revertant colonies in the groups treated with the ceramic powder was less than twice that in the negative control group. The negative result in the dose-finding study was reproduced in this test. The positive control substance clearly had mutagenic activity on each bacterial strain. From the results, the ceramic powder was confirmed to not have a mutagenesis-inducing effect (negative) on bacteria under the conditions in the test.

Test Example 41-2: Genotoxicity Assay (Micronucleus-Comet Combination Assay)

A micronucleus-comet combination assay was performed using rats to examine whether the ceramic powder of Production Example 4 as a typical example of the porous ceramic represented by formula (TOCM) damages DNA and induces micronucleated erythrocytes in vivo. The assay was performed in compliance with the GLP in the Ordinance on Implementation Standards for Non-Clinical Studies on Safety of Drugs (MHW Ordinance No. 21, Mar. 26, 1997) with reference to the OECD Guideline for the Testing of Chemicals 489 (Sep. 26, 2014: In Vivo Mammalian Alkaline Comet Assay) and the OECD Guideline for the Testing of Chemicals 474 (Jul. 21, 1997: Mammalian Erythrocyte Micronucleus Test) set by the OECD. The assay was also performed in compliance with the Act on Welfare and Management of Animals (Oct. 1, 1973, Act No. 105, final revision: Jun. 12, 2013, Act No. 38) and Standards Relating to the Care and Management of Laboratory Animals and Relief of Pain (Apr. 28, 2006, Ministry of the Environment, Notice No. 88, final revision: Aug. 30, 2013, Ministry of the Environment, Notice No. 84). The assay had been audited and permitted beforehand by the animal testing committee of the institution where the assay was performed, and the assay was conducted in accordance with the ethical animal assessment criteria prescribed in the guidelines for animal experiments (Jun. 2, 2014) set by the institution.

Crl:CD(SD) male rats were orally administered the ceramic powder once daily for three consecutive days at three different doses: the highest dose of 2000 mg/kg, which is the upper limit in the guideline, 1000 mg/kg, and 500 mg/kg. Three hours after the final administration, their livers and stomachs were harvested for the comet assay and femurs for the micronucleus test, and specimens were prepared. The comet assay measured the percentage of tail DNA (% TD), which is an indication of DNA damage. The micronucleus test measured the frequency of micronucleated immature erythrocytes (MNIE) and the ratio of the immature erythrocyte count (IE) to the observed erythrocyte count.

As a result, there was no statistically significant increase in the % TD and MNIE of the group treated with the test substance. The ratio of IE exhibited a statistically significant increase in the case of doses 1000 and 2000 mg/kg, but still remained within the standard (average±3SD) determined from the background data of the test facility. The results indicate that the ceramic powder does not induce micronuclei in rat bone-marrow cells and does not damage DNA in the liver or stomach (negative) under the test conditions.

Test Example 42: Acute Oral Toxicity Assay (Single Dose)

An assay was performed using rats to examine acute oral toxicity of the ceramic powder of Production Example 4 as a typical example of the porous ceramic represented by formula (TOCM). The assay was performed in compliance with the GLP in the Ordinance on Implementation Standards for Non-Clinical Studies on Safety of Drugs (MHW Ordinance No. 21, Mar. 26, 1997) with reference to the OECD Guideline for the Testing of Chemicals 420 (Dec. 17, 2001: Acute Oral Toxicity—Fixed Dose Procedure) set by the OECD. The assay was also performed in compliance with the Act on Welfare and Management of Animals (Oct. 1, 1973, Act No. 105, final revision: Jun. 12, 2013, Act No. 38) and the Standards Relating to the Care and Management of Laboratory Animals and Relief of Pain (Apr. 28, 2006, Ministry of the Environment, Notice No. 88, final revision: Aug. 30, 2013, Ministry of the Environment, Notice No. 84). The assay had been audited and permitted beforehand by the animal testing committee of the institution where the assay was performed, and the assay was conducted in accordance with the ethical animal assessment criteria prescribed in the guidelines for animal experiments (Jun. 2, 2014) set by the institution.

To examine the acute oral toxicity of the ceramic powder, 7 to 8-week-old Crl:CD(SD) female rats (five rats) that had been fasted overnight were orally administered the test substance by gavage at a single dose of 2000 mg/kg. For 14 days from the administration, the general state and body weight change of the animals were observed. After completion of the observation period, the various organs and tissues of their entire body were visually observed (autopsy). During the observation period, no rats died, and no toxic effects on the general state or body weight change were observed. The autopsy also found no abnormality that may possibly be caused by the administration of the test substance. Thus, under these test conditions, the toxicity of the ceramic powder was not confirmed in the observation, measurement, or test, and the $LD_{50}$ of the ceramic powder for rats was considered to be over 2000 mg/kg for a single oral administration.

Test Example 43: Chronic Oral Toxicity Assay (Multiple Dose)

An assay was performed using rats to examine chronic oral toxicity of the ceramic powder of Production Example 4 as a typical example of the porous ceramic represented by formula (TOCM). With reference to the OECD Guideline for the Testing of Chemicals 408 (Sep. 21, 1998: Repeated Dose 90-day Oral Toxicity Study in Rodents), rats were orally administered multiple doses of the ceramic powder for 14 days, and the toxicity of the test substance caused by repeated exposure was examined. The assay was performed in compliance with the Act on Welfare and Management of Animals (Oct. 1, 1973, Act No. 105, final revision: Jun. 12, 2013, Act No. 38) and Standards Relating to the Care and Management of Laboratory Animals and Relief of Pain (Apr. 28, 2006, Ministry of the Environment, Notice No. 88, final revision: Aug. 30, 2013, Ministry of the Environment, Notice No. 84). The assay had been audited and permitted beforehand by the animal testing committee of the institution where the assay was performed in compliance with the ethical animal assessment criteria prescribed in the guidelines for animal experiments (Jun. 2, 2014) set by the institution.

Crl:CD(SD) rats (a group of 5 male rats and a group 5 female rats) were repeatedly orally administered the ceramic powder obtained in Production Example 4 as a test substance at a dose of 0, 100, 300, and 1000 mg/kg/day for 14 days. Throughout the dosing period, the general state of the rats was observed, and the body weight and food consumption were measured. After completion of the dosing period, hematological assessment, organ weight measurement, and visual observation of various organs of the entire body (autopsy) were performed. As a result, there was no fatal case in any group throughout the assay period, and there was no toxic change caused by administration of the test substance in observation of general state, measurement of body weight and food consumption, hematological assessment, measurement of organ weight, or autopsy. Thus, the groups administered the test substance even at a dose of 1000 mg/kg/day under the assay conditions exhibited no toxic change caused by administration of the test substance in the observation, measurement, or assessment.

Those skilled in the art can add various modifications to the pharmaceutical compositions, cosmetic products, food or drink products, and the use of these disclosed herein, without departing from the spirit and scope of the invention. Similar substitutes and modifications are considered to be within the scope of the invention.

The invention claimed is:
1. A method for:
treating a symptom or disease selected from the group consisting of Crohn's disease, polyglutamine disease, influenza A virus H1N1 infections, influenza A virus (H3N2), dyslipidemia, atopic dermatitis, stomatitis, endocarditis caused by *Streptococcus mutans* SA31,
or eradicating at least one type of bacteria selected from the group consisting of *Helicobacter pylori* bacteria, *Streptococcus mutans* SA31, enteropathogenic *Escherichia coli*, *Campylobacter* bacteria, dysentery bacillus, and *Staphylococcus aureus* or a virus selected from the group consisting of influenza A, HIV in vitro, and norovirus;
the method comprising administering an effective amount of a pharmaceutical composition to a subject in need thereof, wherein administering the effective amount of the pharmaceutical composition to the subject in need thereof comprises orally ingesting the pharmaceutical composition, spraying the pharmaceutical composition, administering the pharmaceutical composition into blood, or administering the pharmaceutical composition transdermally, and wherein the pharmaceutical composition comprises- a porous ceramic obtained by combustion synthesis of a starting material comprising titanium, silver, and carbon or a radical- and nanobubble-containing liquid obtained by bringing the porous ceramic into contact with a liquid.

2. The method according to claim 1, wherein the starting material further comprises at least one member selected from the group consisting of gold, platinum, iron, and copper.

3. The method according to claim 1, wherein the porous ceramic has a structure in which positive charge and negative charge are finely dispersed.

4. The method according to claim 1, wherein the porous ceramic comprises an oxide ceramic layer partially or entirely on the surface thereof.

5. The method according to claim 1, wherein the porous ceramic is a molded body or a ground material of the molded body.

6. The method of claim 1, wherein the combustion synthesis of the starting material comprises:
igniting the starting material to initiate a chemical reaction; and
initiating a chain reaction with heat from the chemical reaction.

7. The method of claim 1, wherein the porous ceramic obtained by the combustion synthesis comprises particles having a mean pore size of 0.1 μm to 30 μm.

8. The method of claim 1, wherein the porous ceramic obtained by the combustion synthesis comprises particles having a particle size of 0.5 μm to 100 μm.

9. The method of claim 1, wherein the pharmaceutical composition is in the form of a tablet, a capsule, a pill, a powder, a granule, a liquid, an emulsion, a suspension, a syrup, a paste, an injectable agent, a candy, a gum, a sheet, an ointment, an injectable solution, an infusion, an atomization inhaler, or a spray.

* * * * *